US009617551B2

(12) United States Patent
Merlo et al.

(10) Patent No.: US 9,617,551 B2

(45) Date of Patent: Apr. 11, 2017

(54) **METHOD OF INCREASING PLANT TRANSFORMATION FREQUENCY USING MODIFIED STRAINS OF *AGROBACTERIA***

(75) Inventors: Donald J. Merlo, Carmel, IN (US); Sean M. Russell, Carmel, IN (US); Diane M. Retallack, Poway, CA (US); Aaron T. Woosley, Fishers, IN (US); Thomas Meade, Zionsville, IN (US); Kenneth Narva, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 824 days.

(21) Appl. No.: 13/812,469

(22) PCT Filed: Jul. 29, 2011

(86) PCT No.: PCT/US2011/046028

§ 371 (c)(1),
(2), (4) Date: Mar. 21, 2013

(87) PCT Pub. No.: WO2012/016222

PCT Pub. Date: Feb. 2, 2012

(65) Prior Publication Data

US 2015/0267213 A1 Sep. 24, 2015

Related U.S. Application Data

(60) Provisional application No. 61/368,965, filed on Jul. 29, 2010.

(51) Int. Cl.
*C12N 15/82* (2006.01)
*C12N 15/74* (2006.01)

(52) U.S. Cl.
CPC ......... *C12N 15/8205* (2013.01); *C12N 15/74* (2013.01); *C12N 15/8274* (2013.01); *C12N 15/8286* (2013.01)

(58) Field of Classification Search
None
See application file for complete search history.

(56) References Cited

U.S. PATENT DOCUMENTS

| | | | |
|---|---|---|---|
| 5,731,179 A | 3/1998 | Komari et al. | |
| 7,393,946 B1 | 7/2008 | Memelink | |
| 2006/0174372 A1 | 8/2006 | Malvar et al. | |
| 2006/0174375 A1 | 8/2006 | Lightner et al. | |
| 2006/0212973 A1 | 9/2006 | Zilinskas et al. | |
| 2009/0012275 A1 | 1/2009 | Schymkowitz et al. | |
| 2009/0075358 A1 | 3/2009 | Jefferson | |
| 2011/0189775 A1* | 8/2011 | Ainley | A01H 1/06 435/455 |

FOREIGN PATENT DOCUMENTS

| | | |
|---|---|---|
| JP | H03224487 | 10/1991 |
| JP | H08506489 | 7/1996 |
| JP | H1080289 | 3/1998 |
| JP | H10155485 | 6/1998 |
| JP | 2007535327 | 12/2007 |
| WO | 9516031 | 6/1995 |
| WO | 9849332 | 11/1998 |
| WO | 9854961 | 12/1998 |
| WO | 0018939 | 4/2000 |
| WO | 2005107437 | 11/2005 |
| WO | 2007148819 | 12/2007 |
| WO | 2008001414 | 1/2008 |

OTHER PUBLICATIONS

Kan Wang (editor) (Agrobacterium Protocols. Methods in Molecular Biology, 2006).*

Gatehouse (Biotechnological Prospects for Engineering Insect-Resistant Plants. Plant Physiology, vol. 146, pp. 881-887, Mar. 2008).*

Komori et al (Update on Binary Vectors. Current Status of Binary Vectors and Superbinary Vectors. Plant Physiology, vol. 145, pp. 1155-1160, Dec. 2007).*

(Continued)

*Primary Examiner* — Medina A Ibrahim
*Assistant Examiner* — Wayne Zhong
(74) *Attorney, Agent, or Firm* — Marcos P. Rivas; Magleby Cataxinos & Greenwood

(57) ABSTRACT

*Agrobacterium* strains that harbor transformation-enhancing genes on a plasmid capable of replication independently of the *Agrobacterium* chromosome, the Ti plasmid, and plant transformation binary vectors, and uses for these *Agrobacterium* strains are provided. Additionally, *Agrobacterium* strains that are deficient in DNA recombination functions that result in instability or rearrangement of plant transformation binary vectors, and that harbor transformation-enhancing genes on a plasmid capable of replication independently of the *Agrobacterium* chromosome, the Ti plasmid, and plant transformation binary vectors, and uses for these strains, are also provided. Further included are *Agrobacterium* strains that harbor transformation-enhancing genes integrated into the *Agrobacterium* chromosome at a locus that does not interfere with or otherwise compromise the normal growth and plant transformation ability of the *Agrobacterium* cells, and uses for these *Agrobacterium* strains. Plants made using these *Agrobacterium* strains are also described.

14 Claims, 5 Drawing Sheets

(56) References Cited

OTHER PUBLICATIONS

Hamilton et al (Stable transfer of intact high molecular weight DNA into plant chromosomes. Proc. Natl. Acad. Sci. USA. vol. 93, pp. 9975-9979, Sep. 1996).*

Krishnamohan et al (Efficient vir Gene Induction in Agrobacterium tumefaciens Requires virA, virG, and vir Box from the Same Ti Plasmid. Journal of Bacteriology, p. 4079-4089, Jul. 2001).*

Lin et al (Efficient linking and transfer of multiple genes by a multigene assembly and transformation vector system. PNAS. 100: 5962-5967, May 13, 2003).*

Hood et al., "New Agrobacterium helper plasmids for gene transfer to plants," Transgenic Research, 1993, pp. 209-218, vol. 2.

Jin, S G et al: "Genes responsible for the supervirulence phenotype of Agrobacterium tumefaciens A281", Journal of Bacteriology, Jan. 1987 (Jan. 1, 1987), pp. 4417-4425, vol. 169, No. 10, 1.

Kiyokawa et al: "Construction of Disarmed Ti Plasmids Transferable between *Escherichia coli* and *Agrobacterium* Species", Applied and Environmental Microbiology, vol. 75, No. 7, Apr. 1, 2009 (Apr. 1, 2009), pp. 1845-1851.

Lazo, G. R., et al., "A DNA Transformation—Competent Arabidopsis Genomic Library in Agrobacterium," Biotechnology 1991, pp. 963-967, vol. 9.

Lee, Lan-Ying et al., "T-DNA Binary Vectors and Systems," Plant Physiology, Feb. 2008, pp. 325-332, vol. 146.

Frary, A., et al., "Efficiency and stability of high molecular weight DNA transformation: an analysis in tomato," Transgenic Res., Apr. 2001, pp. 121-132, vol. 10, No. 2.

Gelvin, Stanton B, "Agrobacterium-mediated plant transformation: the biology behind the gene-jockeying tool" Microbiology and Molecular Biology Reviews, American Society for Microbiology, Mar. 1, 2003, pp. 16-37, vol. 67, No. 1.

Ishida, Y et al., "High efficiency transformation of maize (*Zea mays* l.) mediated by agrobacterium tumefaciens," Biotechnology, Jun. 1, 1996, pp. 745-750, vol. 14, No. 6.

Komari et al., Vectors carrying two separate t-dnas of co-transformation of higher plants medicated by agrobacterium tumefaciens and segregation of transformants free from selection markers, The plant journal, Jan. 1, 1996, pp. 165-174, vol. 10, No. 1.

Hellens, Roger et al., "Technical Focus: A Guide to Agrobacterium Binary Ti Vectors" Trends in Plant Science, 2000, pp. 446-451 vol. 5, No. 10.

International Search Report for PCT/US2011/046028, dated Apr. 6, 2012.

Written Opinion for PCT/US2011/046028, dated Apr. 6, 2012.

* cited by examiner

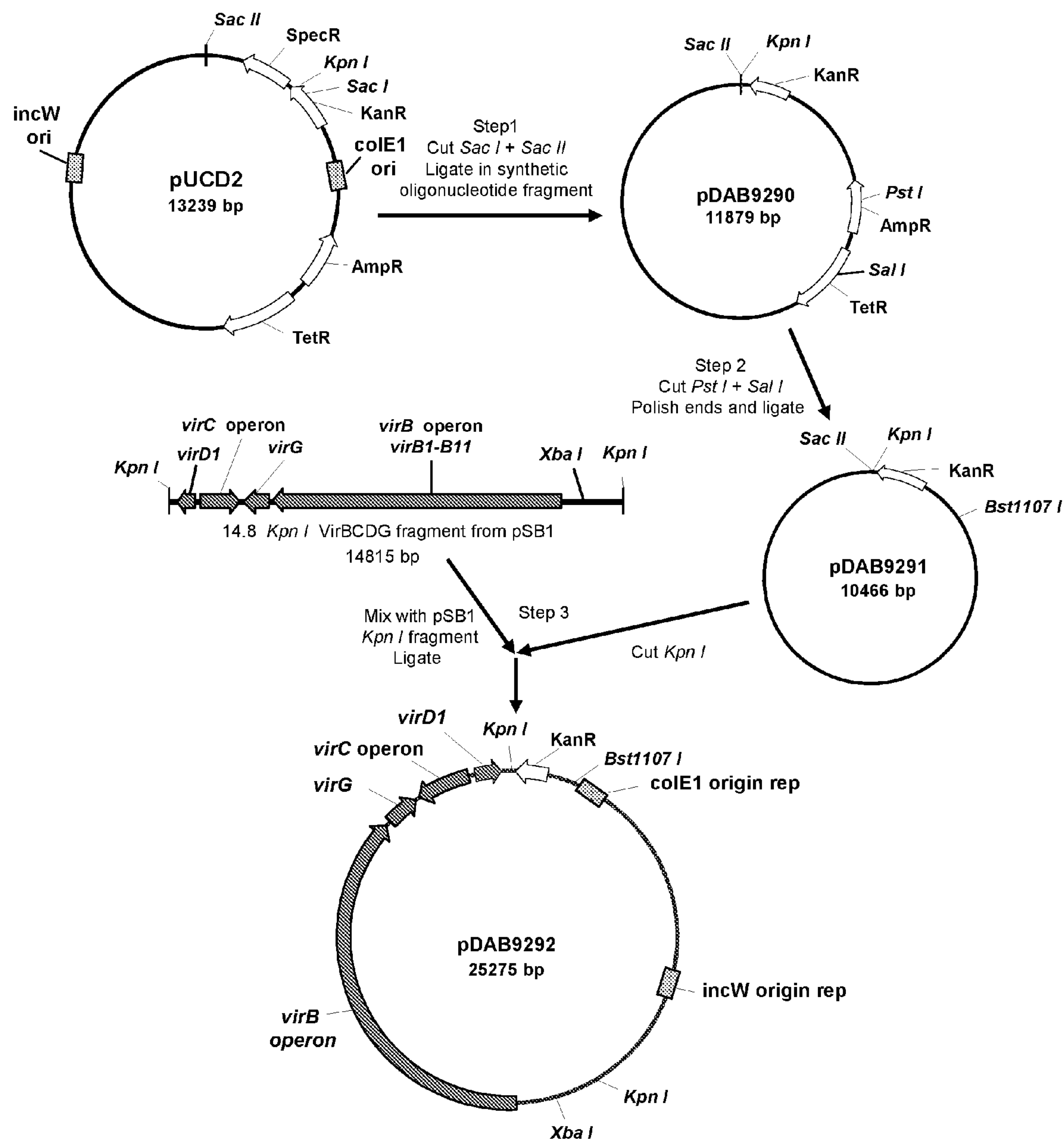

Oligonucleotide for Step 1

```
--GGGGTACCCGCTACCCGGGTCATGATGTCTAACGTTTGACATGAGGGGCGGCCAAGGGCGCCAGCCCTTGGAC
CGCCCCATGGGCGATGGGCCCAGTACTACAGATTGCAAACTGTACTCCCCGCCGGTTCCCGCGGTCGGGAACCTG

GTCCCCCTCGATGGAAGGGTTAGGCATCACTGCGTGTTCGCTCGAATGCCTGGCGTGTTTGAACCATGTACACGG
CAGGGGGAGCTACCTTCCCAATCCGTAGTGACGCACAAGCGAGCTTACGGACCGCACAAACTTGGTACATGTGCC

CTGGACCATCTGGGGTGGTTACAGTACCTTGCCTCTCAAACCCCGCTTTCTCGTAGCATCGGATCGCTCGCAAGT
GACCTGGTAGACCCCACCAATGTCATGGAACGGAGAGTTTGGGGCGAAAGAGCATCGTAGCCTAGCGAGCGTTCA

TGCTCGGCGACGGGTCCGTTTGGATCTTGGTGACTTCGGGATCATTGAACAGCAACTCAACCAGAGCT
ACGAGCCGCTGCCCAGGCAAACCTAGAACCACTGAAGCCCTAGTAACTTGTCGTTGAGTTGGTC----
```

Fig. 1

Fig. 4A
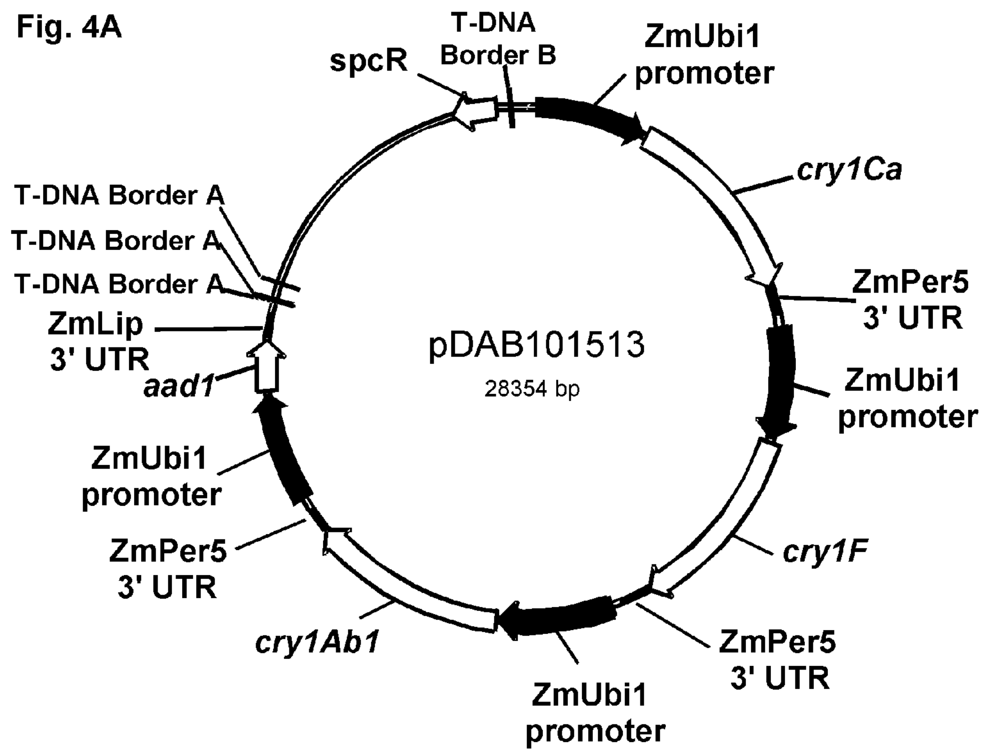
Fig. 4B
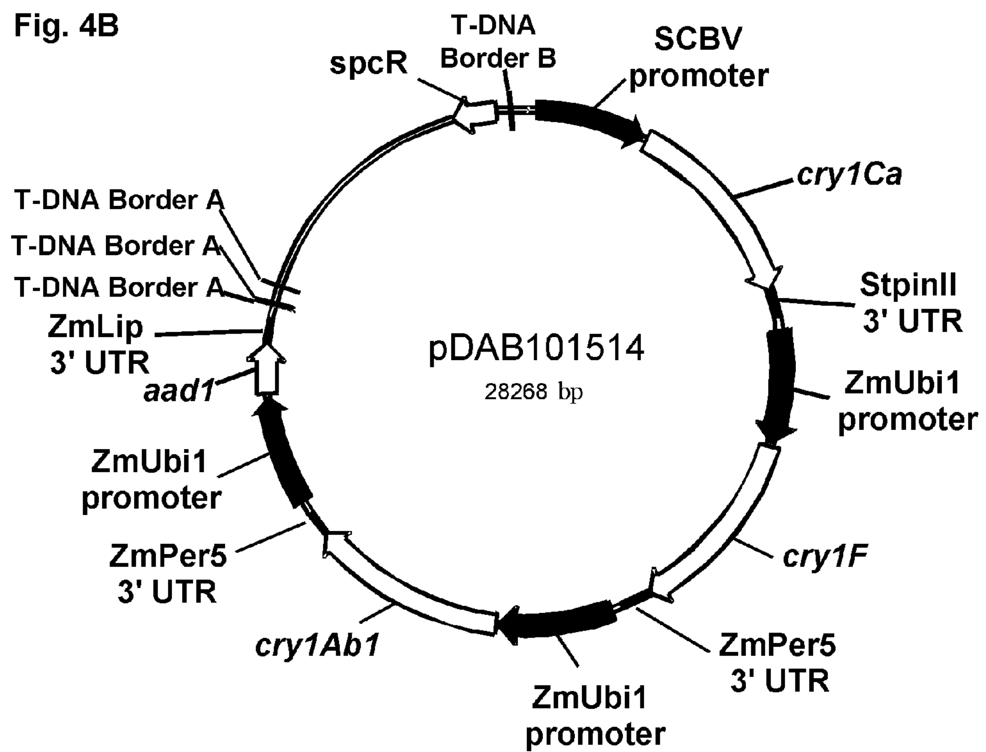
Fig. 4

SEQUENCE LISTING

<160> NUMBER OF SEQ ID NOS: 35

<210> SEQ ID NO 1
<211> LENGTH: 13239
<212> TYPE: DNA
<213> ORGANISM: Artificial Sequence
<220> FEATURE:
<223> OTHER INFORMATION: Plasmid

<400> SEQUENCE: 1

```
ccgcggtgac agcgccggcg gggtctagcc gccggctctc atcgaagaag gagtcctcgg      60

tgagattcag aatgccgaac accgtcacca tggcgtcggc ctccgcagcg acttccacga     120

tggggatcgg gcgagcaaaa aggcagcaat tatgagcccc atacctacaa agccccacgc     180

atcaagcttt tgcccatgaa gcaaccaggc aatggctgta attatgacga cgccgagtcc     240

cgaccagact gcataagcaa caccgacagg gatggatttc agaaccagag aaagaaaata     300

aaatgcgatg ccataaccga ttatgacaac ggcggaaggg gcaagcttag taaagccctc     360

gctagatttt aatgcggatg ttgcgattac ttcgccaact attgcgataa caagaaaaag     420

ccagcctttc atgatatatc tcccaatttg tgtagggctt attatgcacg cttaaaaata     480

ataaaagcag acttgacctg atagtttggc tgtgagcaat tatgtgctta gtgcatctaa     540

cgccggagtt aagccgccgc gcgtagcgcg gtcggcttga acgaattgtt agacatcatt     600

taccaactga cttgatgatc tcgcctttca caaagcgaat aaattcttcc aagtgatctg     660

cgcgtgaggc caagtgatct tctttttgtc ccagataagc ttgcttagct tcaagtaaga     720
```

-continued

```
cgggctgata ctgggcaggt aggcgtttta ttgcccagtc ggcagcgaca tccttcggcg    780
cgattttgcc ggttattgcg ctgtaccaaa tgcgggacaa cgtaagcact acatttcgct    840
catcgccggc ccagtcgggc tgcgagttcc atagcttcaa ggtttccctc agcgcctcga    900
atagatcctg ttcaggaacc gggtcaaaga attcctccgc tgccggacct accaaggcaa    960
cgctatgttc tcttgctttt gtaagcagga tagctagatc aatgtcgatc atggctggct   1020
cgaagatacc cgcaagaatg tcattgcgct gccattctcc aaattgcagc tcgcgcttag   1080
ccggataacg ccacgggatg atgtcgtcat gcacgacaag ggtgacttct atagcgcgga   1140
gcgtctcgct ctcgccaggg aaagccgaag cctccataag gtcattgagc aatgctcgcc   1200
gcgtcgtttc atcaagcttt acggccacag taaccaacaa atcaatatcg ctgtatggct   1260
tcaggccgcc atccactgcg gagccgtaca aatgcacggc cagcaacgtt gattccagat   1320
ggcgctcaat gacgcttagc acctctgata gttggttcga aatttcgatg gtcaccgcta   1380
ccctcatgat gtctaacgtt tgacatgagg ggcggccaag ggcgccagcc cttggacgtc   1440
cccctcgatg gaagggttag gcatcactgc gtgttcgctc gaatgcctgg cgtgtttgaa   1500
ccatgtacac ggctggacca tctggggtgg ttacggtacc ttgcctctca aaccccgctt   1560
tctcgtagca tcggatcgct cgcaagttgc tcggcgacgg gtccgtttgg atcttggtga   1620
cctcgggatc attgaacagc aactcaacca gagctcgaac cagcttggtt cccaagcctt   1680
tgcccagttg tgatgcattc gccagtgact ggtctattcc gcgtactcct ggatcggttt   1740
cttcttccca ccatccgtcc ccgcttccaa gagcaacgta cgactgggca tacccaatcg   1800
gctctccatt cagcattgca atgtatggag tgacggactc ttgcgctaaa acgcttggca   1860
agtactgttc ctgtacgtca gcaagtgtcg ggcgtgcttc ttctccgccc caccactcga   1920
cgatatgaga tcgatttagc cactcataga gcatcgcaag gtcatgctca gtcatgaggc   1980
gcagtgtgac ggaatcggtg ctgttggtca cgatgctgta ctttgtgatg cctaactttg   2040
ttttagggcg actgccctgc tgcgtaacat cgttgctgct ccataacatc aaacatcgac   2100
ccacggcgta acgcgcttgc tgcttggatg cccgaggcat agactgtaca aaaaaacagt   2160
cataacaagc catgaaaacc gccactgcgc cgttaccacc gctgcgttcg gtcaaggttc   2220
tggaccagtt gcgtgagcgc atacgctact tgcattacag tttacgaacc gaacaggctt   2280
atgtcaactg ggttcgtgcc ttcatccgtt tccacggtgt gcgtcacccg gcaaccttgg   2340
gcagcagcga agtcgaggca tttctgtcct ggctggcgaa cgagcgcaag gtttcggtct   2400
ccacgcatcg tcaggcattg gcggccttgc tgttcttcta cggcaaggtg ctgtgcacgg   2460
atctgccctg gcttcaggag atcggaagac ctcggccgtc gcggcgcttg ccggtggtgc   2520
tgaccccgga tgaagtggtt cgcatcctcg gttttctgga aggcgagcat cgtttgttcg   2580
cccagcttct gtatggaacg ggcatgcgga tcagtgaggg tttgcaactg cgggtcaagg   2640
atctggattt cgatcacggc acgatcatcg tgcgggaggg caagggctcc aaggatcggg   2700
ccttgatgtt acccgagagc ttggcaccca gcctgcgcga gcagctgcct cgcgcgtttc   2760
ggtgatgacg gtgaaaacct ctgacacatg cagctcccgg agacggtcac agcttgtctg   2820
taagcggatg ccgggagcag acaagcccgt cagggcgcgt cagcgggtgt tggcgggtgt   2880
cggggcgcag ccatgaccca gtcacgtagc gatagcggag tgtatactgg cttaactatg   2940
cggcatcaga gcagattgta ctgagagtgc accatatgcg gtgtgaaata ccgcacagat   3000
gcgtaaggag aaaataccgc atcaggcgct cttccgcttc ctcgctcact gactcgctgc   3060
```

```
gctcggtcgt tcggctgcgg cgagcggtat cagctcactc aaaggcggta atacggttat   3120
ccacagaatc aggggataac gcaggaaaga acatgtgagc aaaaggccag caaaaggcca   3180
ggaaccgtaa aaaggccgcg ttgctggcgt ttttccatag gctccgcccc cctgacgagc   3240
atcacaaaaa tcgacgctca agtcagaggt ggcgaaaccc gacaggacta taaagatacc   3300
aggcgtttcc ccctggaagc tccctcgtgc gctctcctgt tccgaccctg ccgcttaccg   3360
gatacctgtc cgcctttctc ccttcgggaa gcgtggcgct ttctcatagc tcacgctgta   3420
ggtatctcag ttcggtgtag gtcgttcgct ccaagctggg ctgtgtgcac gaaccccccg   3480
ttcagcccga ccgctgcgcc ttatccggta actatcgtct tgagtccaac ccggtaagac   3540
acgacttatc gccactggca gcagccactg gtaacaggat tagcagagcg aggtatgtag   3600
gcggtgctac agagttcttg aagtggtggc ctaactacgg ctacactaga aggacagtat   3660
ttggtatctg cgctctgctg aagccagtta ccttcggaaa aagagttggt agctcttgat   3720
ccggcaaaca aaccaccgct ggtagcggtg gtttttttgt ttgcaagcag cagattacgc   3780
gcagaaaaaa aggatctcaa gaagatcctt tgatcttttc tacggggtct gacgctcagt   3840
ggaacgaaaa ctcacgttaa gggattttgg tcatgagatt atcaaaaagg atcttcacct   3900
agatcctttt aaattaaaaa tgaagtttta aatcaatcta aagtatatat gagtaaactt   3960
ggtctgacag ttaccaatgc ttaatcagtg aggcacctat ctcagcgatc tgtctatttc   4020
gttcatccat agttgcctga ctccccgtcg tgtagataac tacgatacgg gagggcttac   4080
catctggccc cagtgctgca atgataccgc gagacccacg ctcaccggct ccagatttat   4140
cagcaataaa ccagccagcc ggaagggccg agcgcagaag tggtcctgca actttatccg   4200
cctccatcca gtctattaat tgttgccggg aagctagagt aagtagttcg ccagttaata   4260
gtttgcgcaa cgttgttgcc attgctgcag gcatcgtggt gtcacgctcg tcgtttggta   4320
tggcttcatt cagctccggt tcccaacgat caaggcgagt tacatgatcc cccatgttgt   4380
gcaaaaaagc ggttagctcc ttcggtcctc cgatcgttgt cagaagtaag ttggccgcag   4440
tgttatcact catggttatg gcagcactgc ataattctct tactgtcatg ccatccgtaa   4500
gatgcttttc tgtgactggt gagtactcaa ccaagtcatt ctgagaatag tgtatgcggc   4560
gaccgagttg ctcttgcccg gcgtcaacac gggataatac cgcgccacat agcagaactt   4620
taaaagtgct catcattgga aaacgttctt cggggcgaaa actctcaagg atcttaccgc   4680
tgttgagatc cagttcgatg taacccactc gtgcacccaa ctgatcttca gcatctttta   4740
ctttcaccag cgtttctggg tgagcaaaaa caggaaggca aaatgccgca aaaaagggaa   4800
taagggcgac acggaaatgt tgaatactca tactcttcct ttttcaatat tattgaagca   4860
tttatcaggg ttattgtctc atgagcggat acatatttga atgtatttag aaaaataaac   4920
aaataggggt tccgcgcaca tttccccgaa aagtgccacc tgacgtctaa gaaaccatta   4980
ttatcatgac attaacctat aaaaataggc gtatcacgag gccctttcgt cttcaagaat   5040
tctcatgttt gacagcttat catcgataag ctttaatgcg gtagtttatc acagttaaat   5100
tgctaacgca gtcaggcacc gtgtatgaaa tctaacaatg cgctcatcgt catcctcggc   5160
accgtcaccc tggatgctgt aggcataggc ttggttatgc cggtactgcc gggcctcttg   5220
cgggatatcg tccattccga cagcatcgcc agtcactatg gcgtgctgct agcgctatat   5280
gcgttgatgc aatttctatg cgcacccgtt ctcggagcac tgtccgaccg ctttggccgc   5340
cgcccagtcc tgctcgcttc gctacttgga gccactatcg actacgcgat catggcgacc   5400
acacccgtcc tgtggatcct ctacgccgga cgcatcgtgg ccggcatcac cggcgccaca   5460
```

```
ggtgcggttg ctggcgccta tatcgccgac atcaccgatg gggaagatcg ggctcgccac   5520
ttcgggctca tgagcgcttg tttcggcgtg ggtatggtgg caggccccgt ggccggggga   5580
ctgttgggcg ccatctcctt gcatgcacca ttccttgcgg cggcggtgct caacggcctc   5640
aacctactac tgggctgctt cctaatgcag gagtcgcata agggagagcg tcgaccgatg   5700
cccttgagag ccttcaaccc agtcagctcc ttccggtggg cgcggggcat gactatcgtc   5760
gccgcactta tgactgtctt ctttatcatg caactcgtag gacaggtgcc ggcagcgctc   5820
tgggtcattt tcggcgagga ccgctttcgc tggagcgcga cgatgatcgg cctgtcgctt   5880
gcggtattcg gaatcttgca cgccctcgct caagccttcg tcactggtcc cgccaccaaa   5940
cgtttcggcg agaagcaggc cattatcgcc ggcatggcgg ccgacgcgct gggctacgtc   6000
ttgctggcgt tcgcgacgcg aggctggatg gccttcccca ttatgattct tctcgcttcc   6060
ggcggcatcg ggatgcccgc gttgcaggcc atgctgtcca ggcaggtaga tgacgaccat   6120
cagggacagc ttcaaggatc gctcgcggct cttaccagcc taacttcgat cattggaccg   6180
ctgatcgtca cggcgattta tgccgcctcg gcgagcacat ggaacgggtt ggcatggatt   6240
gtaggcgccg ccctatacct tgtctgcctc cccgcgttgc gtcgcggtgc atggagccgg   6300
gccacctcga cctgaatgga agccggcggc acctcgctaa cggattcacc actccaagaa   6360
ttggagccaa tcaattcttg cggagaactg tgaatgcgca aaccaaccct tggcagaaca   6420
tatccatcgc gtccgccatc tccagcagcc gcacgcggcg catctcgggc agcgttgggt   6480
cctggccacg ggtgcgcatg atcgtgctcc tgtcgttgag gacccggcta ggctggcggg   6540
gttgccttac tggttagcag aatgaatcac cgatacgcga gcgaacgtga agcgactgct   6600
gctgcaaaac gtctgcgacc tgagcaacaa catgaatggt cttcggtttc cgtgtttcgt   6660
aaagtctgga aacgcggaag tcagcgccct gcaccattat gttccggatc tgcatcgcag   6720
gatgctgctg gctaccctgt ggaacaccta catctgtatt aacgaagcgc tggcattgac   6780
cctgagtgat ttttctctgg tcccgccgca tccataccgc cagttgttta ccctcacaac   6840
gttccagtaa ccgggcatgt tcatcatcag taacccgtat cgtgagcatc ctctctcgtt   6900
tcatcggtat cattaccccc atgaacagaa atccccctta cacggaggca tcagtgacca   6960
aacaggaaaa aaccgccctt aacatggccc gctttatcag aagccagaca ttaacgcttc   7020
tggagaaact caacgagctg gacgcggatg aacaggcaga catctgtgaa tcgcttcacg   7080
accacgctga tgagctttgt cgcgtgcacg ggcatggtgg ctgaaggacc aggccgaggg   7140
ccgcagcggc gttgcgcttc ccgacgccct tgagcggaag tatccgcgcg ccgggcattc   7200
ctggccgtgg ttctgggttt ttgcgcagca cacgcattcg accgatccac ggagcggtgt   7260
cgtgcgtcgc catcacatgt atgaccagac ctttcagcgc gccttcaaac gtgccgtaga   7320
acaagcaggc atcacgaagc ccgccacacc gcacaccctc cgccactcgt tcgcgacggc   7380
cttgctccgc agcggttacg acattcgaac cgtgcaggat ctgctcggcc attccgacgt   7440
ctctacgacg atgatttaca cgcatgtgct gaaagttggc ggtgccggag tgcgctcacc   7500
gcttgatgcg ctgccgcccc tcactagtga gaggtagggc agcgcaagtc aatcctggcg   7560
gattcactac ccctgcgcga aggccatcgg tgccgcatcg aacggccggt tgcggaaagt   7620
cctccctgcg tccgctgatg gccggcagca gcccgtcgtt gcctgatgga tccaacccct   7680
ccgctgctat agtgcagtcg gcttctgacg ttcagtgcag ccgtcttctg aaaacgacat   7740
ctggtgttcc tcattctctg gtggctgcgc ggcccggtgc gctttcttct cggcttggct   7800
```

-continued

```
tcgttcgcca gtctcatcac cctaccgatc atgtggcttg ggctggactc ggccaataag   7860
acccacatca tgctatcggt cgcaggcgtc ggccttggtg cgtcggccct catgtggttt   7920
tatgacgcgc ttctcatgag gctggcacca gaaccaatcc tattcagcac ctaaacgaag   7980
gccgggccac tcacccggcc ttttttgtac gctcataggg cagaacaaac caacgtttta   8040
tctataccgc aacagggtat ttaattccta tttaatctgc gctagaatga ggcatgttta   8100
accgaatctg acgttttccc tgcaaatgcc aaaatactat gcctatctcc gggtttcgcg   8160
tgacggccaa gacccggaaa accaaaaata cggtttgctc gaatacgcga acgccaaagg   8220
cttcgcgccg ctacagatcg aggaagaaat tgccagcaga gcaaaggact ggcgcaagcg   8280
caagctcgga gcaatcatcg aaaaggccga gcgtggcgac gtgctactga cgccggagat   8340
tacgcgcatt gccggttccg ccctcgccgc cttggaaatt ctcaaagcgg cgagcgagcg   8400
cggcctaatc gtccatgtga ccaaacagaa gatcatcatg gacggcagcc tacaaagcga   8460
catcatggca accgtgcttg gcttggctgc acagatcgag cggcatttca ttcaggcacg   8520
taccaccgag gcgctacaag tcgccagaga gcgcggcaag acgctcgggc gacccaaggg   8580
cagcaaatcg agcgccttga agctggacag ccgtattgat gaagtacagg catacgtgaa   8640
ccttggcttg ccgcaaagtc gcgcagccga gttgttaggc gtcagccctc acaccttgcg   8700
cctgttcatc aaacgccgga acatcaaacc cacaaacact agaccaacca tcaccatgcc   8760
ggggagggaa caacatgcct aagaacaaca aagcccccgg ccatcgtatc aacgagatca   8820
tcaagacgag cctcgcgctc gaaatggagg atgcccgcga agctggctta gtcggctaca   8880
tggcccgttg ccttgtgcaa gcgaccatgc cccacaccga ccccaagacc agctactttg   8940
agcgcaccaa tggcatcgtc accttgtcga tcatgggcaa gccgagcatc ggcctgccct   9000
acggttctat gccgcgcacc ttgcttgctt ggatatgcac cgaggccgtg cgaacgaaag   9060
accccgtgtt gaaccttggc cggtcgcaat cggaatttct acaaaggctc ggaatgcaca   9120
ccgatggccg ttacacggcc acccttcgca atcaggcgca acgcctgttt tcatccatga   9180
tttcgcttgc cggcgagcaa ggcaatgact tcggcattga gaacgtcgtc attgccaagc   9240
gcgcttttct attctggaat cccaagcggc cagaagatcg ggcgctatgg gatagcaccc   9300
tcaccctcac aggcgatttc ttcgaggaag tcacccgctc accggttcct atccgaatcg   9360
actacctgca tgccttgcgg cagtctccgc ttgcgatgga catttacacg tggctgacct   9420
atcgcgtgtt cctgttgcgg gccaagggcc gcccctttcgt gcaaatccct tgggtcgccc   9480
tgcaagcgca attcggctca tcctatggca gccgcgcacg caactcgccc gaactggacg   9540
ataaggcccg agagcgggca gagcgggcag cactcgccag cttcaaatac aacttcaaaa   9600
agcgcctacg cgaagtgttg attgtctatc ccgaggcaag cgactgcatc gaagatgacg   9660
gcgaatgcct gcgcatcaaa tccacacgcc tgcatgtcac ccgcgcaccc ggcaagggcg   9720
ctcgcatcgg ccccccctccg acttgaccag gccaacgcta cgcttggctt ggtcaagcct   9780
tcccatccaa cagcccgccg tcgagcgggc ttttttatcc ccggaagcct gtggatagag   9840
ggtagttatc cacgtgaaac cgctaatgcc ccgcaaagcc ttgattcacg gggctttccg   9900
gcccgctcca aaaactatcc acgtgaaatc gctaatcagg gtacgtgaaa tcgctaatcg   9960
gagtacgtga aatcgctaat aaggtcacgt gaaatcgcta atcaaaaagg cacgtgagaa  10020
cgctaatagc cctttcagat caacagcttg caaacacccc tcgctccggc aagtagttac  10080
agcaagtagt atgttcaatt agcttttcaa ttatgaatat atatatcaat tattggtcgc  10140
ccttggcttg tggacaatgc gctacgcgca ccggctccgc ccgtggacaa ccgcaagcgg  10200
```

```
ttgcccaccg tcgagcgcct ttgcccacaa cccggcggcc gcaacagatc gttttataaa  10260
ttttttttt tgaaaaagaa aaagcccgaa aggcggcaac ctctcgggct tctggatttc  10320
cgatcaacgc aggagtcgtt cggaaagtag ctgttccaga attataggcg cagagacacc  10380
agattccaag atggctctgt taaattgttg tagtatgtag tatcatacaa catactacag  10440
tacagaggcc cgcaagaatg gcaatcacta aacaagacat ttggcgagca gccgacgaac  10500
tggacgccga aggcatccgg cccactttgg ccgccgtgcg caagaaactc ggaagcggta  10560
gcttcacaac catttccgat gcaatggctg aatggaaaaa ccgcaagacc gccaccctgc  10620
cctcatcaga cccattgccg gttgcagtca acgagcatct tgccgagctt ggcaatgcgc  10680
tatgggctat cgccctggcg cacgccaacg cccggtttga cgaagatcgg aaacagatcg  10740
aggccgacaa agcggccatc agccagcagc ttgccgaagc aatcgaacta gccgacacct  10800
tcacccgcga aaacgaccag ctccgcgaac gagtgaatca gctcgaacct atggaacgcg  10860
agcgcgacaa gctggccgac cagcttgccg aagtgaaacg ccgcagcggc gaagaactaa  10920
accgctgcat ggaaaagctc acccaacgcg ataacgaggc tatcgaggcc cgcaaacagg  10980
ccaaggaggc catcgagcgc gccgccagtc tgcaaggtca ggtggaagcc ctcaaagagc  11040
aggtcgccaa tctcacagcc gtcttgaaaa caggaggcaa acaatgaaaa gcgcccttgc  11100
cgcccttcgc gcggtcgcgg ccgctgtcgt cctaatcgtc agtgtgcccg cttgggccga  11160
cttccggggt gaagtcgtcc gaatccttga cggtgacact atcgacgttt tggtgaaccg  11220
tcagaccatc cgcgtgagat tggccgatat tgacgcaccg gaaagcggcc aagccttcgg  11280
ctcccgtgct cgccaacggc tcgccgactt gacctttcgc caagaggttc aagtgaccga  11340
aaaagaggtt gatcggtatg gccgcactct tggggtcgtt tacgcgccgt tgcaataccc  11400
cggcggccaa acacaactca ccaacatcaa tgcgatcatg gttcaagaag gcatggcctg  11460
ggcttaccgt tattacggca aaccaaccga cgcgcagatg tacgagtatg aaaaagaggc  11520
ccgccgccaa cggctcggcc tttggtcaga cccgaatgct caggagcctt ggaaatggcg  11580
tcgcgcctcg aaaaatgcca cgaactgaca ccgggcacgc cccttgttcg acgcgccgca  11640
ggcacgtcga atttaccgcc gggacgcccc tcgtcccgac acttccagat cgccatagcg  11700
cacagcgccg agtcacccga agggccgcaa cgtagtggag gacggcaacg ccgttgaacg  11760
gcgcgagcac tatggcacgc gaagcgagct tgacacgatg gaggaaagac catgaccgac  11820
acgcgccgcg agcaggagaa agacgaacgc cggaagctgc aagagcagtc gcgccagaat  11880
gaagcggaaa ccatgcgcct gctggctttc gaggcaggcc gccaattggc cgaaattccg  11940
aaagaagcca aaggcaatga acccttgctt gagaactaca agagcggact acaagagacc  12000
cgcaaagagc tagaaaccac gccagacgcc actaagagca ccaacgccaa ccggcttgag  12060
cgcgacgtag aaagggccat catcgaggcg caacaggtgc gcgaggcagt aggcagggag  12120
aaagcccgcg cagatgaatt tcaccgccac gcagaaccgg gcgaaactta ccggggccgt  12180
gtgatcggtc gcaccaatag ctatgtcatt caggccgacg atagccgccc aggcacgatc  12240
attctgcatg aacgcgccgc tgtttcgggc gcggagaaag tgaagatgaa cgaccatgcg  12300
gaaatcagtt atccgcacgg tcgcgccgga atcgtccgca acccacaggc cgcgcaacat  12360
caacgacagc ggcagatgga aaaaaccggc gcaggccgag agcatgggcg ctaacgatgc  12420
tgatgttgct acggcggcgg tgtcgcgctt ggctggaaat tcggcggctt gataaagagc  12480
ttgcgcagtc gagcgggttg cccctcgaat tgcctcaaat cgtgccgaat gcttggaatg  12540
```

```
aggttgtttg gcggctgccc gtgccgaacc atcctgacgc ctttatgaca gcttcaaatg  12600

ccgcacagtc cgatttcatt gtgtatgtga atggcttggc tttctatcga gcgtggttgg  12660

cgttaggcgt cgaggattct caagcctgcc cgttgaagca ggacatgcct aaagaccgga  12720

aatatccgtc gagcgccgcg cattttgccg tgggcatcga cagccccgtt ccgcttgctg  12780

acgtaagccc gaccatgatt ctgggccatt tcgcggtgtg tttcactgat ggcatgaccc  12840

gttcaatgtg gcttttggcc catgaggtcg ccgtgtttcc ggtgctttcc cgtgatgaag  12900

catccgccgt tatgttggca gaacacgtgg gcgtagcagg gccgctgatc gaccgccacg  12960

tttccgggga ctggggcgac gtggacgatg cgcagcgcga ggccaacgag gaagccgtga  13020

aggagtgcgg caccatcgtg tcggtttacc acccgcacgg tgtgcgagtg ctgatcgtga  13080

ccgatggcga ccgttcgcac acggtagcca tgctgcccca cgagtattga gccggagccg  13140

acgccgtgag cagaaagcac caacccaaga ccgaaaggca ggaaaaggcg gcagtcattg  13200

ccgcctcact gcccgaagat cggggcgagc tgatggacg                          13239
```

<210> SEQ ID NO 2
<211> LENGTH: 291
<212> TYPE: DNA
<213> ORGANISM: Artificial Sequence
<220> FEATURE:
<223> OTHER INFORMATION: Oligonucleotide top strand

<400> SEQUENCE: 2

```
ggggtacccg ctacccgggt catgatgtct aacgtttgac atgaggggcg gccaagggcg     60

ccagcccttg gacgtccccc tcgatggaag ggttaggcat cactgcgtgt tcgctcgaat    120

gcctggcgtg tttgaaccat gtacacggct ggaccatctg ggtggttac agtaccttgc     180

ctctcaaacc ccgctttctc gtagcatcgg atcgctcgca agttgctcgg cgacgggtcc    240

gtttggatct tggtgacttc gggatcattg aacagcaact caaccagagc t             291
```

<210> SEQ ID NO 3
<211> LENGTH: 289
<212> TYPE: DNA
<213> ORGANISM: Artificial Sequence
<220> FEATURE:
<223> OTHER INFORMATION: Oligonucleotide bottom strand

<400> SEQUENCE: 3

```
ctggttgagt tgctgttcaa tgatcccgaa gtcaccaaga tccaaacgga cccgtcgccg     60

agcaacttgc gagcgatccg atgctacgag aaagcggggt ttgagaggca aggtactgta    120

accaccccag atggtccagc cgtgtacatg gttcaaacac gccaggcatt cgagcgaaca    180

cgcagtgatg cctaaccctt ccatcgaggg ggacgtccaa gggctggcgc ccttggccgc    240

ccctcatgtc aaacgttaga catcatgacc cgggtagcgg gtaccccgc               289
```

<210> SEQ ID NO 4
<211> LENGTH: 10466
<212> TYPE: DNA
<213> ORGANISM: Artificial Sequence
<220> FEATURE:
<223> OTHER INFORMATION: Plasmid pDAB9291

<400> SEQUENCE: 4

```
ccgcggggta cccgctaccc gggtcatgat gtctaacgtt tgacatgagg ggcggccaag     60

ggcgccagcc cttggacgtc cccctcgatg gaagggttag gcatcactgc gtgttcgctc    120

gaatgcctgg cgtgtttgaa ccatgtacac ggctggacca tctggggtgg ttacagtacc    180
```

```
ttgcctctca aaccccgctt tctcgtagca tcggatcgct cgcaagttgc tcggcgacgg    240
gtccgtttgg atcttggtga cttcgggatc attgaacagc aactcaacca gagctcgaac    300
cagcttggtt cccaagcctt tgcccagttg tgatgcattc gccagtgact ggtctattcc    360
gcgtactcct ggatcggttt cttcttccca ccatccgtcc ccgcttccaa gagcaacgta    420
cgactgggca tacccaatcg gctctccatt cagcattgca atgtatggag tgacggactc    480
ttgcgctaaa acgcttggca agtactgttc ctgtacgtca gcaagtgtcg ggcgtgcttc    540
ttctccgccc caccactcga cgatatgaga tcgatttagc cactcataga gcatcgcaag    600
gtcatgctca gtcatgaggc gcagtgtgac ggaatcggtg ctgttggtca cgatgctgta    660
ctttgtgatg cctaactttg ttttagggcg actgccctgc tgcgtaacat cgttgctgct    720
ccataacatc aaacatcgac ccacggcgta acgcgcttgc tgcttggatg cccgaggcat    780
agactgtaca aaaaaacagt cataacaagc catgaaaacc gccactgcgc cgttaccacc    840
gctgcgttcg gtcaaggttc tggaccagtt gcgtgagcgc atacgctact tgcattacag    900
tttacgaacc gaacaggctt atgtcaactg ggttcgtgcc ttcatccgtt tccacggtgt    960
gcgtcacccg gcaaccttgg gcagcagcga agtcgaggca tttctgtcct ggctggcgaa   1020
cgagcgcaag gtttcggtct ccacgcatcg tcaggcattg gcggccttgc tgttcttcta   1080
cggcaaggtg ctgtgcacgg atctgccctg gcttcaggag atcggaagac ctcggccgtc   1140
gcggcgcttg ccggtggtgc tgaccccgga tgaagtggtt cgcatcctcg gttttctgga   1200
aggcgagcat cgtttgttcg cccagcttct gtatggaacg ggcatgcgga tcagtgaggg   1260
tttgcaactg cgggtcaagg atctggattt cgatcacggc acgatcatcg tgcgggaggg   1320
caagggctcc aaggatcggg ccttgatgtt acccgagagc ttggcaccca gcctgcgcga   1380
gcagctgcct cgcgcgtttc ggtgatgacg gtgaaaacct ctgacacatg cagctcccgg   1440
agacggtcac agcttgtctg taagcggatg ccgggagcag acaagcccgt cagggcgcgt   1500
cagcgggtgt tggcgggtgt cggggcgcag ccatgaccca gtcacgtagc gatagcggag   1560
tgtatactgg cttaactatg cggcatcaga gcagattgta ctgagagtgc accatatgcg   1620
gtgtgaaata ccgcacagat gcgtaaggag aaaataccgc atcaggcgct cttccgcttc   1680
ctcgctcact gactcgctgc gctcggtcgt tcggctgcgg cgagcggtat cagctcactc   1740
aaaggcggta atacggttat ccacagaatc aggggataac gcaggaaaga acatgtgagc   1800
aaaaggccag caaaaggcca ggaaccgtaa aaaggccgcg ttgctggcgt ttttccatag   1860
gctccgcccc cctgacgagc atcacaaaaa tcgacgctca agtcagaggt ggcgaaaccc   1920
gacaggacta taaagatacc aggcgtttcc ccctggaagc tccctcgtgc gctctcctgt   1980
tccgaccctg ccgcttaccg gatacctgtc cgcctttctc ccttcgggaa gcgtggcgct   2040
ttctcatagc tcacgctgta ggtatctcag ttcggtgtag gtcgttcgct ccaagctggg   2100
ctgtgtgcac gaaccccccg ttcagcccga ccgctgcgcc ttatccggta actatcgtct   2160
tgagtccaac ccggtaagac acgacttatc gccactggca gcagccactg gtaacaggat   2220
tagcagagcg aggtatgtag gcggtgctac agagttcttg aagtggtggc ctaactacgg   2280
ctacactaga aggacagtat ttggtatctg cgctctgctg aagccagtta ccttcggaaa   2340
aagagttggt agctcttgat ccggcaaaca aaccaccgct ggtagcggtg gtttttttgt   2400
ttgcaagcag cagattacgc gcagaaaaaa aggatctcaa gaagatcctt tgatcttttc   2460
tacggggtct gacgctcagt ggaacgaaaa ctcacgttaa gggattttgg tcatgagatt   2520
```

```
atcaaaaagg atcttcacct agatcctttt aaattaaaaa tgaagtttta aatcaatcta   2580
aagtatatat gagtaaactt ggtctgacag ttaccaatgc ttaatcagtg aggcacctat   2640
ctcagcgatc tgtctatttc gttcatccat agttgcctga ctccccgtcg tgtagataac   2700
tacgatacgg gagggcttac catctggccc cagtgctgca atgataccgc gagacccacg   2760
ctcaccggct ccagatttat cagcaataaa ccagccagcc ggaagggccg agcgcagaag   2820
tggtcctgca actttatccg cctccatcca gtctattaat tgttgccggg aagctagagt   2880
aagtagttcg ccagttaata gtttgcgcaa cgttgttgcc attgctgccc ttgagagcct   2940
tcaacccagt cagctccttc cggtgggcgc ggggcatgac tatcgtcgcc gcacttatga   3000
ctgtcttctt tatcatgcaa ctcgtaggac aggtgccggc agcgctctgg gtcattttcg   3060
gcgaggaccg ctttcgctgg agcgcgacga tgatcggcct gtcgcttgcg gtattcggaa   3120
tcttgcacgc cctcgctcaa gccttcgtca ctggtcccgc caccaaacgt ttcggcgaga   3180
agcaggccat tatcgccggc atggcggccg acgcgctggg ctacgtcttg ctggcgttcg   3240
cgacgcgagg ctggatggcc ttccccatta tgattcttct cgcttccggc ggcatcggga   3300
tgcccgcgtt gcaggccatg ctgtccaggc aggtagatga cgaccatcag ggacagcttc   3360
aaggatcgct cgcggctctt accagcctaa cttcgatcat tggaccgctg atcgtcacgg   3420
cgatttatgc cgcctcggcg agcacatgga acgggttggc atggattgta ggcgccgccc   3480
tataccttgt ctgcctcccc gcgttgcgtc gcggtgcatg gagccgggcc acctcgacct   3540
gaatggaagc cggcggcacc tcgctaacgg attcaccact ccaagaattg gagccaatca   3600
attcttgcgg agaactgtga atgcgcaaac caacccttgg cagaacatat ccatcgcgtc   3660
cgccatctcc agcagccgca cgcggcgcat ctcgggcagc gttgggtcct ggccacgggt   3720
gcgcatgatc gtgctcctgt cgttgaggac ccggctaggc tggcggggtt gccttactgg   3780
ttagcagaat gaatcaccga tacgcgagcg aacgtgaagc gactgctgct gcaaaacgtc   3840
tgcgacctga gcaacaacat gaatggtctt cggtttccgt gtttcgtaaa gtctggaaac   3900
gcggaagtca gcgccctgca ccattatgtt ccggatctgc atcgcaggat gctgctggct   3960
accctgtgga acacctacat ctgtattaac gaagcgctgg cattgaccct gagtgatttt   4020
tctctggtcc cgccgcatcc ataccgccag ttgtttaccc tcacaacgtt ccagtaaccg   4080
ggcatgttca tcatcagtaa cccgtatcgt gagcatcctc tctcgtttca tcggtatcat   4140
tacccccatg aacagaaatc ccccttacac ggaggcatca gtgaccaaac aggaaaaaac   4200
cgcccttaac atggcccgct ttatcagaag ccagacatta acgcttctgg agaaactcaa   4260
cgagctggac gcggatgaac aggcagacat ctgtgaatcg cttcacgacc acgctgatga   4320
gctttgtcgc gtgcacgggc atggtggctg aaggaccagg ccgagggccg cagcggcgtt   4380
gcgcttcccg acgcccttga gcggaagtat ccgcgcgccg ggcattcctg gccgtggttc   4440
tgggtttttg cgcagcacac gcattcgacc gatccacgga gcggtgtcgt gcgtcgccat   4500
cacatgtatg accagacctt tcagcgcgcc ttcaaacgtg ccgtagaaca agcaggcatc   4560
acgaagcccg ccacaccgca caccctccgc cactcgttcg cgacggcctt gctccgcagc   4620
ggttacgaca ttcgaaccgt gcaggatctg ctcggccatt ccgacgtctc tacgacgatg   4680
atttacacgc atgtgctgaa agttggcggt gccggagtgc gctcaccgct tgatgcgctg   4740
ccgcccctca ctagtgagag gtagggcagc gcaagtcaat cctggcggat tcactacccc   4800
tgcgcgaagg ccatcggtgc cgcatcgaac ggccggttgc ggaaagtcct ccctgcgtcc   4860
gctgatggcc ggcagcagcc cgtcgttgcc tgatggatcc aacccctccg ctgctatagt   4920
```

```
gcagtcggct tctgacgttc agtgcagccg tcttctgaaa acgacatctg gtgttcctca   4980
ttctctggtg gctgcgcggc ccggtgcgct ttcttctcgg cttggcttcg ttcgccagtc   5040
tcatcaccct accgatcatg tggcttgggc tggactcggc caataagacc cacatcatgc   5100
tatcggtcgc aggcgtcggc cttggtgcgt cggccctcat gtggttttat gacgcgcttc   5160
tcatgaggct ggcaccagaa ccaatcctat tcagcaccta aacgaaggcc gggccactca   5220
cccggccttt tttgtacgct catagggcag aacaaaccaa cgttttatct ataccgcaac   5280
agggtattta attcctattt aatctgcgct agaatgaggc atgtttaacc gaatctgacg   5340
ttttccctgc aaatgccaaa atactatgcc tatctccggg tttcgcgtga cggccaagac   5400
ccggaaaacc aaaaatacgg tttgctcgaa tacgcgaacg ccaaaggctt cgcgccgcta   5460
cagatcgagg aagaaattgc cagcagagca aaggactggc gcaagcgcaa gctcggagca   5520
atcatcgaaa aggccgagcg tggcgacgtg ctactgacgc cggagattac gcgcattgcc   5580
ggttccgccc tcgccgcctt ggaaattctc aaagcggcga gcgagcgcgg cctaatcgtc   5640
catgtgacca aacagaagat catcatggac ggcagcctac aaagcgacat catggcaacc   5700
gtgcttggct tggctgcaca gatcgagcgg catttcattc aggcacgtac caccgaggcg   5760
ctacaagtcg ccagagagcg cggcaagacg ctcgggcgac ccaagggcag caaatcgagc   5820
gccttgaagc tggacagccg tattgatgaa gtacaggcat acgtgaacct tggcttgccg   5880
caaagtcgcg cagccgagtt gttaggcgtc agccctcaca ccttgcgcct gttcatcaaa   5940
cgccggaaca tcaaacccac aaacactaga ccaaccatca ccatgccggg gagggaacaa   6000
catgcctaag aacaacaaag cccccggcca tcgtatcaac gagatcatca agacgagcct   6060
cgcgctcgaa atggaggatg cccgcgaagc tggcttagtc ggctacatgg cccgttgcct   6120
tgtgcaagcg accatgcccc acaccgaccc caagaccagc tactttgagc gcaccaatgg   6180
catcgtcacc ttgtcgatca tgggcaagcc gagcatcggc ctgccctacg gttctatgcc   6240
gcgcaccttg cttgcttgga tatgcaccga ggccgtgcga acgaaagacc ccgtgttgaa   6300
ccttggccgg tcgcaatcgg aatttctaca aaggctcgga atgcacaccg atggccgtta   6360
cacggccacc cttcgcaatc aggcgcaacg cctgttttca tccatgattt cgcttgccgg   6420
cgagcaaggc aatgacttcg gcattgagaa cgtcgtcatt gccaagcgcg cttttctatt   6480
ctggaatccc aagcggccag aagatcgggc gctatgggat agcaccctca ccctcacagg   6540
cgatttcttc gaggaagtca cccgctcacc ggttcctatc cgaatcgact acctgcatgc   6600
cttgcggcag tctccgcttg cgatggacat ttacacgtgg ctgacctatc gcgtgttcct   6660
gttgcgggcc aagggccgcc ccttcgtgca aatcccttgg gtcgccctgc aagcgcaatt   6720
cggctcatcc tatggcagcc gcgcacgcaa ctcgcccgaa ctggacgata aggcccgaga   6780
gcgggcagag cgggcagcac tcgccagctt caaatacaac ttcaaaaagc gcctacgcga   6840
agtgttgatt gtctatcccg aggcaagcga ctgcatcgaa gatgacggcg aatgcctgcg   6900
catcaaatcc acacgcctgc atgtcacccg cgcacccggc aagggcgctc gcatcggccc   6960
ccctccgact tgaccaggcc aacgctacgc ttggcttggt caagccttcc catccaacag   7020
cccgccgtcg agcgggcttt tttatccccg gaagcctgtg gatagagggt agttatccac   7080
gtgaaaccgc taatgccccg caaagccttg attcacgggg ctttccggcc cgctccaaaa   7140
actatccacg tgaaatcgct aatcagggta cgtgaaatcg ctaatcggag tacgtgaaat   7200
cgctaataag gtcacgtgaa atcgctaatc aaaaaggcac gtgagaacgc taatagccct   7260
```

```
ttcagatcaa cagcttgcaa acacccctcg ctccggcaag tagttacagc aagtagtatg   7320
ttcaattagc ttttcaatta tgaatatata tatcaattat tggtcgccct tggcttgtgg   7380
acaatgcgct acgcgcaccg gctccgcccg tggacaaccg caagcggttg cccaccgtcg   7440
agcgcctttg cccacaaccc ggcggccgca acagatcgtt ttataaattt tttttttga    7500
aaaagaaaaa gcccgaaagg cggcaacctc tcgggcttct ggatttccga tcaacgcagg   7560
agtcgttcgg aaagtagctg ttccagaatt ataggcgcag agacaccaga ttccaagatg   7620
gctctgttaa attgttgtag tatgtagtat catacaacat actacagtac agaggcccgc   7680
aagaatggca atcactaaac aagacatttg gcgagcagcc gacgaactgg acgccgaagg   7740
catccggccc actttggccg ccgtgcgcaa gaaactcgga agcggtagct tcacaaccat   7800
ttccgatgca atggctgaat ggaaaaaccg caagaccgcc accctgccct catcagaccc   7860
attgccggtt gcagtcaacg agcatcttgc cgagcttggc aatgcgctat gggctatcgc   7920
cctggcgcac gccaacgccc ggtttgacga agatcggaaa cagatcgagg ccgacaaagc   7980
ggccatcagc cagcagcttg ccgaagcaat cgaactagcc gacaccttca cccgcgaaaa   8040
cgaccagctc cgcgaacgag tgaatcagct cgaacctatg gaacgcgagc gcgacaagct   8100
ggccgaccag cttgccgaag tgaaacgccg cagcggcgaa gaactaaacc gctgcatgga   8160
aaagctcacc caacgcgata acgaggctat cgaggcccgc aaacaggcca aggaggccat   8220
cgagcgcgcc gccagtctgc aaggtcaggt ggaagccctc aaagagcagg tcgccaatct   8280
cacagccgtc ttgaaaacag gaggcaaaca atgaaaagcg cccttgccgc ccttcgcgcg   8340
gtcgcggccg ctgtcgtcct aatcgtcagt gtgcccgctt gggccgactt ccggggtgaa   8400
gtcgtccgaa tccttgacgg tgacactatc gacgttttgg tgaaccgtca gaccatccgc   8460
gtgagattgg ccgatattga cgcaccggaa agcggccaag ccttcggctc ccgtgctcgc   8520
caacggctcg ccgacttgac ctttcgccaa gaggttcaag tgaccgaaaa agaggttgat   8580
cggtatggcc gcactcttgg ggtcgtttac gcgccgttgc aataccccgg cggccaaaca   8640
caactcacca acatcaatgc gatcatggtt caagaaggca tggcctgggc ttaccgttat   8700
tacggcaaac caaccgacgc gcagatgtac gagtatgaaa aagaggcccg ccgccaacgg   8760
ctcggccttt ggtcagaccc gaatgctcag gagccttgga aatggcgtcg cgcctcgaaa   8820
aatgccacga actgacaccg ggcacgcccc ttgttcgacg cgccgcaggc acgtcgaatt   8880
taccgccggg acgcccctcg tcccgacact tccagatcgc catagcgcac agcgccgagt   8940
cacccgaagg gccgcaacgt agtggaggac ggcaacgccg ttgaacggcg cgagcactat   9000
ggcacgcgaa gcgagcttga cacgatggag gaaagaccat gaccgacacg cgccgcgagc   9060
aggagaaaga cgaacgccgg aagctgcaag agcagtcgcg ccagaatgaa gcggaaacca   9120
tgcgcctgct ggctttcgag gcaggccgcc aattggccga aattccgaaa gaagccaaag   9180
gcaatgaacc cttgcttgag aactacaaga gcggactaca agagacccgc aaagagctag   9240
aaaccacgcc agacgccact aagagcacca acgccaaccg gcttgagcgc gacgtagaaa   9300
gggccatcat cgaggcgcaa caggtgcgcg aggcagtagg cagggagaaa gcccgcgcag   9360
atgaatttca ccgccacgca gaaccgggcg aaacttaccg gggccgtgtg atcggtcgca   9420
ccaatagcta tgtcattcag gccgacgata gccgcccagg cacgatcatt ctgcatgaac   9480
gcgccgctgt ttcgggcgcg gagaaagtga agatgaacga ccatgcggaa atcagttatc   9540
cgcacggtcg cgccggaatc gtccgcaacc cacaggccgc gcaacatcaa cgacagcggc   9600
agatggaaaa aaccggcgca ggccgagagc atgggcgcta acgatgctga tgttgctacg   9660
```

```
gcggcggtgt cgcgcttggc tggaaattcg gcggcttgat aaagagcttg cgcagtcgag   9720

cgggttgccc ctcgaattgc ctcaaatcgt gccgaatgct tggaatgagg ttgtttggcg   9780

gctgcccgtg ccgaaccatc ctgacgcctt tatgacagct tcaaatgccg cacagtccga   9840

tttcattgtg tatgtgaatg gcttggcttt ctatcgagcg tggttggcgt taggcgtcga   9900

ggattctcaa gcctgcccgt tgaagcagga catgcctaaa gaccggaaat atccgtcgag   9960

cgccgcgcat tttgccgtgg gcatcgacag ccccgttccg cttgctgacg taagcccgac  10020

catgattctg ggccatttcg cggtgtgttt cactgatggc atgacccgtt caatgtggct  10080

tttggcccat gaggtcgccg tgtttccggt gctttcccgt gatgaagcat ccgccgttat  10140

gttggcagaa cacgtgggcg tagcagggcc gctgatcgac cgccacgttt ccggggactg  10200

gggcgacgtg gacgatgcgc agcgcgaggc caacgaggaa gccgtgaagg agtgcggcac  10260

catcgtgtcg gtttaccacc cgcacggtgt gcgagtgctg atcgtgaccg atggcgaccg  10320

ttcgcacacg gtagccatgc tgccccacga gtattgagcc ggagccgacg ccgtgagcag  10380

aaagcaccaa cccaagaccg aaaggcagga aaaggcggca gtcattgccg cctcactgcc  10440

cgaagatcgg ggcgagctga tggacg                                       10466
```

```
<210> SEQ ID NO 5
<211> LENGTH: 25275
<212> TYPE: DNA
<213> ORGANISM: Artificial Sequence
<220> FEATURE:
<223> OTHER INFORMATION: Plasmid pDAB9292

<400> SEQUENCE: 5

ggtacccgct acccgggtca tgatgtctaa cgtttgacat gaggggcggc caagggcgcc     60

agcccttgga cgtcccccctc gatggaaggg ttaggcatca ctgcgtgttc gctcgaatgc    120

ctggcgtgtt tgaaccatgt acacggctgg accatctggg gtggttacag taccttgcct    180

ctcaaacccc gctttctcgt agcatcggat cgctcgcaag ttgctcggcg acgggtccgt    240

ttggatcttg gtgacttcgg gatcattgaa cagcaactca accagagctc gaaccagctt    300

ggttcccaag cctttgccca gttgtgatgc attcgccagt gactggtcta ttccgcgtac    360

tcctggatcg gtttcttctt cccaccatcc gtccccgctt ccaagagcaa cgtacgactg    420

ggcataccca atcggctctc cattcagcat tgcaatgtat ggagtgacgg actcttgcgc    480

taaaacgctt ggcaagtact gttcctgtac gtcagcaagt gtcgggcgtg cttcttctcc    540

gccccaccac tcgacgatat gagatcgatt tagccactca tagagcatcg caaggtcatg    600

ctcagtcatg aggcgcagtg tgacggaatc ggtgctgttg gtcacgatgc tgtactttgt    660

gatgcctaac tttgttttag ggcgactgcc ctgctgcgta acatcgttgc tgctccataa    720

catcaaacat cgacccacgg cgtaacgcgc ttgctgcttg gatgcccgag gcatagactg    780

tacaaaaaaa cagtcataac aagccatgaa aaccgccact gcgccgttac caccgctgcg    840

ttcggtcaag gttctggacc agttgcgtga gcgcatacgc tacttgcatt acagtttacg    900

aaccgaacag gcttatgtca actgggttcg tgccttcatc cgtttccacg gtgtgcgtca    960

cccggcaacc ttgggcagca gcgaagtcga ggcatttctg tcctggctgg cgaacgagcg   1020

caaggtttcg gtctccacgc atcgtcaggc attggcggcc ttgctgttct tctacggcaa   1080

ggtgctgtgc acggatctgc cctggcttca ggagatcgga agacctcggc cgtcgcggcg   1140

cttgccggtg gtgctgaccc cggatgaagt ggttcgcatc ctcggttttc tggaaggcga   1200
```

-continued

```
gcatcgtttg ttcgcccagc ttctgtatgg aacgggcatg cggatcagtg agggtttgca   1260
actgcgggtc aaggatctgg atttcgatca cggcacgatc atcgtgcggg agggcaaggg   1320
ctccaaggat cgggccttga tgttacccga gagcttggca cccagcctgc gcgagcagct   1380
gcctcgcgcg tttcggtgat gacggtgaaa acctctgaca catgcagctc ccggagacgg   1440
tcacagcttg tctgtaagcg gatgccggga gcagacaagc ccgtcagggc gcgtcagcgg   1500
gtgttggcgg gtgtcggggc gcagccatga cccagtcacg tagcgatagc ggagtgtata   1560
ctggcttaac tatgcggcat cagagcagat tgtactgaga gtgcaccata tgcggtgtga   1620
aataccgcac agatgcgtaa ggagaaaata ccgcatcagg cgctcttccg cttcctcgct   1680
cactgactcg ctgcgctcgg tcgttcggct gcggcgagcg gtatcagctc actcaaaggc   1740
ggtaatacgg ttatccacag aatcagggga taacgcagga aagaacatgt gagcaaaagg   1800
ccagcaaaag gccaggaacc gtaaaaaggc cgcgttgctg gcgtttttcc ataggctccg   1860
ccccctgac gagcatcaca aaaatcgacg ctcaagtcag aggtggcgaa acccgacagg   1920
actataaaga taccaggcgt ttccccctgg aagctccctc gtgcgctctc ctgttccgac   1980
cctgccgctt accggatacc tgtccgcctt tctcccttcg ggaagcgtgg cgctttctca   2040
tagctcacgc tgtaggtatc tcagttcggt gtaggtcgtt cgctccaagc tgggctgtgt   2100
gcacgaaccc cccgttcagc ccgaccgctg cgccttatcc ggtaactatc gtcttgagtc   2160
caacccggta agacacgact tatcgccact ggcagcagcc actggtaaca ggattagcag   2220
agcgaggtat gtaggcggtg ctacagagtt cttgaagtgg tggcctaact acggctacac   2280
tagaaggaca gtatttggta tctgcgctct gctgaagcca gttaccttcg gaaaaagagt   2340
tggtagctct tgatccggca aacaaaccac cgctggtagc ggtggttttt ttgtttgcaa   2400
gcagcagatt acgcgcagaa aaaaaggatc tcaagaagat cctttgatct tttctacggg   2460
gtctgacgct cagtggaacg aaaactcacg ttaagggatt ttggtcatga gattatcaaa   2520
aaggatcttc acctagatcc ttttaaatta aaaatgaagt tttaaatcaa tctaaagtat   2580
atatgagtaa acttggtctg acagttacca atgcttaatc agtgaggcac ctatctcagc   2640
gatctgtcta tttcgttcat ccatagttgc ctgactcccc gtcgtgtaga taactacgat   2700
acgggagggc ttaccatctg gccccagtgc tgcaatgata ccgcgagacc cacgctcacc   2760
ggctccagat ttatcagcaa taaaccagcc agccggaagg gccgagcgca gaagtggtcc   2820
tgcaacttta tccgcctcca tccagtctat taattgttgc cgggaagcta gagtaagtag   2880
ttcgccagtt aatagtttgc gcaacgttgt tgccattgct gcccttgaga gccttcaacc   2940
cagtcagctc cttccggtgg gcgcggggca tgactatcgt cgccgcactt atgactgtct   3000
tctttatcat gcaactcgta ggacaggtgc cggcagcgct ctgggtcatt ttcggcgagg   3060
accgctttcg ctggagcgcg acgatgatcg gcctgtcgct tgcggtattc ggaatcttgc   3120
acgccctcgc tcaagccttc gtcactggtc ccgccaccaa acgtttcggc gagaagcagg   3180
ccattatcgc cggcatggcg gccgacgcgc tgggctacgt cttgctggcg ttcgcgacgc   3240
gaggctggat ggccttcccc attatgattc ttctcgcttc cggcggcatc gggatgcccg   3300
cgttgcaggc catgctgtcc aggcaggtag atgacgacca tcagggacag cttcaaggat   3360
cgctcgcggc tcttaccagc ctaacttcga tcattggacc gctgatcgtc acggcgattt   3420
atgccgcctc ggcgagcaca tggaacgggt tggcatggat tgtaggcgcc gccctatacc   3480
ttgtctgcct ccccgcgttg cgtcgcggtg catggagccg ggccacctcg acctgaatgg   3540
aagccggcgg cacctcgcta acggattcac cactccaaga attggagcca atcaattctt   3600
```

```
gcggagaact gtgaatgcgc aaaccaaccc ttggcagaac atatccatcg cgtccgccat   3660
ctccagcagc cgcacgcggc gcatctcggg cagcgttggg tcctggccac gggtgcgcat   3720
gatcgtgctc ctgtcgttga ggacccggct aggctggcgg ggttgcctta ctggttagca   3780
gaatgaatca ccgatacgcg agcgaacgtg aagcgactgc tgctgcaaaa cgtctgcgac   3840
ctgagcaaca acatgaatgg tcttcggttt ccgtgtttcg taaagtctgg aaacgcggaa   3900
gtcagcgccc tgcaccatta tgttccggat ctgcatcgca ggatgctgct ggctaccctg   3960
tggaacacct acatctgtat taacgaagcg ctggcattga ccctgagtga tttttctctg   4020
gtcccgccgc atccataccg ccagttgttt accctcacaa cgttccagta accgggcatg   4080
ttcatcatca gtaacccgta tcgtgagcat cctctctcgt ttcatcggta tcattacccc   4140
catgaacaga aatcccccctt acacggaggc atcagtgacc aaacaggaaa aaaccgccct   4200
taacatggcc cgctttatca gaagccagac attaacgctt ctggagaaac tcaacgagct   4260
ggacgcggat gaacaggcag acatctgtga atcgcttcac gaccacgctg atgagctttg   4320
tcgcgtgcac gggcatggtg gctgaaggac caggccgagg gccgcagcgg cgttgcgctt   4380
cccgacgccc ttgagcggaa gtatccgcgc gccgggcatt cctggccgtg gttctgggtt   4440
tttgcgcagc acacgcattc gaccgatcca cggagcggtg tcgtgcgtcg ccatcacatg   4500
tatgaccaga cctttcagcg cgccttcaaa cgtgccgtag aacaagcagg catcacgaag   4560
cccgccacac cgcacaccct ccgccactcg ttcgcgacgg ccttgctccg cagcggttac   4620
gacattcgaa ccgtgcagga tctgctcggc cattccgacg tctctacgac gatgatttac   4680
acgcatgtgc tgaaagttgg cggtgccgga gtgcgctcac cgcttgatgc gctgccgccc   4740
ctcactagtg agaggtaggg cagcgcaagt caatcctggc ggattcacta cccctgcgcg   4800
aaggccatcg gtgccgcatc gaacggccgg ttgcggaaag tcctccctgc gtccgctgat   4860
ggccggcagc agcccgtcgt tgcctgatgg atccaacccc tccgctgcta tagtgcagtc   4920
ggcttctgac gttcagtgca gccgtcttct gaaaacgaca tctggtgttc ctcattctct   4980
ggtggctgcg cggcccggtg cgctttcttc tcggcttggc ttcgttcgcc agtctcatca   5040
ccctaccgat catgtggctt gggctggact cggccaataa gacccacatc atgctatcgg   5100
tcgcaggcgt cggccttggt gcgtcggccc tcatgtggtt ttatgacgcg cttctcatga   5160
ggctggcacc agaaccaatc ctattcagca cctaaacgaa ggccgggcca ctcacccggc   5220
ctttttgta cgctcatagg gcagaacaaa ccaacgtttt atctataccg caacagggta   5280
tttaattcct atttaatctg cgctagaatg aggcatgttt aaccgaatct gacgttttcc   5340
ctgcaaatgc caaaatacta tgcctatctc cgggtttcgc gtgacggcca agacccggaa   5400
aaccaaaaat acggtttgct cgaatacgcg aacgccaaag gcttcgcgcc gctacagatc   5460
gaggaagaaa ttgccagcag agcaaaggac tggcgcaagc gcaagctcgg agcaatcatc   5520
gaaaaggccg agcgtggcga cgtgctactg acgccggaga ttacgcgcat tgccggttcc   5580
gccctcgccg ccttggaaat tctcaaagcg gcgagcgagc gcggcctaat cgtccatgtg   5640
accaaacaga agatcatcat ggacggcagc ctacaaagcg acatcatggc aaccgtgctt   5700
ggcttggctg cacagatcga gcggcatttc attcaggcac gtaccaccga ggcgctacaa   5760
gtcgccagag agcgcggcaa gacgctcggg cgacccaagg gcagcaaatc gagcgccttg   5820
aagctggaca gccgtattga tgaagtacag gcatacgtga accttggctt gccgcaaagt   5880
cgcgcagccg agttgttagg cgtcagccct cacaccttgc gcctgttcat caaacgccgg   5940
```

```
aacatcaaac ccacaaacac tagaccaacc atcaccatgc cggggaggga acaacatgcc   6000
taagaacaac aaagcccccg gccatcgtat caacgagatc atcaagacga gcctcgcgct   6060
cgaaatggag gatgcccgcg aagctggctt agtcggctac atggcccgtt gccttgtgca   6120
agcgaccatg ccccacaccg accccaagac cagctacttt gagcgcacca atggcatcgt   6180
caccttgtcg atcatgggca agccgagcat cggcctgccc tacggttcta tgccgcgcac   6240
cttgcttgct tggatatgca ccgaggccgt gcgaacgaaa gaccccgtgt tgaaccttgg   6300
ccggtcgcaa tcggaatttc tacaaaggct cggaatgcac accgatggcc gttacacggc   6360
caccccttcgc aatcaggcgc aacgcctgtt ttcatccatg atttcgcttg ccggcgagca   6420
aggcaatgac ttcggcattg agaacgtcgt cattgccaag cgcgcttttc tattctggaa   6480
tcccaagcgg ccagaagatc gggcgctatg ggatagcacc ctcaccctca caggcgattt   6540
cttcgaggaa gtcacccgct caccggttcc tatccgaatc gactacctgc atgccttgcg   6600
gcagtctccg cttgcgatgg acatttacac gtggctgacc tatcgcgtgt tcctgttgcg   6660
ggccaagggc cgcccccttcg tgcaaatccc ttgggtcgcc ctgcaagcgc aattcggctc   6720
atcctatggc agccgcgcac gcaactcgcc cgaactggac gataaggccc gagagcgggc   6780
agagcgggca gcactcgcca gcttcaaata caacttcaaa aagcgcctac gcgaagtgtt   6840
gattgtctat cccgaggcaa gcgactgcat cgaagatgac ggcgaatgcc tgcgcatcaa   6900
atccacacgc ctgcatgtca cccgcgcacc cggcaagggc gctcgcatcg gcccccctcc   6960
gacttgacca ggccaacgct acgcttggct tggtcaagcc ttcccatcca acagcccgcc   7020
gtcgagcggg ctttttatc cccggaagcc tgtggataga gggtagttat ccacgtgaaa   7080
ccgctaatgc ccgcaaagc cttgattcac ggggctttcc ggcccgctcc aaaaactatc   7140
cacgtgaaat cgctaatcag ggtacgtgaa atcgctaatc ggagtacgtg aaatcgctaa   7200
taaggtcacg tgaaatcgct aatcaaaaag gcacgtgaga acgctaatag ccctttcaga   7260
tcaacagctt gcaaacaccc ctcgctccgg caagtagtta cagcaagtag tatgttcaat   7320
tagcttttca attatgaata tatatatcaa ttattggtcg cccttggctt gtggacaatg   7380
cgctacgcgc accggctccg cccgtggaca accgcaagcg gttgcccacc gtcgagcgcc   7440
tttgcccaca acccggcggc cgcaacagat cgttttataa attttttttt ttgaaaaaga   7500
aaaagcccga aaggcggcaa cctctcgggc ttctggattt ccgatcaacg caggagtcgt   7560
tcggaaagta gctgttccag aattataggc gcagagacac cagattccaa gatggctctg   7620
ttaaattgtt gtagtatgta gtatcataca acatactaca gtacagaggc ccgcaagaat   7680
ggcaatcact aaacaagaca tttggcgagc agccgacgaa ctggacgccg aaggcatccg   7740
gcccactttg gccgccgtgc gcaagaaact cggaagcggt agcttcacaa ccatttccga   7800
tgcaatggct gaatggaaaa accgcaagac cgccaccctg ccctcatcag acccattgcc   7860
ggttgcagtc aacgagcatc ttgccgagct tggcaatgcg ctatgggcta tcgccctggc   7920
gcacgccaac gcccggtttg acgaagatcg gaaacagatc gaggccgaca aagcggccat   7980
cagccagcag cttgccgaag caatcgaact agccgacacc ttcacccgcg aaaacgacca   8040
gctccgcgaa cgagtgaatc agctcgaacc tatggaacgc gagcgcgaca agctggccga   8100
ccagcttgcc gaagtgaaac gccgcagcgg cgaagaacta aaccgctgca tggaaaagct   8160
cacccaacgc gataacgagg ctatcgaggc ccgcaaacag gccaaggagg ccatcgagcg   8220
cgccgccagt ctgcaaggtc aggtggaagc cctcaaagag caggtcgcca atctcacagc   8280
cgtcttgaaa acaggaggca aacaatgaaa agcgcccttg ccgcccttcg cgcggtcgcg   8340
```

```
gccgctgtcg tcctaatcgt cagtgtgccc gcttgggccg acttccgggg tgaagtcgtc   8400
cgaatccttg acggtgacac tatcgacgtt ttggtgaacc gtcagaccat ccgcgtgaga   8460
ttggccgata ttgacgcacc ggaaagcggc caagccttcg gctcccgtgc tcgccaacgg   8520
ctcgccgact tgacctttcg ccaagaggtt caagtgaccg aaaaagaggt tgatcggtat   8580
ggccgcactc ttggggtcgt ttacgcgccg ttgcaatacc ccggcggcca aacacaactc   8640
accaacatca atgcgatcat ggttcaagaa ggcatggcct gggcttaccg ttattacggc   8700
aaaccaaccg acgcgcagat gtacgagtat gaaaaagagg cccgccgcca acggctcggc   8760
ctttggtcag acccgaatgc tcaggagcct tggaaatggc gtcgcgcctc gaaaaatgcc   8820
acgaactgac accgggcacg ccccttgttc gacgcgccgc aggcacgtcg aatttaccgc   8880
cgggacgccc ctcgtcccga cacttccaga tcgccatagc gcacagcgcc gagtcacccg   8940
aagggccgca acgtagtgga ggacggcaac gccgttgaac ggcgcgagca ctatggcacg   9000
cgaagcgagc ttgacacgat ggaggaaaga ccatgaccga cacgcgccgc gagcaggaga   9060
aagacgaacg ccggaagctg caagagcagt cgcgccagaa tgaagcggaa accatgcgcc   9120
tgctggcttt cgaggcaggc cgccaattgg ccgaaattcc gaaagaagcc aaaggcaatg   9180
aacccttgct tgagaactac aagagcggac tacaagagac ccgcaaagag ctagaaacca   9240
cgccagacgc cactaagagc accaacgcca accggcttga gcgcgacgta gaaagggcca   9300
tcatcgaggc gcaacaggtg cgcgaggcag taggcaggga gaaagcccgc gcagatgaat   9360
ttcaccgcca cgcagaaccg ggcgaaactt accggggccg tgtgatcggt cgcaccaata   9420
gctatgtcat tcaggccgac gatagccgcc caggcacgat cattctgcat gaacgcgccg   9480
ctgtttcggg cgcggagaaa gtgaagatga acgaccatgc ggaaatcagt tatccgcacg   9540
gtcgcgccgg aatcgtccgc aacccacagg ccgcgcaaca tcaacgacag cggcagatgg   9600
aaaaaaccgg cgcaggccga gagcatgggc gctaacgatg ctgatgttgc tacggcggcg   9660
gtgtcgcgct tggctggaaa ttcggcggct tgataaagag cttgcgcagt cgagcgggtt   9720
gcccctcgaa ttgcctcaaa tcgtgccgaa tgcttggaat gaggttgttt ggcggctgcc   9780
cgtgccgaac catcctgacg cctttatgac agcttcaaat gccgcacagt ccgatttcat   9840
tgtgtatgtg aatggcttgg ctttctatcg agcgtggttg gcgttaggcg tcgaggattc   9900
tcaagcctgc ccgttgaagc aggacatgcc taaagaccgg aaatatccgt cgagcgccgc   9960
gcattttgcc gtgggcatcg acagccccgt tccgcttgct gacgtaagcc cgaccatgat  10020
tctgggccat ttcgcggtgt gtttcactga tggcatgacc cgttcaatgt ggcttttggc  10080
ccatgaggtc gccgtgtttc cggtgctttc ccgtgatgaa gcatccgccg ttatgttggc  10140
agaacacgtg ggcgtagcag ggccgctgat cgaccgccac gtttccgggg actggggcga  10200
cgtggacgat gcgcagcgcg aggccaacga ggaagccgtg aaggagtgcg gcaccatcgt  10260
gtcggtttac cacccgcacg gtgtgcgagt gctgatcgtg accgatggcg accgttcgca  10320
cacggtagcc atgctgcccc acgagtattg agccggagcc gacgccgtga gcagaaagca  10380
ccaacccaag accgaaaggc aggaaaaggc ggcagtcatt gccgcctcac tgcccgaaga  10440
tcggggcgag ctgatggacg ccgcggggta cctatctgca gacggaaggg attcctgtca  10500
ttggcgtcag ttcacttcgg tatttctggt cggagcggtc cccaagcgaa actgctaagg  10560
atcttggtca cataatcgat gtctacacca agcatttcgg tgtgcagaat gttttacttg  10620
taggatattc tttcggcgcg gacgtcatgc cggcaagctt caataggctt acgcttgagc  10680
```

```
aaaaaaatcg ggttaagcaa atctctctct tggcattgtc acatcaagtc gactatgtcg  10740
tctcatttag ggctggctc caactcgaaa cggaaggtaa gggcggcaat cctctggatg  10800
atctcagatc cattgaccct gcaatcgtcc aatgcatgta cgggcgcgaa gaccgtaata  10860
atgcttgccc atctctccga cagaccggcg cagaggtgat aggcttcagc ggaggccatc  10920
actttgataa tgatttcaaa aaactgtcta cgcgcgtcgt ctcaggcctc gtggcacgcc  10980
taagtcatca gtaatcttta gttcctgcac cgctttagta ttgactggga tagcgacgcc  11040
tgtgatgcag acatcggata ttgtgtcgtt aagtaaaagg ccttcgtctg atcgcgagac  11100
tcgctagtgg ttttcaggtg agtgagatgt tttgccgcaa gttgcgctga gatcgcatct  11160
gcctgcggct gccgcacctc cagattggca gcaacaagat catccttcaa gggaagatgc  11220
ctataacgca tgtgttgacg actttcgcct cgtgaatgat ccggtctgtt cccgacagtg  11280
ggatgccgtc gcgatagagc aggctctcgc gccaggagga atttctccga tatgacttct  11340
ctccttctac gtgcccaaag cagcaacgaa atcatctatc gcggccaaaa gagcggtcat  11400
gtgaaagcac ccttgccagt caattccctg gccaaggtca gcacggcgat actgcgaggt  11460
gttgctacac cacggaggcg atctagaagg acgatttcat catttaggcc gcacactcat  11520
aaatcaggtt tgcaaatcgg tctgattttg attcattgag gcttgacttg gaggccactg  11580
ataacccgtc cccgctttga tgtcaccgat ttcgaatgga ctgttgttca gtcctttgtt  11640
cccaaataag ccgcgtcgcg tgccgcgcgt tgacgcgggt gatcaatgtc atcttgtggc  11700
gcttccggac gggcccgccc tgggcagacg ttcctgatcg atacggttcc tgtacaacct  11760
gctacaatcg ctttgtacga tggcgtgagg cagacgtctg ggatcatatt ctgagtgtga  11820
tttccaaggc tttcgataga atgtcgtcat gattgacagt tcctgtgtcc gcgtccacca  11880
acatgcggcg acgggaaaca gcgggatcaa gacgatggct gtatgggacg ttcccgtggc  11940
ggtttgacca ccaagattca cgctgttgtc gatgccgacg gttgaccgat ccgtcttgcg  12000
ctgacagcgg gtcaagccca tgaccgccgc atgaccgaaa catttttaca aataatcgct  12060
tagagtgcgt ttctgctggc ggacaaggca tatgatacca acgcgataag agcatttgca  12120
aagcgcaagc aggcatgggc caatattcct gccaagagca atcggaagga agcttcccgt  12180
tcatcgaatg ggtttacaga cagcgtaacc tcgccgagca ttttcgttct gagcctgacc  12240
tgaccaactg cggcctgaat aggtcgatcc ggttgcttag tcatggatgc gcggttctcg  12300
gtccatgttg cgttccaaga cgccgggcga ggtttctcgc ttcaattgaa atcataaaga  12360
agcaattgaa aattttcgag taaccgaccc tcccgataat cttcaacata aaacaacgca  12420
cttcttccaa cgggagaggc ggtgttagtt gcgagctaag gagataaggt atgcttaaga  12480
gatcggggtc gctttctctt gccttgatgg tctccttctg ttcgtcgagc cttgccacgc  12540
cactctcatc tgctgagttt gaccatgttg ctcgcaagtg tgccccatca gttgcgacat  12600
ctacgcttgc ggcgatagct aaggtggaga gtcgctttga tcctttagcg attcatgaca  12660
acacgaccgg cgaaacgctt cactggcaag atcacagcca agcaacccaa gtcgtcaggc  12720
accgtctcga tgcacggcat tcgctggatg ttggcctcat gcaaataaac tctcgaaatt  12780
tttctatgct cggtctgaca cctgacggtg cgctccaggc gtgcacatca ttatctgccg  12840
ctgcaaacat gctgaaaagt cgttatgcag gcggcgaaac gattgacgag aagcaatttg  12900
cgcttcgtcg ggcgatctcc gcttacaaca ccggtaattt catcggcggt tttgcaaacg  12960
gctacgtgcg aaaagttgaa acagctgctc aatcgctggt gcccgcgtta atcgagcctc  13020
caaaagacga tcacgaggcg ctaaaatccg aagagacgtg ggatgtttgg gggtcatatc  13080
```

```
agcgccgctc gcaggaggat ggcgctggcg gtttaatcgc tccgccaccg ccacaccagg  13140
acaacggcaa atccgcagac gacaatcaag tcttattcga cttatactaa ggaggtgcgc  13200
attgatgcga tgctttgaga gataccgttt acatctaaat cgcctctcgc tctcgaatgc  13260
gatgatgcgc gtgatatcga gctgcgcccc aagcttgtgc ggtgcaattg catggagcat  13320
ttcctcatcc ggacccgccg cagcgcaatc tgcgggtggc ggcactgacc ccgccacaat  13380
ggttaacaat atatgcacgt ttatccttgg tccgttcggc cagtcactcg ctgttctcgg  13440
cattgtcgct atcgggatct cctggatgtt cgggcgggct tcgcttgggc tggttgccgg  13500
cgtcgtcggc ggcattgtta tcatgtttgg ggcgagcttc ctcggccaaa cgctcactgg  13560
cggtagttga tggctgatcg tttggaagaa tcgacccttt acctcgcagc cacacggccc  13620
gcattgtttc ttggggtgcc actgacattg gcagggttat tcatgatgtt cgccggcttt  13680
gtcatcgtta tcgttcagaa cccgctctac gaagtcgttc tcgtgccgtt atggtttgca  13740
gcccggctca tcgtggagcg agactacaat gcggcgagcg tcgtcctgct atttttgcgg  13800
accgcgggaa gaagcattga tagtgcagtt tggggggcg ctactgttag cccaaatcca  13860
attagggttc ccccacgagg gagaggaatg gtgtgatgct cggcgcgagt ggaacgaccg  13920
aaagatccgg tgagatctat ctcccttata ttggccacct cagcgaccat atcgtccttc  13980
ttgaagacgg atcgatcatg accattgcga gaattgatgg cgttgcattc gagcttgagg  14040
aaactgaaat gcgcaatgcg cgttgtcgtg cgttcaacac gctgttgcgc aatatcgctg  14100
atgatcatgt gtcaatatat gctcacctcg tacgtcatgc cgacgtgcca tcatcggcgc  14160
cgcgacactt ccgtagtgtt ttcgccgcta gcctgaacga agcttttgaa cagcgcgtgc  14220
tctccggcca actcctccgc aatgaacact tccttacgtt gattgtctac ccacaggcgg  14280
ctttagggaa ggtaaagagg aggttcacca agctaagcgg aaaaagggaa aacgatctca  14340
cgggccagat caggaacatg gaagatcttt ggcatgttgt cgctggctct cttaaagcgt  14400
atggcctgca tcgtcttggc atccgcgaga agcagggtgt gctcttcacc gaaattggcg  14460
aagcgctacg gttgatcatg actggtcggt tcacaccggt tccggtcgtc agcggctcac  14520
tcggcgcttc gatttatacc gacagagtca tttgcggcaa gcgaggactc gagatcagaa  14580
cgccaaaaga cagttacgtt ggatccatct attcgtttcg cgaataccct gcaaaaacac  14640
ggccgggcat gctcaacgcg ctgctatccc tcgattttcc acttgttctc acgcagagtt  14700
tttcgttcct gactcgcccg caagcgcacg cgaaacttag cctcaaatcg agccagatgc  14760
tgagttccgg cgataaagcc gtgactcaaa tcggcaaatt atccgaggct gaggacgcac  14820
ttgcgagcaa cgaattcgtt atgggctcac atcatttgag cctttgcgtc tatgcagacg  14880
atctcaatag tcttggggac aggggcgcgc gggctcggac acgaatggcg gatgcaggtg  14940
ccgtggttgt ccaagaaggt attggtatgg aagcggccta ttggtcccaa ttgccgggga  15000
attttaagtg gcgcacacgc cctggcgcaa tcacttcacg caatttcgca gggtttgtct  15060
ctttcgaaaa ctttccagag ggcgccagct caggccactg gggcaacgcg attgcccgat  15120
ttcgtaccaa tggcggaacg cctttcgact atatcccgca tgagcacgat gttggcatga  15180
cggcaatatt cgggcctatc gggaggggta agacgacgct catgatgttt gttctagcca  15240
tgctcgaaca gagcatggtc gaccgtgcag gtacggtcgt gttctttgac aaggaccggg  15300
gtggcgaatt gctggttcgc gccacaggag gaacatattt ggcacttcac agaggcacac  15360
ccagcgggtt ggcgccgttg cgtggcctag aaaacacagc agcctcacac gattttctgc  15420
```

```
gcgaatggat cgtggctctc atcgagagtg atggtcgggg tgggatttct ccggaagaga  15480
accgccgtct ggtccgtggt atccatcgtc agctctcgtt tgatccacaa atgcgttcaa  15540
tcgcggggtt acgtgaattt ttgttgcatg ggcccgccga aggcgcagga gcgcggctcc  15600
aacgctggtg ccggggccat gcgcttggct gggcatttga cggcgaagtt gacgaagtaa  15660
agttagatcc gtcgattacc ggcttcgaca tgacgcatct tctcgaatac gaggaagtat  15720
gcgctcccgc tgcagcatat ctcctgcatc ggattggagc catgatcgac ggccgccgtt  15780
ttgtgatgag ctgcgatgag tttcgcgcct atttgttaaa ccctaaattt tcgactgtcg  15840
tcgacaaatt cctcctgacc gttcgaaaaa acaacgggat gctaatactg gcaacgcagc  15900
aaccagagca tgttctggaa tcgccgctag gagccagctt ggttgcgcaa tgtatgacga  15960
agattttcta tccatcacca accgcagatc gatcggctta tgtcgatgga ctgaaatgta  16020
ccgaaaagga atttcaggcg atccgtgaag acatgacggt cggcagccgt aagtttcttc  16080
ttaaacgaga aagtggaagc gtcatctgcg aatttgatct gcgggatatg cgtgaatatg  16140
tcgccgtgct ttcggggcgt gccaacacgg tgcgctttgc aactcgacta cgcgaggcac  16200
aagaaggcaa ctcatctggc tggctcagcg aattcatggc ccgtcaccac gaggcagaag  16260
attgataagg taggaaacga tgaagacgac gcaacttatt gcaacagttt tgacctgcag  16320
ctttctatat attcagcccg cgcgggcgca gtttgttgtt agcgacccgg caacggaggc  16380
tgagacgctc gcgactgcgc tcgcgactgc ggagaatctc actcagacta tagcgatggt  16440
tacgatgttg acgtcggcct acggcgttac tggactactg acttcgctca accagaaaaa  16500
tcagtatcct tcgacgaagg acctagacaa tgaaatgttt tcgccgcgaa tgccaatgtc  16560
gaccacggca cgtgcgatca ccagcgatac agatcgtgca gtcgtgggta gtgatgctga  16620
agcggacctg ttgcgatcgc agatcaccgg ttccgcaaac agcgctggca ttgcggctga  16680
caatctggaa acgatggaca aacgcttgac ggcgaatgct gatacgtctg ctcagctttc  16740
ccgatctcgc aatatcatgc aggcaaccgt gaccaatggt ttgcttctca agcagatcca  16800
tgacgcaatg attcaaaatg tacaggcgac aagcctatta acgatgacta ccgcgcaggc  16860
cggccttcac gaggcggaag aggcggccgc tcaacgcaag gagcatcaaa agaccgctgt  16920
catctttggt gccctcccct aaggctgggc gatttgttca tccgcccgca tcctcgccga  16980
atgcgagctc attttatcca acattatgcg acaaaccagt caagttcagg tccaatcgat  17040
gaatttcacg attccggcgc cgtttacggc cattcatacg atcttcgatg tagccttcac  17100
gacaggcttg gactcgatgc ttgagactat ccaggaggcg gtgagtgcgc cattgatcgc  17160
ctgtgtcact ctttggatta ttgttcaggg tattttagtc atacgcggcg aagtcgatac  17220
ccgtagcggt atcactcggg tgatcacggt caccatcgtt gttgctctaa ttgttgggca  17280
ggctaactac caagactatg tggtttccat cttcgaaaag acggtcccaa actttgttca  17340
gcagtttagt gtaaccggct tgcctctgca gactgttccg gcacagttgg atacaatgtt  17400
cgccgtgacc caggccgttt ttcagaaaat cgcatccgaa atcggtccga tgaacgacca  17460
ggacatcctt gctttccaag gggcacagtg ggtcctttac ggcacgctct ggtctgcctt  17520
cggagtttac gacgccgttg gaattctcac gaaagtgctt ctcgcgatcg ggcctctgat  17580
cctcgtcgga tatatttttg atcgcacgcg ggacatcgca gctaagtgga tcgggcaact  17640
tatcacctac ggtctcttgc ttctcctctt aaacctcgtg gcaacgatcg tcatcctaac  17700
cgaagcgact gcgctcaccc ttatgcttgg tgtaatcacc ttcgccggta cgaccgcggc  17760
caagatcatt ggtctttacg aactcgatat gttttttctg acaggggatg cgctcattgt  17820
```

```
cgctttgccg gcgatcgccg gcaacattgg aggcagttac tggagcggcg caacccaatc  17880
tgccagcagc ttgtaccgtc gcttcgctca ggttgagcga ggctaggtcg cgcaaaaatt  17940
cgcctcaatg gagaattcta tgaagtattg cctgctgtgc ctagttgtcg ctttgagcgg  18000
ctgccagaca aacgacacat tagcgagctg caaaggcccg atcttcccgc tgaatgtggg  18060
gcgatggcag cctactccgt cagatcttca gctcggcaat tcgggtggac gctatgacgg  18120
ggcctgaata tgccatgcta gtggcgcgcg aaagccttgc cgagcactat aaggaagtag  18180
aagcctttca aaccgcgcga gcgaaatcgg cgcgacgtct ctccaaactc attgcagctg  18240
tcgcagctat cgcgattttg ggaaatgttg ctcaagcgtt cgctatagcc acaatggtgc  18300
cgttgagcag gcttgtgccc gtatatctat ggatacggcc ggacggcacc gttgacagcg  18360
aggtgtctgt ctcgcgattg cctgcaactc aagaggaggc cgtcgttaac gcctcattgt  18420
gggagtacgt tcgcctgcgc gagagttatg atgccgacac cgctcagtac gcctacgacc  18480
tggtatcgaa cttcagtgcc ccaacagtgc gccaggatta ccagcaattc ttcaactatc  18540
ccaatcccag ttcgcctcaa gtcattcttg gcaaacgcgg cagggtggag gtcgagcaca  18600
tcgcttcaaa tgatgtaact ccaagcacgc agcaaattcg ctataaaagg accctcgtcg  18660
ttgacggcaa aatgcctgtg gtgagtacgt ggaccgcgac agttcgctac gaaaaggtga  18720
ccagcttgcc cggcagattg agactaacca acccggcagg tctggttgtc acctcctatc  18780
agacatcgga agataccgtt tcaaacgtag gccacagcga accatgatca gaaaagcact  18840
tttcatttta gcatgtttat ttgccgctgc gactggtgcg gaggctgaag acactccaat  18900
ggcgggcaag ctagatccgc gcatgcgtta tttggcttac aatcccgatc aagtggtgcg  18960
cctctcgacg gcggttggag ctactttggt cgtaacattc gccacgaacg aaacggtgac  19020
agcggttgcc gtttcaaata gcaaagatct agcagcccta ccgcggggaa attatctatt  19080
tttcaaggca agccaggtcc tcacgcctca gccagtaatc gtgctaaccg caagcgactc  19140
cgggatgcgc cgttatgttt tcagtataag ttccaagact ctgtcccacc tcgataaaga  19200
gcagcccgat ctctattaca gcgtccaatt cgcctacccc gccgacgatg cggcggctcg  19260
gcgaagggag gcacaacaga aggctgttgt ggacagacta cacgcggaag cacaatatca  19320
acggaaagct gagaatttat tggatcagcc tgtcacagcc cttggtgcgg cggacagtaa  19380
ttggcactac gtcgcccaag gcgatcgttc gctgttgcca ctcgaagtct tcgacaatgg  19440
atttacgacg gtattccact ttccgggcaa tgtacgcata ccctccatct acaccatcaa  19500
tcctgatggc aaggaagctg ttgccaacta ttcagttaaa gggagcgatg tcgagatttc  19560
ttcggtttcc cgaggttggc gtctgaggga tggccacaca gtactatgta tctggaacac  19620
cgcttacgat cccgttggcc aaaggccgca aacgggcacg gtgaggcccg atgtgaaacg  19680
cgtcctgaag gggcgaaggg gatgaataac gatagtcagc aagcggcaca tgaggttgat  19740
gcatctggat ccctggtctc cgacaaacat cgccggcgtc tttcggggtc tcagaaattg  19800
atcgtcggag gtgtcgttct cgcgttatca ttaagcctca tttggctagg tgggcgccaa  19860
aagaaggtga atgagaacgc atcgccgtca actttgatcg caacaaacac caagccattt  19920
catccagctc cgattgaggt gccgccggat cctccagcgg ttcaagaggc tgttcagcct  19980
gctgctcctc taccgccgag gggcgaaccg gagcggcatg agccacggcc ggaagaaaca  20040
ccgatttttg catatagcag cggcgatcaa ggggtcagca aacgcgccat tcagggcgac  20100
acgggccgaa gacaagaagg caagcgtgac gacaactcct tgccgaatgg cgaagtgtcc  20160
```

ggcgagaacg atttgtcgat acgtatgaaa cccaccgagc tgcagcccag cagcgccacg 20220
ctcttgccgc accccgattt tatggtaacg caagggacaa taattccgtg catcttgcaa 20280
accgcaatcg acacaaattt ggcaggctat gtaaagtgtg tcttgcctca ggatattcgt 20340
ggaacaacga acaatatcgt gcttcttgat cgtggcacca ccgttgttgg cgaaatacag 20400
cgtggcttgc aacagggaga tgggcgcgtt tttgtgttgt gggatcgcgc cgagacacct 20460
gaccatgcga tgatctcgtt aacatcgcca agcgcggacg aactcggtcg ctcaggattg 20520
ccgggctcgg tcgacagcca cttctggcag cgttttagcg gagctatgct cttgagtgtt 20580
gttcaaggcg ccttccaggc agctagcacc tacgccggca gctcgggtgg cgggatgagc 20640
ttcaacagct ttcaaaataa cggtgagcag acaactgaga cagcccttaa ggcaaccatc 20700
aacataccgc caaccctgaa gaagaatcag ggtgacaccg tttccatttt cgtagcacgg 20760
gacctcgatt tctttggtgt ttaccagctc cgcctgactg gcggcgccac gcgggggagg 20820
aaccgccgct cttaatgaat tcaaatttcc gcttagagat aggatacatt gtaaatggaa 20880
gtggatccgc aactacgctt tcttctgaag ccgattttgg aatggctcga tgacccgaag 20940
actgaagaaa ttgcgatcaa tcgacctgga gaggcatttg tgcgccaagc cggcattttt 21000
accaagatgc ctttgcccgt ctcttatgat gatcttgaag atatcgctat tttagcgggc 21060
gcgctgagaa agcaggatgt cggaccacgt aaccccctct gcgccactga acttcctggt 21120
ggtgaacgac tacaaatctg tctgccgccg accgttccct cgggcaccgt cagcttgacc 21180
attcgacggc caagctcgcg tgtttctggt cttaaagaag tctcctcccg ttatgatgct 21240
tcgaggtgga accagtggca gacacgaagg aaacgccaaa atcaggatga tgaagctatc 21300
cttcagcatt ttgacaacgg ggatttggaa gcgtttctgc acgcatgcgt cgtcagccga 21360
ctgacgatgt tgctatgtgg ccctaccgga agcggcaaga caacaatgag caagaccttg 21420
atcagcgcca tcccccccca ggaaaggcta atcaccatag aagatacgct cgaactcgtc 21480
attccacacg ataatcatgt tagactactc tactccaaga acggtgctgg gctgggtgct 21540
gtgagcgccg agcacttgct ccaagcaagt ctgcgtatgc ggccggaccg gatattgctt 21600
ggcgagatgc gcgacgatgc agcatgggct tatctgagtg aagtcgtctc gggacatccg 21660
ggatcgattt caacaataca cggcgcgaat ccaatccaag gattcaagaa actgttttcc 21720
cttgtcaaaa gtagcgccca aggtgctagc ttggaagatc gcacactgat tgacatgctc 21780
tctacggcga tcgatgtcat cattccattc cgtgcctatg aggacgttta tgaagtaggc 21840
gagatctggc tcgcggcgga cgcacgacgc cggggcgaga ccataggcga tctccttaat 21900
caatagtagc tgtaacctcg aagcgtttca cttgtaacaa cgattgagaa cttttgtcat 21960
aaaattgaaa tacttggttc gcattttcgt catccgcggt cagccgcaat tctgacgaac 22020
tgcccattta gctggagatg attgtacatc cttcacgtga aaatttctca agcgctgtga 22080
acaagggttc agattttaga ttgaaaggtg agccgttgaa acacgttctt cttatcgatg 22140
acgatgtcgc tatgcggcat cttattatcg aataccttac gatccacgcc ttcaaagtga 22200
ccgcggtagc cgacagcacc cagttcacta gagtactctc ttccgcgacg gtcgatgtcg 22260
tggttgttga tctaaattta ggtcgtgaag atgggcttga gatcgttcga aatctggcgg 22320
caaagtctga tattccaatc ataattatca gtggcgaccg ccttgaggag acggataaag 22380
ttgttgcact cgagctagga gcaagtgatt ttatcgctaa gccgtttagt acgagagagt 22440
ttcttgcacg cattcgggtt gccttgcgcg tgcgccccaa cgttgtccgc tccaaagacc 22500
gacggtcttt ttgttttact gactggacac ttaatctcag gcaacgtcgc ttgatgtccg 22560

```
aagctggcgg tgaggtgaaa cttacggcag gtgagttcaa tcttctcctc gcgtttttag  22620
agaaaccccg cgacgttcta tcgcgcgagc aacttctcat tgccagtcga gtacgcgacg  22680
aggaggttta cgacaggagt atagatgttc tcattttgcg gctgcgccgc aaacttgagg  22740
cggatccgtc aagccctcaa ctgataaaaa cagcaagagg tgccggttat ttctttgacg  22800
cggacgtgca ggtttcgcac ggggggacga tggcagcctg agccaattgc atttggctct  22860
taattatctg gctcaaaagg tgactgagga cgcggccagc ggcctcaaac ctacactcaa  22920
tatttggtga ggggttccga taggtccctc ttcaccaatt gctcgatggc ttctctccag  22980
caaagaatga cgcgagcgcg gcggtagcca gcttgtggcc gaaagctcga gcggtctcca  23040
accccaacgg atcaaaatga cttcgagcga cctcgagcaa cgcaaccggg aacatgcgtg  23100
aggtctgaac gagaacggat ttttctgtag ttgaagggat cggataactt ttcggggcca  23160
cgcgaaatga tccatctgcc agcatgcttt cgaaatcgtc caacgcgcgc cttaaaatca  23220
tttgtagcga cttcgaggga ctgtattgcc gaacgaggtt gtcatatgtt ttcgacactt  23280
gaggcgcggg cggtcgcgct gaaagaaaaa cctggagctt tttcggggac ggaggtggac  23340
taagggcatc cacagttagc ttaagttgtc gatcgggact gtaaatgtga tcggcgacga  23400
gaggctcacg ttgctggtct ttctcgtcgg ctttttcagg caagtgctgg aggtccagct  23460
tctggggaac aagtgtcggg ttgggatggt ggatctcggg tcgagcacca gcaagccgcc  23520
gtgcttcgcc gaccgacaat gcgggcttgc gaattgccat cttcaagcct ccaagatttt  23580
gctgatcagt ttcgaaatga ccacgacttc ctccatcgca atccgaagat tcctctctat  23640
gaggcgcatc gtcggatcag ttcccgtgtt tagtaatgta agatgcaaca tgccgcgttc  23700
tttcatcgcg gcaaatgcat ctctttcatg catgggagac ggtacaactg gaaggctctc  23760
tagcgtctct gacatcctgc gttgcgatgt tgtcaatcgg ccgaccggga cgcgttggcg  23820
caaaacagct gtaggaattg ccaaattttc actcaacagc agctcgatga cgtagcggta  23880
ggtagatagt gcctcatcga tgtcgagcgg cgttagcatg gtggggatca gaagcaggtt  23940
tgagctagcg atgattgtgt tgttgagctc gctcgagccg ccacgcgtat cggccaacgc  24000
ataatcaaat ccttcgagct cggcattttc ataggctgct tcaagaaggg gcatttcgtc  24060
ggcggaatag acttcacagc gaggatccca gtactgcttt gtaaggcgtt ttctctccat  24120
cgcgtcagag gccggttttc gtcggcatca aagagggcca ctcgtttacc gtcatttgcc  24180
aaagcagcgc aaaggcccat gagtgcggtg gttttgccag caccccccttt gaaagaacaa  24240
aacgtcaaaa gttgcatatt ctgatcccgc ctatcctgtg aaaccggagt gcatttgtat  24300
ttttgttcgt ataaatgttt ttgtgattat cgatgagtaa aagcgttgtt acactatttt  24360
tatttcacat tcgttataag acaattgcaa atgtagcaag tatattcagt attgactgta  24420
aatgtactgt tgatttcata ttgagcaggg ctagacttcc atccgtctac ccgggcacat  24480
ttcgtgctgg agtatccaga ccttccgctt tctttggagg aagctatgtc aaaacacacc  24540
agagccacgt cgagtgagac taccatcaac cagcatcgat ccctgaaagt tgaagggttc  24600
aaggtcgtga gtgcccgtct gcgatcggcc gagtatgaaa ccttttccta tcaagcgcgc  24660
ctgctgggac tttcggatag tatggcaatt cgcgttgcgg tgcgccgcat cgggggcttt  24720
ctcgaaatag atgcagacac acgagaaaag atggaagcca tacttcagtc catcggaata  24780
ctctcaagca atgtatccat gcttctatct gcctacgccg aagaccctcg atcggatctg  24840
gaggctgtgc gagatgaacg tattgctttt ggcgaggctt tcgccgccct cgatggacta  24900
```

```
ctgcgctcca ttttgtccgt atcccggcga cggatcgacg gtcgctcgtt actgaaaggt  24960

gccttgtagc acttgaccac gcacctgacg ggagaaaatt ggatgcccga tcgcgctcaa  25020

gtaatcattc gcattgtgcc aggaggtgga accaagaccc ttcagcagat aatcaatcag  25080

ctggagtacc tgtcccgaaa gggaaagctg gaactgcagc gttcagcccg gcatctcgat  25140

attcccgttc cgccggatca aatccgtgag cttgcccaaa gctgggttac ggaggccggg  25200

atttatgacg aaagtcagtc agacgatgac aggcaacaag acttaacaac acacattatt  25260

gtaagcttcc ccgca                                                    25275
```

<210> SEQ ID NO 6
<211> LENGTH: 3492
<212> TYPE: DNA
<213> ORGANISM: Artificial sequence
<220> FEATURE:
<223> OTHER INFORMATION: maize-codon-optimized coding region for cry1Ca

<400> SEQUENCE: 6

```
atggataaca accccaacat taacgagtgc atcccgtaca actgcctctc gaatccagaa     60

gaagtgctct tggatggcga gaggatttcg actggcaaca gctccatcga catttccctc    120

tccttggttc agttccttgt gtctaacttc gtccctggcg gtggcttcct tgttggcctt    180

atcgacttcg tctggggaat tgtcggaccc tcccagtggg atgcgtttct ggtgcagata    240

gagcagctga tcaacgagag gatcgctgag ttcgcgagaa atgctgcaat cgccaacctt    300

gaagggcttg gcaacaactt caacatctac gtggaggcgt tcaaggagtg ggaagaggac    360

cctaagaatc cagcgaccag aacgagggtt atagatcggt tccgcatcct cgatggcctt    420

ttggagaggg acatcccgag cttccgcatt tcgggatttg aggttcctct gctctcagtc    480

tacgctcaag ctgctaatct gcatctggcc atcttgaggg attcagtcat ctttggcgaa    540

cgctggggtc ttacgactat caacgtgaac gagaactaca atcggttgat tcggcacata    600

gacgagtatg ccgaccactg tgctaacacc tacaataggg gtctgaacaa tctgccaaag    660

tcaacgtatc aagactggat aacctacaat aggctcagac gggacctcac tctcaccgtg    720

ctggacatag ctgccttctt tccgaactac gacaaccgga gatatcctat tcaacccgtt    780

ggtcagctca ctcgcgaggt ctacaccgat cccctcatca acttcaatcc ccagctgcaa    840

tcggtcgcac agctgcccac cttcaatgtg atggaaaact cagcgatccg gaatccccat    900

ctgtttgaca tacttaacaa cctcactatc ttcaccgatt ggttttcagt tggacgcaac    960

ttctactggg gagggcacag agtgatttca agcctcattg gaggagggaa cattacatcg   1020

cctatctatg gaagggaggc caaccaagag ccaccaaggt ctttcacctt caacggtccg   1080

gtgttcagaa cacttagcaa tcccacattg cgcttgctgc aacagccgtg gccagcacca   1140

ccattcaatc tgaggggagt ggagggtgtg gagttctcga cgcctacaaa ctcctttacg   1200

tacagaggca gagggacagt ggactcactg acagaactcc cacctgagga caactctgtt   1260

cctccgaggg agggctactc gcaccggctt tgccatgcca ccttcgtcca gaggtctggc   1320

acgccttttc tgaccactgg ggttgtcttt agctggactc accgctcagc gacgctgacc   1380

aacacaatcg acccagagag gatcaatcag atccctctgg tgaagggctt tcgcgtttgg   1440

ggtggcacaa gcgtgatcac cggacctggt ttcactggtg gggatatcct cagacgcaat   1500

acgtttggcg atttcgtgag ccttcaagtc aacatcaatt ccccaatcac ccagagatat   1560

cggctccgct tcagatacgc ctcatccaga gacgcaaggg tcatcgtcct tactggagca   1620

gccagcaccg gagtcggagg ccaagttagc gtcaacatgc cgttgcagaa aacgatggaa   1680
```

```
atcggtgaaa acctcaccag cagaaccttt cgctatacag atttcagcaa ccctttctcc   1740
ttcagagcca atccggacat aatcggcata tccgagcagc ccttgttcgg tgctgggtcc   1800
atctcttctg gcgagctgta catcgacaag attgagatca ttctcgcaga tgcgactctc   1860
gaggctgaat cggatcttga aagggcacag aaggcagtca acgctctctt caccagctca   1920
aatcagattg gccttaagac cgatgttact gactatcata tcgacagagt ttctaacctt   1980
gtcgagtgcc tctccgacga gttctgtctc gacgaaaaga aggaactctc cgagaaagtg   2040
aagcacgcga aacgcctctc ggatgaacgg aacttgctgc aagatccgaa cttcagaggc   2100
atcaatcgcc agttggatag aggctggagg ggatcaaccg acataaccat tcaaggtggg   2160
gatgatgtgt tcaaggaaaa ctacgtgaca ttgctgggca ccttcgacga gtgctatccc   2220
acgtatctct atcagaagat tgacgagtcc aagctcaaag cctacacacg ctatcagctc   2280
agaggctaca ttgaggactc tcaagacctc gaaatctact tgatcagata caacgccaag   2340
cacgagacgg tgaacgtccc tggactgggt cactgtggc cactgtcggc accctcgcca   2400
atcggaaagt gcgctcacca cagccaccac ttctcccttg acatagatgt tgggtgtacg   2460
gacttgaatg aggatctggg tgtgtgggtg atctttaaga tcaagaccca agatggtcat   2520
gcgaggcttg gcaaccttga gttccttgaa gagaagcctt tggtcggaga ggcactggct   2580
cgcgtgaaga gggctgagaa gaaatggagg gacaagaggg agaaactgga gtgggagacc   2640
aacatagtgt acaaggaggc caaggagtca gtggacgcac tgtttgtcaa ttcccagtat   2700
gataggctcc aagcggacac gaacatcgcc atgatccatg cagcggacaa gagggttcac   2760
tccataaggg aggcctatct tccggagctg tcagtgattc ctggggtcaa cgcagccatc   2820
tttgaggaat tggaagggag gatcttcacc gctttctctc tgtacgacgc tcggaacgtc   2880
atcaagaatg gtgatttcaa caatggactc agctgctgga acgtgaaagg gcatgtcgat   2940
gttgaagaac agaacaatca ccgcagcgtg ctggtggttc cggagtggga agccgaggtc   3000
tcacaagaag tcagagtgtg ccctgggagg ggttacatct tgcgggtcac agcctacaag   3060
gaaggttatg gcgaaggctg tgtcacgatc catgagatcg aaaacaacac agacgagctg   3120
aagttttcca actgtgttga ggaggaggtc tatcctaaca atactgttac gtgcaacgac   3180
tacacagcca ctcaagagga gtacgagggc acttacacct ctcgcaacag aggctacgac   3240
ggtgcctacg agtcaaacag ctccgtgcca gcggactacg cctcggctta cgaagagaag   3300
gcgtacaccg acggtcggag ggataacccg tgcgagagca atagaggcta tggcgactac   3360
actcctctcc cagctggcta cgtgaccaag gagttggagt actttccgga gacagacaaa   3420
gtctggattg agattggaga gacagaaggc acgttcatcg tggactctgt tgaactcttg   3480
ctgatggagg ag                                                       3492
```

<210> SEQ ID NO 7
<211> LENGTH: 1164
<212> TYPE: PRT
<213> ORGANISM: Bacillus thuringiensis

<400> SEQUENCE: 7

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45
```

```
Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460
```

```
Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Leu Glu Ala Glu Ser
    610                 615                 620

Asp Leu Glu Arg Ala Gln Lys Ala Val Asn Ala Leu Phe Thr Ser Ser
625                 630                 635                 640

Asn Gln Ile Gly Leu Lys Thr Asp Val Thr Asp Tyr His Ile Asp Arg
                645                 650                 655

Val Ser Asn Leu Val Glu Cys Leu Ser Asp Glu Phe Cys Leu Asp Glu
            660                 665                 670

Lys Lys Glu Leu Ser Glu Lys Val Lys His Ala Lys Arg Leu Ser Asp
        675                 680                 685

Glu Arg Asn Leu Leu Gln Asp Pro Asn Phe Arg Gly Ile Asn Arg Gln
    690                 695                 700

Leu Asp Arg Gly Trp Arg Gly Ser Thr Asp Ile Thr Ile Gln Gly Gly
705                 710                 715                 720

Asp Asp Val Phe Lys Glu Asn Tyr Val Thr Leu Leu Gly Thr Phe Asp
                725                 730                 735

Glu Cys Tyr Pro Thr Tyr Leu Tyr Gln Lys Ile Asp Glu Ser Lys Leu
            740                 745                 750

Lys Ala Tyr Thr Arg Tyr Gln Leu Arg Gly Tyr Ile Glu Asp Ser Gln
        755                 760                 765

Asp Leu Glu Ile Tyr Leu Ile Arg Tyr Asn Ala Lys His Glu Thr Val
    770                 775                 780

Asn Val Pro Gly Thr Gly Ser Leu Trp Pro Leu Ser Ala Pro Ser Pro
785                 790                 795                 800

Ile Gly Lys Cys Ala His His Ser His His Phe Ser Leu Asp Ile Asp
                805                 810                 815

Val Gly Cys Thr Asp Leu Asn Glu Asp Leu Gly Val Trp Val Ile Phe
            820                 825                 830

Lys Ile Lys Thr Gln Asp Gly His Ala Arg Leu Gly Asn Leu Glu Phe
        835                 840                 845

Leu Glu Glu Lys Pro Leu Val Gly Glu Ala Leu Ala Arg Val Lys Arg
    850                 855                 860

Ala Glu Lys Lys Trp Arg Asp Lys Arg Glu Lys Leu Glu Trp Glu Thr
865                 870                 875                 880

Asn Ile Val Tyr Lys Glu Ala Lys Glu Ser Val Asp Ala Leu Phe Val
```

```
                885                 890                 895

Asn Ser Gln Tyr Asp Arg Leu Gln Ala Asp Thr Asn Ile Ala Met Ile
            900                 905                 910

His Ala Ala Asp Lys Arg Val His Ser Ile Arg Glu Ala Tyr Leu Pro
        915                 920                 925

Glu Leu Ser Val Ile Pro Gly Val Asn Ala Ala Ile Phe Glu Glu Leu
    930                 935                 940

Glu Gly Arg Ile Phe Thr Ala Phe Ser Leu Tyr Asp Ala Arg Asn Val
945                 950                 955                 960

Ile Lys Asn Gly Asp Phe Asn Asn Gly Leu Ser Cys Trp Asn Val Lys
                965                 970                 975

Gly His Val Asp Val Glu Glu Gln Asn Asn His Arg Ser Val Leu Val
            980                 985                 990

Val Pro Glu Trp Glu Ala Glu Val  Ser Gln Glu Val Arg  Val Cys Pro
        995                 1000                1005

Gly Arg  Gly Tyr Ile Leu Arg  Val Thr Ala Tyr Lys  Glu Gly Tyr
    1010                1015                1020

Gly Glu  Gly Cys Val Thr Ile  His Glu Ile Glu Asn  Asn Thr Asp
    1025                1030                1035

Glu Leu  Lys Phe Ser Asn Cys  Val Glu Glu Glu Val  Tyr Pro Asn
    1040                1045                1050

Asn Thr  Val Thr Cys Asn Asp  Tyr Thr Ala Thr Gln  Glu Glu Tyr
    1055                1060                1065

Glu Gly  Thr Tyr Thr Ser Arg  Asn Arg Gly Tyr Asp  Gly Ala Tyr
    1070                1075                1080

Glu Ser  Asn Ser Ser Val Pro  Ala Asp Tyr Ala Ser  Ala Tyr Glu
    1085                1090                1095

Glu Lys  Ala Tyr Thr Asp Gly  Arg Arg Asp Asn Pro  Cys Glu Ser
    1100                1105                1110

Asn Arg  Gly Tyr Gly Asp Tyr  Thr Pro Leu Pro Ala  Gly Tyr Val
    1115                1120                1125

Thr Lys  Glu Leu Glu Tyr Phe  Pro Glu Thr Asp Lys  Val Trp Ile
    1130                1135                1140

Glu Ile  Gly Glu Thr Glu Gly  Thr Phe Ile Val Asp  Ser Val Glu
    1145                1150                1155

Leu Leu  Leu Met Glu Glu
    1160


<210> SEQ ID NO 8
<211> LENGTH: 3444
<212> TYPE: DNA
<213> ORGANISM: Artificial Sequence
<220> FEATURE:
<223> OTHER INFORMATION: maize-codon-optimized coding region for cry1Fa

<400> SEQUENCE: 8

atggagaaca atatccagaa ccagtgtgtc ccatacaatt gcctcaacaa tcctgaagtt      60

gagatcctca acgaagagag gagcactgga cgccttcccc ttgacatctc cctctccctc     120

acaaggttcc ttttgtctga gtttgttcct ggtgtgggtg tggcctttgg cctctttgac     180

ctcatctggg gcttcatcac cccatctgat tggagcctct tccttctcca gattgaacaa     240

ttgattgagc agaggattga gacccttgaa aggaacagag ccatcaccac acttcgtggc     300

cttgctgaca gctatgaaat ctacattgaa gcactccgtg agtgggaagc caatcccaac     360

aatgctcaac tccgtgaaga tgtgaggatt cgctttgcca acacagatga cgctttgatc     420
```

-continued

```
acagccatca acaatttcac cctcaccagc tttgagatcc ctttgctctc agtctatgtt    480
caagctgcaa acctccactt gagcttgctt agggatgctg tgtccttcgg acaaggttgg    540
ggacttgaca tagccactgt caacaatcac tacaacagac tcatcaactt gattcatcgc    600
tacaccaaac attgcttgga cacctacaat caaggattgg agaacctcag aggcaccaac    660
actcgccaat gggcaaggtt caaccagttt agaagggatc tcacactcac tgtgcttgac    720
atagttgctc tcttccccaa ctatgatgtt cgcacctacc caattcaaac cagctcccaa    780
cttacaaggg aaatctacac ctcctcagtc attgaggaca gcccagtttc tgccaacata    840
cccaatggtt tcaaccgtgc tgagtttggt gtcagaccac cccatctcat ggacttcatg    900
aactccttgt ttgtgactgc cgagactgtt aggtcccaaa ctgtgtgggg aggccacctt    960
gttagctccc gcaacaccgc tggcaaccgc atcaacttcc catcctatgg ggttttcaat   1020
cctggtggag ccatctggat tgcagatgag gacccaaggc ctttctacag aaccttgtca   1080
gatcctgtct ttgtcagagg aggctttggc aatccacact atgttcttgg tttgagggga   1140
gtggcttttc agcagactgg caccaatcac acccgcacat tcagaaacag cggcaccatt   1200
gacagccttg atgagatccc acctcaagac aacagcggag caccctggaa cgactactcc   1260
catgtgctca atcatgtcac ctttgtgcgc tggcctggtg agatcagcgg ttcagattct   1320
tggagagcac caatgttctc atggacccat cgctctgcca cacccacaaa caccattgat   1380
ccagagagaa tcacccagat tcccttggtg aaggcacaca cacttcagtc tggaaccaca   1440
gttgtcagag ggcctgggtt cactggtgga gacattctca gacgcacctc tggagggcca   1500
tttgcttaca ccattgtcaa catcaatggg caacttcccc agcgttaccg tgccagaatc   1560
cgctatgctt ccaccactaa cttgagaatc tatgtcacag ttgctggtga aaggatcttt   1620
gctggtcagt tcaacaagac aatggacact ggtgatccat tgacattcca gtcattctcc   1680
tatgccacca tcaacactgc attcaccttt ccaatgagcc agtccagctt cacagtgggt   1740
gcagatacct tcagctccgg caatgaggtg tacattgacc gctttgagtt gattccagtg   1800
actgccacac ttgaggctga gtctgacttg gagcgtgctc agaaggccgt gaatgctctc   1860
ttcacctctt caaatcagat tgggctcaag acagatgtga ctgactacca tatagaccgt   1920
gtttccaatc ttgttgagtg cctctctgat gagttctgct tggatgagaa gaaagagttg   1980
tcagagaagg tcaagcacgc caagaggctc tctgatgaga ggaacttgct tcaagatccc   2040
aacttcagag ggatcaaccg tcaattggat cgtggatgga ggggatcaac tgacataacc   2100
attcaaggag gtgacgatgt gttcaaggag aactatgtca cactcttggg gacctttgat   2160
gagtgctacc caacatacct ttaccagaag atagacgaaa gcaagctcaa ggcctacaca   2220
agataccagt tgagaggtta cattgaggac tctcaagacc ttgaaatcta cctcatcaga   2280
tacaacgcca aacatgagac agtcaatgtg cctgggactg gttcactctg gccactttca   2340
gccccaagcc ccattggcaa gtgtgcccat cactcacatc acttctcctt ggacatagat   2400
gttggctgca ctgacttgaa tgaggacctt ggtgtgtggg tgatcttcaa gatcaagacc   2460
caagatggcc atgcaaggtt gggcaatctt gagtttcttg aagagaaacc acttgttgga   2520
gaagcccttg ccagagtgaa gagggctgag aagaaatgga gggacaagag agagaagttg   2580
gagtgggaaa caaacattgt gtacaaagaa gccaaagaat cagttgatgc tttgtttgtg   2640
aactcccaat atgataggct ccaagctgac accaacatag caatgattca tgctgcagac   2700
aaaagggttc acagcattcg tgaagcatac cttcctgaac tctcagtgat tcctggggtc   2760
```

```
aatgctgcaa tctttgaaga gcttgaagga cgcatcttca ctgccttctc cttgtatgat   2820

gcaaggaatg tcatcaagaa tggtgacttc aacaatggcc tttcctgctg gaatgtgaaa   2880

gggcacgtgg atgttgaaga gcagaacaat caccgctctg tccttgttgt ccctgagtgg   2940

gaagctgaag tttcacaaga agttcgtgtc tgccctggtc gtggctacat tcttcgtgtg   3000

actgcttaca aagaaggcta tggagaaggt tgtgtcacca tccacgagat agagaacaat   3060

actgatgaat tgaagttcag caactgtgtt gaggaagagg tctacccaaa caatactgtc   3120

acttgcaatg actacactgc aactcaagaa gagtatgagg gcacttacac ttctcgcaac   3180

cgtggctatg atggagccta tgagagcaac tcatctgtgc ctgctgacta tgcttcagcc   3240

tatgaagaga aggcatacac tgatggaagg cgtgacaatc cttgtgaaag caacagaggc   3300

tatggggact acacacccct cccagctggc tatgtgacca aagagttgga gtactttcct   3360

gaaactgaca aggtttggat tgagatagga gaaactgaag gcacattcat agttgactct   3420

gtggagcttt tgctcatgga agag                                          3444
```

<210> SEQ ID NO 9
<211> LENGTH: 1148
<212> TYPE: PRT
<213> ORGANISM: Bacillus thuringiensis

<400> SEQUENCE: 9

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255
```

```
Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Leu Glu Ala Glu Ser
        595                 600                 605

Asp Leu Glu Arg Ala Gln Lys Ala Val Asn Ala Leu Phe Thr Ser Ser
    610                 615                 620

Asn Gln Ile Gly Leu Lys Thr Asp Val Thr Asp Tyr His Ile Asp Arg
625                 630                 635                 640

Val Ser Asn Leu Val Glu Cys Leu Ser Asp Glu Phe Cys Leu Asp Glu
                645                 650                 655

Lys Lys Glu Leu Ser Glu Lys Val Lys His Ala Lys Arg Leu Ser Asp
            660                 665                 670
```

```
Glu Arg Asn Leu Leu Gln Asp Pro Asn Phe Arg Gly Ile Asn Arg Gln
        675                 680                 685

Leu Asp Arg Gly Trp Arg Gly Ser Thr Asp Ile Thr Ile Gln Gly Gly
    690                 695                 700

Asp Asp Val Phe Lys Glu Asn Tyr Val Thr Leu Leu Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Tyr Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
        755                 760                 765

Asn Val Pro Gly Thr Gly Ser Leu Trp Pro Leu Ser Ala Pro Ser Pro
    770                 775                 780

Ile Gly Lys Cys Ala His His Ser His His Phe Ser Leu Asp Ile Asp
785                 790                 795                 800

Val Gly Cys Thr Asp Leu Asn Glu Asp Leu Gly Val Trp Val Ile Phe
                805                 810                 815

Lys Ile Lys Thr Gln Asp Gly His Ala Arg Leu Gly Asn Leu Glu Phe
            820                 825                 830

Leu Glu Glu Lys Pro Leu Val Gly Glu Ala Leu Ala Arg Val Lys Arg
        835                 840                 845

Ala Glu Lys Lys Trp Arg Asp Lys Arg Glu Lys Leu Glu Trp Glu Thr
    850                 855                 860

Asn Ile Val Tyr Lys Glu Ala Lys Glu Ser Val Asp Ala Leu Phe Val
865                 870                 875                 880

Asn Ser Gln Tyr Asp Arg Leu Gln Ala Asp Thr Asn Ile Ala Met Ile
                885                 890                 895

His Ala Ala Asp Lys Arg Val His Ser Ile Arg Glu Ala Tyr Leu Pro
            900                 905                 910

Glu Leu Ser Val Ile Pro Gly Val Asn Ala Ala Ile Phe Glu Glu Leu
        915                 920                 925

Glu Gly Arg Ile Phe Thr Ala Phe Ser Leu Tyr Asp Ala Arg Asn Val
    930                 935                 940

Ile Lys Asn Gly Asp Phe Asn Asn Gly Leu Ser Cys Trp Asn Val Lys
945                 950                 955                 960

Gly His Val Asp Val Glu Glu Gln Asn Asn His Arg Ser Val Leu Val
                965                 970                 975

Val Pro Glu Trp Glu Ala Glu Val Ser Gln Glu Val Arg Val Cys Pro
            980                 985                 990

Gly Arg Gly Tyr Ile Leu Arg Val  Thr Ala Tyr Lys Glu  Gly Tyr Gly
        995                 1000                1005

Glu Gly  Cys Val Thr Ile His  Glu Ile Glu Asn Asn  Thr Asp Glu
    1010                1015                1020

Leu Lys  Phe Ser Asn Cys Val  Glu Glu Glu Val Tyr  Pro Asn Asn
    1025                1030                1035

Thr Val  Thr Cys Asn Asp Tyr  Thr Ala Thr Gln Glu  Glu Tyr Glu
    1040                1045                1050

Gly Thr  Tyr Thr Ser Arg Asn  Arg Gly Tyr Asp Gly  Ala Tyr Glu
    1055                1060                1065

Ser Asn  Ser Ser Val Pro Ala  Asp Tyr Ala Ser Ala  Tyr Glu Glu
    1070                1075                1080

Lys Ala  Tyr Thr Asp Gly Arg  Arg Asp Asn Pro Cys  Glu Ser Asn
```

```
    1085                1090                1095

Arg Gly  Tyr Gly Asp Tyr Thr  Pro Leu Pro Ala Gly  Tyr Val Thr
    1100                1105                1110

Lys Glu  Leu Glu Tyr Phe Pro  Glu Thr Asp Lys Val  Trp Ile Glu
    1115                1120                1125

Ile Gly  Glu Thr Glu Gly Thr  Phe Ile Val Asp Ser  Val Glu Leu
    1130                1135                1140

Leu Leu  Met Glu Glu
    1145


<210> SEQ ID NO 10
<211> LENGTH: 3465
<212> TYPE: DNA
<213> ORGANISM: Artificial sequence
<220> FEATURE:
<223> OTHER INFORMATION: maize-codon-optimized coding region for cry1Ab

<400> SEQUENCE: 10

atggacaaca accctaacat caatgagtgc ataccataca actgtcttag caacccagaa     60

gttgaggttc tgggtgggga gaggatagag actggataca ctccaataga catttcgctg    120

tcactgacgc aattccttct gtctgagttc gttcctggtg ctggattcgt gctgggcttg    180

gtggacatca tttggggaat ctttggaccg tcccagtggg atgcctttct tgttcagatt    240

gagcagttga tcaatcagag aattgaggag tttgcacgca accaagccat atccagactt    300

gaaggccttt cgaacttgta tcaaatctac gcagagagct tcagagagtg ggaggcagac    360

ccgacgaatc cagccctcag agaggagatg aggattcagt tcaacgacat gaactcagca    420

ctgactactg ccattcccct ctttgccgtc cagaactatc aagtgccact gctgtccgtc    480

tacgttcaag cagcgaatct gcacctcagc gtcttgagag acgtctcggt gtttggccag    540

cgctggggtt ttgatgcagc gacgatcaat agcagataca atgacctcac aaggctgatt    600

ggaaactaca ccgattacgc agttcgctgg tacaatacgg gtctcgaacg ggtctgggga    660

cccgactcac gcgactgggt cagatacaac cagtttagac gcgagcttac tttgaccgtt    720

ctggacatag tcgcactctt tccgaactac gacagcagaa gatatccgat taggacggtt    780

tcccagctca ccagagaaat ctataccaat cccgtgctcg aaaactttga cggcagcttt    840

aggggaagcg ctcaaggcat tgagaggagc atcagatccc cacatctcat ggacattctg    900

aactcaatca cgatctacac tgatgcacat aggggttact actattggag cggtcatcag    960

atcatggcct cgccagtggg gttttcgggt ccggagttta cattccccact gtacggggaca   1020

atgggaaatg cagcaccgca acagcggatc gttgctcagc tgggtcaagg ggtgtacaga   1080

acgctctcat cgacgctgta tcggagaccc ttcaacatag gcatcaacaa ccagcaactc   1140

tcagtcttgg acggcaccga gttcgcgtat gggacatcct ccaacctccc gtctgccgtg   1200

tatcgcaagt ccggaacagt cgattcgctg gatgagattc ctccacagaa caacaacgtg   1260

cctccaagac aaggcttctc tcacagattg agccatgtga gcatgttccg ctctggcttc   1320

tccaactcct cagtgtcgat cattagggca ccgatgttct cttggataca ccggagcgca   1380

gagttcaaca acatcatccc gtcaagccag atcacgcaga tcccactgac caagtccacc   1440

aatctcggct ctgggacaag cgttgtgaag ggtcctggct tcactggtgg ggatatcctg   1500

cggaggactt ctcctggcca gatttcaacc ctcagagtca acatcaccgc accccttca   1560

cagcgctatc gggttcgcat acgctacgct tccacgacca atctgcaatt ccacactagc   1620

atcgacggga ggcctatcaa tcaaggcaac ttctcagcga ctatgtcctc gggttctaac   1680
```

```
cttcagtctg gcagcttcag aacggtgggg ttcaccactc cattcaactt ctcgaacggg   1740
tcaagcgtgt tcaccttgag cgctcacgtg ttcaattccg gaaacgaagt gtacatcgac   1800
cgcatagagt tcgtgccagc agaagttaca ttcgaagccg agtacgatct tgagagggca   1860
caaaaggctg ttaacgaact cttcaccagc tccaatcaga tcggactgaa aaccgacgtg   1920
acggactatc acatcgatca agtctcaaac ttggtggagt gcttgtctga tgagttctgt   1980
ctcgacgaaa agaaggaact gtccgaaaag gtgaagcacg ccaaacggct tagcgacgaa   2040
cgcaacttgc tccaagaccc aaactttaga gggatcaatc gccagcttga taggggatgg   2100
aggggatcaa ccgacatcac aattcaaggt ggagatgacg tgttcaagga gaactatgtg   2160
acactgcttg gaacctttga cgagtgttat ctcacatatc tgtatcagaa gatagacgag   2220
tcaaagctca aagcgtacac tcgctatcag ttgagaggct acatcgagga ttcgcaagac   2280
ctcgaaatct atctcataag atacaatgcg aagcacgaga cggtgaacgt tcctgggact   2340
ggttcactct ggaggttgtc cgctccctcc cctatcggca aatgtgccca ccactctcac   2400
cactttagct tggacataga tgtgggctgc accgatctga atgaggatct gggtgtctgg   2460
gtgatcttca agatcaagac acaagacgga catgccagac tcgggaatct ggagttcctt   2520
gaggaaaagc ctctcgtggg tgaggcgttg gcacgcgtca aagagcggga gaagaaatgg   2580
agggacaaac gcgagaagct cgaatgggaa acaaacatcg tgtacaagga ggcgaaggag   2640
tcggtggacg ctctctttgt caactcacag tacgacagac ttcaagctga cactaacatt   2700
gccatgattc atgcagcaga caaacgggtc cattccatta gggaggctta tctcccagag   2760
ctttcagtga ttcctggcgt caacgctgcg atcttcgagg agcttgaggg tcggatcttc   2820
accgctttct cgttgtacga cgcgaggaac gtcatcaaga atggtgactt caacaatggc   2880
ctttcgtgct ggaatgtcaa aggccatgtc gatgtggagg agcagaacaa ccaccgctcc   2940
gtccttgtcg tcccagaatg ggaagccgag gtctctcaag aggttcgggt ttgccctggg   3000
aggggttaca ttctcagagt gaccgcttac aaagagggct acggagaggg ctgcgtcacg   3060
atccacgaga tcgaaaacaa cacggacgag ctgaagttct caaactgcgt cgaggaagag   3120
gtctatccta acaacacagt cacttgcaac gattacacag ccacgcaaga ggaatacgaa   3180
ggcacctaca cctcacggaa taggggatac gatggtgcct acgagagcaa ttcctcagtt   3240
ccagcggatt acgcgtcagc gtatgaagag aaggcttaca ccgatgggag aagggataac   3300
ccatgcgaga gcaatagggg atatggtgac tacacccctc tgccagctgg ctatgtgacc   3360
aaggaacttg aatacttccc agagactgac aaggtgtgga ttgagatcgg tgagacagaa   3420
ggaaccttca tcgtggattc tgttgagctg ttgctcatgg aggag                   3465
```

<210> SEQ ID NO 11
<211> LENGTH: 1155
<212> TYPE: PRT
<213> ORGANISM: Bacillus thuringiensis

<400> SEQUENCE: 11

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
```

```
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480
```

```
Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Leu Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Arg Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Glu Lys Pro Leu Val Gly Glu
        835                 840                 845

Ala Leu Ala Arg Val Lys Arg Ala Glu Lys Lys Trp Arg Asp Lys Arg
    850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895
```

```
Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
                965                 970                 975

Asn His Arg Ser Val Leu Val Val Pro Glu Trp Glu Ala Glu Val Ser
            980                 985                 990

Gln Glu Val Arg Val Cys Pro Gly  Arg Gly Tyr Ile Leu  Arg Val Thr
        995                 1000                1005

Ala Tyr  Lys Glu Gly Tyr Gly  Glu Gly Cys Val Thr  Ile His Glu
    1010                1015                1020

Ile Glu  Asn Asn Thr Asp Glu  Leu Lys Phe Ser Asn  Cys Val Glu
    1025                1030                1035

Glu Glu  Val Tyr Pro Asn Asn  Thr Val Thr Cys Asn  Asp Tyr Thr
    1040                1045                1050

Ala Thr  Gln Glu Glu Tyr Glu  Gly Thr Tyr Thr Ser  Arg Asn Arg
    1055                1060                1065

Gly Tyr  Asp Gly Ala Tyr Glu  Ser Asn Ser Ser Val  Pro Ala Asp
    1070                1075                1080

Tyr Ala  Ser Ala Tyr Glu Glu  Lys Ala Tyr Thr Asp  Gly Arg Arg
    1085                1090                1095

Asp Asn  Pro Cys Glu Ser Asn  Arg Gly Tyr Gly Asp  Tyr Thr Pro
    1100                1105                1110

Leu Pro  Ala Gly Tyr Val Thr  Lys Glu Leu Glu Tyr  Phe Pro Glu
    1115                1120                1125

Thr Asp  Lys Val Trp Ile Glu  Ile Gly Glu Thr Glu  Gly Thr Phe
    1130                1135                1140

Ile Val  Asp Ser Val Glu Leu  Leu Leu Met Glu Glu
    1145                1150                1155


<210> SEQ ID NO 12
<211> LENGTH: 888
<212> TYPE: DNA
<213> ORGANISM: Artificial sequence
<220> FEATURE:
<223> OTHER INFORMATION: plant-codon-optimized coding region for aad1

<400> SEQUENCE: 12

atggctcatg ctgccctcag ccctctctcc caacgctttg agagaatagc tgtccagcca     60

ctcactggtg tccttggtgc tgagatcact ggagtggact tgagggaacc acttgatgac    120

agcacctgga atgagatatt ggatgccttc cacacttacc aagtcatcta ctttcctggc    180

caagcaatca ccaatgagca gcacattgca ttctcaagaa ggtttggacc agttgatcca    240

gtgcctcttc tcaagagcat tgaaggctat ccagaggttc agatgatccg cagagaagcc    300

aatgagtctg gaagggtgat tggtgatgac tggcacacag actccacttt ccttgatgca    360

cctccagctg ctgttgtgat gagggccata gatgttcctg agcatggcgg agacactggg    420

ttcctttcaa tgtacacagc ttgggagacc ttgtctccaa ccatgcaagc caccatcgaa    480

gggctcaacg ttgtgcactc tgccacacgt gtgttcggtt ccctctacca agcacagaac    540
```

```
cgtcgcttca gcaacacctc agtcaaggtg atggatgttg atgctggtga cagagagaca    600

gtccatccct tggttgtgac tcatcctggc tctggaagga aaggccttta tgtgaatcaa    660

gtctactgtc agagaattga gggcatgaca gatgcagaat caaagccatt gcttcagttc    720

ctctatgagc atgccaccag atttgacttc acttgccgtg tgaggtggaa gaaagaccaa    780

gtccttgtct gggacaactt gtgcaccatg caccgtgctg ttcctgacta tgctggcaag    840

ttcagatact tgactcgcac cacagttggt ggagttaggc ctgcccgc                 888


<210> SEQ ID NO 13
<211> LENGTH: 296
<212> TYPE: PRT
<213> ORGANISM: Sphingobium herbicidorans

<400> SEQUENCE: 13

Met Ala His Ala Ala Leu Ser Pro Leu Ser Gln Arg Phe Glu Arg Ile
1               5                   10                  15

Ala Val Gln Pro Leu Thr Gly Val Leu Gly Ala Glu Ile Thr Gly Val
            20                  25                  30

Asp Leu Arg Glu Pro Leu Asp Asp Ser Thr Trp Asn Glu Ile Leu Asp
        35                  40                  45

Ala Phe His Thr Tyr Gln Val Ile Tyr Phe Pro Gly Gln Ala Ile Thr
    50                  55                  60

Asn Glu Gln His Ile Ala Phe Ser Arg Arg Phe Gly Pro Val Asp Pro
65                  70                  75                  80

Val Pro Leu Leu Lys Ser Ile Glu Gly Tyr Pro Glu Val Gln Met Ile
                85                  90                  95

Arg Arg Glu Ala Asn Glu Ser Gly Arg Val Ile Gly Asp Asp Trp His
            100                 105                 110

Thr Asp Ser Thr Phe Leu Asp Ala Pro Pro Ala Ala Val Val Met Arg
        115                 120                 125

Ala Ile Asp Val Pro Glu His Gly Gly Asp Thr Gly Phe Leu Ser Met
    130                 135                 140

Tyr Thr Ala Trp Glu Thr Leu Ser Pro Thr Met Gln Ala Thr Ile Glu
145                 150                 155                 160

Gly Leu Asn Val Val His Ser Ala Thr Arg Val Phe Gly Ser Leu Tyr
                165                 170                 175

Gln Ala Gln Asn Arg Arg Phe Ser Asn Thr Ser Val Lys Val Met Asp
            180                 185                 190

Val Asp Ala Gly Asp Arg Glu Thr Val His Pro Leu Val Val Thr His
        195                 200                 205

Pro Gly Ser Gly Arg Lys Gly Leu Tyr Val Asn Gln Val Tyr Cys Gln
    210                 215                 220

Arg Ile Glu Gly Met Thr Asp Ala Glu Ser Lys Pro Leu Leu Gln Phe
225                 230                 235                 240

Leu Tyr Glu His Ala Thr Arg Phe Asp Phe Thr Cys Arg Val Arg Trp
                245                 250                 255

Lys Lys Asp Gln Val Leu Val Trp Asp Asn Leu Cys Thr Met His Arg
            260                 265                 270

Ala Val Pro Asp Tyr Ala Gly Lys Phe Arg Tyr Leu Thr Arg Thr Thr
        275                 280                 285

Val Gly Gly Val Arg Pro Ala Arg
    290                 295


<210> SEQ ID NO 14
```

<211> LENGTH: 20
<212> TYPE: DNA
<213> ORGANISM: Artificial Sequence
<220> FEATURE:
<223> OTHER INFORMATION: primer AtnilA1Fa
<220> FEATURE:
<221> NAME/KEY: misc_feature
<222> LOCATION: (9)..(9)
<223> OTHER INFORMATION: n is a, c, g, or t

<400> SEQUENCE: 14
gacagtccna atacsgaygg 20

<210> SEQ ID NO 15
<211> LENGTH: 26
<212> TYPE: DNA
<213> ORGANISM: Artificial Sequence
<220> FEATURE:
<223> OTHER INFORMATION: Primer AtnilA3R
<220> FEATURE:
<221> NAME/KEY: misc_feature
<222> LOCATION: (9)..(9)
<223> OTHER INFORMATION: n is a, c, g, or t

<400> SEQUENCE: 15
gtyttsagnc gsagsccscg rtcsgt 26

<210> SEQ ID NO 16
<211> LENGTH: 20
<212> TYPE: DNA
<213> ORGANISM: Artificial Sequence
<220> FEATURE:
<223> OTHER INFORMATION: Primer nilA2F

<400> SEQUENCE: 16
ccatcctcat aacaccagct 20

<210> SEQ ID NO 17
<211> LENGTH: 20
<212> TYPE: DNA
<213> ORGANISM: Artificial Sequence
<220> FEATURE:
<223> OTHER INFORMATION: Primer nilA2R

<400> SEQUENCE: 17
gcagatcatc gatacgacca 20

<210> SEQ ID NO 18
<211> LENGTH: 1796
<212> TYPE: DNA
<213> ORGANISM: Agrobacterium tumefaciens
<220> FEATURE:
<221> NAME/KEY: misc_feature
<223> OTHER INFORMATION: nilA locus

<400> SEQUENCE: 18
gcagatcatc gatacgacca atgacgttct ggccaaattc gattgacgac aatggcccgc 60
cgcgcttgcg gcggcgggct ctttatccgg ttgccgggtg acatgggcat tcccgccgat 120
tgttttcgcg ggacatgcac gaacaacgag aaacgagcat gaacgaaccc tctatcatcg 180
cgctttcggc gcgaacggcg gcgctttgcc tcgctgtacc cggtgcgcga tatcgcctgc 240
cgcagacggc atggcggctg acttcgcaag atggtgattt acgagccgga aaaaccgcca 300
ccgtggtgac gctgctgcat gatctgcgtc cggatacacg gtatctgttc gaagcggatg 360
ggttcgcaag cctggagttc aggacagcgc cctgcgcggg gcttgtcgag gcgacggcat 420

```
tttcgctgac gccggatatt gcgcttgacg acgaagccgg cgcacgcgcc aacgcccgcg    480

ctctggaaga ggcagttgcc gccgtgcctg cgggcggcac gttgcgattt gctgccggcc    540

tctggacagc gtttcccgtg cggttgaaaa gcgacatgac gtttcatctt gcggaagggg    600

ccgtgctgcg cgcaccctcc acccgcaatg gctggccgat cctgcctgcc cgcgatgaga    660

cgggccgcat gctcggcagt tgggaagggc taccggatgc ctgtttcgct gcgccggtcc    720

atgccatcgg cgcagataat ctcgtgatcg aaggcacagg cgtcctcgat ggttccggcg    780

acagaggcga ctggtggagc tggccgaaag aaacccgtga cggcgcgcgc cgaccgcgcg    840

gcctgcatct cgtctcctgc cgcaatgtcg ggcttttcgg tttcaccatt cgcaatgcac    900

cgtcctggac ggtccatcca caagggtgcg agaccctgac agcggcgggt ctcacaatca    960

gcgctccgca taacagcccc aataccgatg gtttcaaccc ggaaagctgc cgcaacgtga   1020

cgatatcagg cgtgcgcttt tcagtgggcg acgattgcat tgctgtgaag gcaggcaaac   1080

gcgggccgaa cggcgaggac gaccatctgg cggaaacacg cggcgtcagc gtgcgccatt   1140

gcctgatgga gcgcggccat ggcgggctgg tgatcggctc ggaaatgtcg ggtggcgtgc   1200

atgacgtaac cgtagaggac tgcgacatgg ttggcacgga tcgcggcttg cgtctcaaga   1260

cgcggcgggg ccgtggcggt tcagtcagcg atatcaccat gcgccgcgtg ttgctggatg   1320

gcgtgcatac cgcgctttcc gccaatgccc attaccattg cgatgccgat gggcatgacg   1380

gctgggtgca gtcgcgagac cctgcacctg tcgacgacgg gaccccgttt atcgacggaa   1440

ttactgtcga agatgtggaa atccgccatc tggcacatgc cgccggcgtc tttctcggtt   1500

tagcggaggc cccaatccgc aatatcgcca ttcgcaatct cacaatcgtc tcgcgtgatc   1560

ctgtagccgt ggccacaccg ccgatcatgg ccgatggggt gcgccccatg ctgcatgagg   1620

ggatcgtttt cgaacaggct gaaatcattt gcgacgatcc tgcgctgctg agcgcctctg   1680

ccgtttccca ctcacagatt tcaatcgaga aaacccatga aagccactga ttattttgat   1740

caattctcca gccgctatag gcactacaag ggcgggagct ggtgttatga ggatgg       1796
```

<210> SEQ ID NO 19
<211> LENGTH: 43
<212> TYPE: DNA
<213> ORGANISM: Artificial Sequence
<220> FEATURE:
<223> OTHER INFORMATION: Primer nilA5'

<400> SEQUENCE: 19

```
ccggctcttc cagctcctca tgcacgaaca acgagaaacg agc                        43
```

<210> SEQ ID NO 20
<211> LENGTH: 59
<212> TYPE: DNA
<213> ORGANISM: Artificial Sequence
<220> FEATURE:
<223> OTHER INFORMATION: Primer nilA_MCS_SOER

<400> SEQUENCE: 20

```
gaatggtgaa acctctagat taattaagga tccccgggta ccgaaaagcc cgacattgc      59
```

<210> SEQ ID NO 21
<211> LENGTH: 59
<212> TYPE: DNA
<213> ORGANISM: Artificial Sequence
<220> FEATURE:
<223> OTHER INFORMATION: Primer nilA_MCS_SOEF

<400> SEQUENCE: 21

```
gcaatgtcgg gcttttcggt acccggggat ccttaattaa tctagaggtt tcaccattc      59


<210> SEQ ID NO 22
<211> LENGTH: 32
<212> TYPE: DNA
<213> ORGANISM: Artificial Sequence
<220> FEATURE:
<223> OTHER INFORMATION: Primer nilA3'

<400> SEQUENCE: 22

ggaattctca gtggctttca tgggttttct cg                                  32


<210> SEQ ID NO 23
<211> LENGTH: 1626
<212> TYPE: DNA
<213> ORGANISM: Artificial Sequence
<220> FEATURE:
<223> OTHER INFORMATION: nilA MCS

<400> SEQUENCE: 23

catgcacgaa caacgagaaa cgagcatgaa cgaaccctct atcatcgcgc tttcggcgcg     60

aacggcggcg ctttgcctcg ctgtacccgg tgcgcgatat cgcctgccgc agacggcatg    120

gcggctgact tcgcaagatg gtgatttacg agccggaaaa accgccaccg tggtgacgct    180

gctgcatgat ctgcgtccgg atacacggta tctgttcgaa gcggatgggt tcgcaagcct    240

ggagttcagg acagcgccct gcgcggggct tgtcgaggcg acggcatttt cgctgacgcc    300

ggatattgcg cttgacgacg aagccggcgc acgcgccaac gcccgcgctc tggaagaggc    360

agttgccgcc gtgcctgcgg gcggcacgtt gcgatttgct gccggcctct ggacagcgtt    420

tcccgtgcgg ttgaaaagcg acatgacgtt tcatcttgcg gaaggggccg tgctgcgcgc    480

accctccacc cgcaatggct ggccgatcct gcctgcccgc gatgagacgg gccgcatgct    540

cggcagttgg gaagggctac cggatgcctg tttcgctgcg ccggtccatg ccatcggcgc    600

agataatctc gtgatcgaag gcacaggcgt cctcgatggt tccggcgaca gaggcgactg    660

gtggagctgg ccgaaagaaa cccgtgacgg cgcgcgccga ccgcgcggcc tgcatctcgt    720

ctcctgccgc aatgtcgggc ttttcggtac ccggggatcc ttaattaatc tagaggtttc    780

accattcgca atgcaccgtc ctggacggtc catccacaag ggtgcgagac cctgacagcg    840

gcgggtctca caatcagcgc tccgcataac agccccaata ccgatggttt caacccggaa    900

agctgccgca acgtgacgat atcaggcgtg cgcttttcag tgggcgacga ttgcattgct    960

gtgaaggcag gcaaacgcgg gccgaacggc gaggacgacc atctggcgga aacacgcggc   1020

gtcagcgtgc gccattgcct gatggagcgc ggccatggcg ggctggtgat cggctcggaa   1080

atgtcgggtg gcgtgcatga cgtaaccgta gaggactgcg acatggttgg cacggatcgc   1140

ggcttgcgtc tcaagacgcg gcggggccgt ggcggttcag tcagcgatat caccatgcgc   1200

cgcgtgttgc tggatggcgt gcataccgcg ctttccgcca atgcccatta ccattgcgat   1260

gccgatgggc atgacggctg ggtgcagtcg cgagaccctg cacctgtcga cgacgggacc   1320

ccgtttatcg acggaattac tgtcgaagat gtggaaatcc gccatctggc acatgccgcc   1380

ggcgtctttc tcggtttagc ggaggcccca atccgcaata tcgccattcg caatctcaca   1440

atcgtctcgc gtgatcctgt agccgtggcc acaccgccga tcatggccga tggggtgcgc   1500

cccatgctgc atgaggggat cgttttcgaa caggctgaaa tcatttgcga cgatcctgcg   1560

ctgctgagcg cctctgccgt ttcccactca cagatttcaa tcgagaaaac ccatgaaagc   1620
```

cactga 1626

<210> SEQ ID NO 24
<211> LENGTH: 9093
<212> TYPE: DNA
<213> ORGANISM: Agrobacterium tumefaciens
<220> FEATURE:
<221> NAME/KEY: misc_feature
<223> OTHER INFORMATION: nilA genomic region

<400> SEQUENCE: 24

```
ggcggcttat gccttcgcgc gcttcgattt tccgctgaag aaaatcctgt ttggctcggt     60
catcgccatc ctgcttttgc ccaatgtcgt aacccgcatt ccgcaatata tcctgttccg    120
tgacctcggc tggctggata gtttcctgcc gctatgggtt ccctcggcac tagccggtga    180
cgccttttc gtctttatgc ttgtgcagtt cctgcgctcg ctgccctcgg atatggagga    240
agccgcccgt gtggatggcg ccaacagtct gcagacgctg gtctacatcg tcgtgccgat    300
gctggcgccg gcgctgatct cggtctgcct tttccagttc atgtggacga tgaacgactt    360
tctgggaccg ctgatctacc tgtcctcggt cgataaatat ccggtgagcc tggcgctcaa    420
actctccatc gacaccaccg aagccttcga atggaaccgc atcctggcga tgtcggtgct    480
gacgatcgcg cctgcgctcg tcgtgttttt cgcggcgcaa cggtatttca ttgaagggat    540
ctcgtctggc gggatcaagg gctgaaaatg gcaagcgttc aacttaaaaa tctcgaaaaa    600
gtctatggcg gcagcttcaa ggccgtgcac ggcatcaatc tcgaaatcga ggacggcgag    660
ttcatggtct tcgtcggccc gtccggctgc gccaaatcca ccacgctgcg catggtggcg    720
gggctggagg aaatcaccgg cggtgaaatc ctcatcggag atcagcgcgt caacgacctg    780
ccgcccggca agcgctccat tgccatggtg ttccagaact atgcgctcta tccgcatatg    840
aaggtgcgcg gcaatcttgc tttcggtctc aagattgccg gtgttgccaa gcccgagatc    900
gagaaggcaa tcgacaatgt cgcgcgcatt ctcgaaatcg agcccttgct ggatcgcctg    960
ccgaaatcag ctttccggcg ggcaggcgca acgtgttgct ttgggccgtg ccctcatcaa   1020
gaaaccgggc gtgttcctgt tcgatgagcc cctttcgaat ctcgatgcga agctgcgcgc   1080
ttccatgcgt gtgcgcatta ccgatctgca tcgccagctg aaggcggagg gcctgtcttc   1140
gaccgtcgtc tacgtgacgc acgatcagac ggaagccatg accatgggcg accgtatctg   1200
cgtcatgcag gccgggcgca tcatgcaggt cgccacgccg aaggaactct acaaccggcc   1260
cgccaatctg ttcgtcgccg gtttcattgg catgccggaa atgaaccttg tggatgtggc   1320
gatcgacggg gcggagttcg tcatcggtgg gcaacgtctt ccgatagggg accatctgga   1380
aaagcggctt tcagccagac cggcggacgc cgtcatcggc atccgtccgc agcatctttc   1440
gttagccggt gaggccgatg ggcctgcgct gcaggctaaa ctgaccaacg ccgaattcat   1500
ggggcacgag gtctatctgc atgccgatct gggcggacag aagctcgtga gcgtggtggg   1560
agcagccgaa ttcgaggcgc ttgggcgcga cggcattctg cgactgaagc cggaccccga   1620
gaagctgcat attttcgaca aggccgatgg ccgcaatgtc tcgctgtgag gaggggacga   1680
gcgtgcctga tttttcgagg aggagaagaa caatgaagat gacgacgatg acgagaacaa   1740
tggcgatgct ggccggcgct gcctatctgg ccacggtggc tgcgcctgcg gcgggtgccg   1800
cggaactgcg tatgtcgtgg tggggcggcg aaagccgtca tgtcgccact cagaaggcga   1860
ttgccgcctg cggtgaaaaa tacagccaca cggtcaaagg tgaatttacc ggcttcgatg   1920
gatatctgga aaaactgacc acgcaaatgg caggcaagac ggaggctgat atcgttcagg   1980
```

```
tgaactggcc atggatgccg ctgttttcca agaatggtga aggttttgct gatctgcgtc   2040
agctgaaacc tctcgatctt tcgcaatggg ccgagacgga tctggaagcg ggttctatga   2100
acggggtgct tcagggcctt tcagtctcca ccaccggccg cgtgtttttt ttcaacgcca   2160
ccaccttcga gaaggctggc gttgaaatcc ccaagacatg ggatgaattc ttcgcggcaa   2220
caaaaaccat caaggaaaag ctcggcaagg atcattacac cttcaatgcc gtaaaggaga   2280
ctgcccagct tctcgtgaca ctcgccgtgg tgcagaaaac cggaaacgat ctggtcgacc   2340
ccaagaccaa ccgtgtcgcc tggacgccgg aggaactggc ggaaggtatc tcgttcgtcg   2400
gcaagctggt ggaaaccggc tccattcgct cccagaaaga ggaagcggcc gatggcaacg   2460
tcaatcttta tgaaaagccg tcgtggtccg aaggccgtat cgctggttcc tatgaatggg   2520
attccaccta ttcgaaatat gccgatcccc tgaaggatgg gcaggtgctg aaacccgtgc   2580
cgatgctgaa gcttgccgat gccgtaacgg aaggcgttta tcgcaagcct tccatggtct   2640
tttctatctc gaaaaactcg aagaaccctg aagcggcagc gcaaatcctg aactgcctgc   2700
tgaacgagcc tgagggcatc gatgcgcttg gcacgtctcg cggcctgcct gcttccaagg   2760
ctgcggcgca gcgtctgggc gacaagggtg agccggaagt gcgcgccgcc aacgccatcg   2820
tcatggcggc atctggaccg gtagtttcgc ccttcaacga acatccggaa atccgctccg   2880
gcttcatcga tacgctggag gaatatgcct atggccagct gacggcggaa gaggcggcag   2940
atcatcgata cgaccaatga cgttctggcc aaattcgatt gacgacaatg gcccgccgcg   3000
cttgcggcgg cgggctcttt atccggttgc cgggtgacat gggcattccc gccgattgtt   3060
ttcgcgggac atgcacgaac aacgagaaac gagcatgaac gaaccctcta tcatcgcgct   3120
ttcggcgcga acggcggcgc tttgcctcgc tgtacccggt gcgcgatatc gcctgccgca   3180
gacggcatgg cggctgactt cgcaagatgg tgatttacga gccggaaaaa ccgccaccgt   3240
ggtgacgctg ctgcatgatc tgcgtccgga tacacggtat ctgttcgaag cggatgggtt   3300
cgcaagcctg gagttcagga cagcgccctg cgcggggctt gtcgaggcga cggcattttc   3360
gctgacgccg gatattgcgc ttgacgacga agccggcgca cgcgccaacg cccgcgctct   3420
ggaagaggca gttgccgccg tgcctgcggg cggcacgttg cgatttgctg ccggcctctg   3480
gacagcgttt cccgtgcggt tgaaaagcga catgacgttt catcttgcgg aaggggccgt   3540
gctgcgcgca ccctccaccc gcaatggctg gccgatcctg cctgcccgcg atgagacggg   3600
ccgcatgctc ggcagttggg aagggctacc ggatgcctgt ttcgctgcgc cggtccatgc   3660
catcggcgca gataatctcg tgatcgaagg cacaggcgtc ctcgatggtt ccggcgacag   3720
aggcgactgg tggagctggc cgaaagaaac ccgtgacggc gcgcgccgac cgcgcggcct   3780
gcatctcgtc tcctgccgca atgtcgggct tttcggtttc accattcgca atgcaccgtc   3840
ctggacggtc catccacaag ggtgcgagac cctgacagcg gcgggtctca caatcagcgc   3900
tccgcataac agccccaata ccgatggttt caacccggaa agctgccgca acgtgacgat   3960
atcaggcgtg cgcttttcag tgggcgacga ttgcattgct gtgaaggcag gcaaacgcgg   4020
gccgaacggc gaggacgacc atctggcgga aacacgcggc gtcagcgtgc gccattgcct   4080
gatggagcgc ggccatggcg ggctggtgat cggctcggaa atgtcgggtg gcgtgcatga   4140
cgtaaccgta gaggactgcg acatggttgg cacggatcgc ggcttgcgtc tcaagacgcg   4200
gcggggccgt ggcggttcag tcagcgatat caccatgcgc cgcgtgttgc tggatggcgt   4260
gcataccgcg ctttccgcca atgcccatta ccattgcgat gccgatgggc atgacggctg   4320
ggtgcagtcg cgagaccctg cacctgtcga cgacgggacc ccgtttatcg acggaattac   4380
```

```
tgtcgaagat gtggaaatcc gccatctggc acatgccgcc ggcgtctttc tcggtttagc   4440
ggaggcccca atccgcaata tcgccattcg caatctcaca atcgtctcgc gtgatcctgt   4500
agccgtggcc acaccgccga tcatggccga tggggtgcgc cccatgctgc atgaggggat   4560
cgttttcgaa caggctgaaa tcatttgcga cgatcctgcg ctgctgagcg cctctgccgt   4620
ttcccactca cagatttcaa tcgagaaaac ccatgaaagc cactgattat tttgatcaat   4680
tctccagccg ctataggcac tacaagggcg ggagctggtg ttatgaggat ggggggtttg   4740
cagcacctgt tcgaagcgac cggcgaccgg cgctggaacg aacatctgca tcgtctggct   4800
gacacccaga tagcggcaga cggagtgctc gccggttacg atccgcagga atacaatatc   4860
gatcacatcc tcgccggtcg cattctgttt cctctggcag cggaaacggg cgatccacgt   4920
tatctcgctg cggcggaaca tcttgcgggc caactccgca gccatccgcg tacgggcgcc   4980
ggtaattatt ggcacaagaa gcgttatccg catcaggtct ggctggatgg cctttatatg   5040
ggacttcctt tccagatcga atatgcgcag gcgactagtg acgccgaact tatcgacgat   5100
gcgctacagc aattctcaac cgcactcacg ctgacggcgg atgccggtgg gctctatgtc   5160
catggttatg acgaaagccg caaccagcgc tgggccgatc ccgtgagcgg ccaatccccg   5220
gcggtatggg cccgcgccgt cggctggctc gccatggcgc tggtcgatgc gttggtgatg   5280
ttgccggctg atggcgcaac gatcggactt cgggaacgcg cgggcctgct tctggccggt   5340
attgttgccc ggcagactaa aaccggtctc tggatgcagg tttggacaaa ccggatcttg   5400
ccggaaacta cgaggaaacc tccgcttcgg cgatgttcgc ctatgcctta ctgcgggctg   5460
cgcggttggg gcttttgcag ggagaggaag caaatgcggc tctttcggcg ggccggtccg   5520
cgcttgaggc cctgcttgag agacagctca aggtggacga aaagggtatc gtccgtctca   5580
ccggcatcgt gcatgtcgcg ggcctcggcg gtttcgaggg caattatcgc gatgggtctc   5640
cggattatta cctgaccgag ccggttgtat ccgatgacgc caaaggcgtc gggccgctga   5700
tgatggccta tgccgaaagc ctgcttttgg catgacggcg cggtcatctt aacgggcaca   5760
gggtgttttg tggcatgaga tcatgccact tttgccaaga tcaccgtctg gatcaggccc   5820
tgttttttgt ggttcgcgat tgtgatcgtg ccaccgaagc gctcgatgat ttctctggcg   5880
atggctagac ccaaccccac accagggatc gactttcgcc gcccgagatc gacccgaaag   5940
aagggctcga aaatccggcc gatcagttcc tgcggaatgc cagggccttc atcgcggatt   6000
gtaacgacga cctcgctctc gtcctcggtt agatcgatcc gtgccgtttt gtccatgggt   6060
gacggcattg aggatgaggt tgcgcaaggc tcttttaagc gcaagtggag cggccttgat   6120
gatcatggcg gcttccggtt tcataaagtc gagcgcatca gcgtaaccga gatcagaaag   6180
ttcgctaacg atttcgccga gaagcctgcc gatatcgatc atcttgacgg tatcctggct   6240
cacttcctcg cgcacaagca gaatggcgct atccgcgatg gcgttcagtt cctcgaggtc   6300
cgccagccat ttgccccgct cttcgtcgtt ttcgatgaat tctgcccgca gacgcatgcg   6360
ggtcattggg gttctcaagt catggccagc ggctgcgacg aggcgcattc ggctttccca   6420
ttgccgcctt caggcggcgg gcgagttcgt tcaaggcccg cgccgtggcg cggatttcac   6480
ccggacctgt ttccgacaaa tggggtagcg aaccatcggg tccgatgctt gcagcggcgt   6540
tttccagcat gtcgaggggg cgggtgatct ttctggcggc gaagatggaa acagcagcac   6600
tgccaagaat gatcagcccg atccacatgc cgaaaatctt ccagccgccc gggggaggac   6660
ccatatgcgg aatttccgcg accagccatc cgctttttttc cagcgctata gccgccaccg   6720
```

-continued

```
gggcattact tccaggcgcg cggatcacaa ttgcggtgcg cggctcgcca acctgtgcaa   6780
gggccttttc tagaaactcc gaaagcattc cgtcaagatc accttcaggc ggcttctgtt   6840
caatgcggaa atagccgggt tgttgcagcg aggggtcgcg ttcggccatg gtcacggcaa   6900
aggcaaggct gcgggcaacg ggctcgatgg tggcatctgg cggcggcggc tgcaatgtct   6960
gatctgccac cacagttgca agcgcgatga ccgcgatgat ggagacgatc aacagtgcgg   7020
cgatacggtt tctgagcgag ctcatcgatg caccggcagg gttctgacct gaaccgtcat   7080
ctggtaaccg ccattgcgaa cggttttgaa gatcggagcc cgggcatcgg tttcgagctt   7140
cttgcgcaac cggctcatca acacgtcgac ggagcggtcg aacggtccgc ggtccttgcc   7200
ctgcgtaaga tcgagcagct gatcgcggga aagaagccgg ccgggcctgt cgaggaagac   7260
tttcagcaga tcgaactccg cccccgtcag ctcgatcctc tcaccgctgg cgtggatgac   7320
ggagcgctgt tccggatcgg cggtgaagtc cgaaaaacca taagcggtgg atgagccgcg   7380
aggtacttcc tgaggtactg cgcggcgcag cacggccttg atccgcgccg tcagttctcg   7440
cggattgaag ggtttgccaa gatagtcgtc ggcgccaatt tccagcccaa cgatccggtc   7500
gacatcctcc ttgagcgctg tcaggagaat gacgggcgtg cgcggccggc ggccttggag   7560
atcgcggcag atatcgaggc cggaaccatc cggcagcatc acgtcgagca cgatgagatc   7620
gggatcggag caggcgaact gttcttcgaa ctcacgcctg tcggctgcca tagaaacgcg   7680
aaacccctgc gagccgagat atttcgcgag caatgtacgt atctccggat catcatccac   7740
gatcaaaata tgtgtcaccg aaactgtcgc catatcatcc aacctttga tgccactata   7800
cataagcgga gcaaagaaac ggcggatttt tgcaacgaaa gcttgctggg acgctctggc   7860
aacattcggt tacaaatagg ccgcgcgtgg aacaagaccc gcaacattgg gaccaaagcc   7920
ggaaacgctt agctcctatc gtcttctcag gttggaaaac gaaaaggaag gtaagatgag   7980
aaacgctcta atcgccaccg ccgtcgtcgt gacaactgtt cttggcgctt cggccacctc   8040
ccgggctgcg gagcagggtg aaccagtgcc gcaggcatcg gaacaggcca tgccgccgct   8100
ggccagtcct gacttcggtt cgaatagtgg tccggagcaa aggctgccgc atggccgcaa   8160
gatggccggg cctgagatgc tacgcccgga tatgatgggg ccggatatat tgggcccgga   8220
tatattgggg ttggcgacga aactttcggc agcggaaatc tatctcggcg tcacacctga   8280
acagcttggt ccgtggcgcg ctcagccgtg cgtcacttta catcgccggc gtcggcatgg   8340
tcgccatgac ccttatcgtc ggctggcagg tgtttgcccg ttatatcctg aatgattcac   8400
caagttggtc cgagccgctg tcgcttcacc ttatgtcatg gttcatcatg ctgggggcgg   8460
cggtgggcgt gcgtgaaagc gtgcatctgg ggctggatat tctgcgctat atgatgccgc   8520
cgcgcataca ggcggcgatg gacctgacca gtctggcact gatcttcttt ttcggggttg   8580
gcatgtgctg gtacggaacc gtcctctctg ccggaacatg gacggcgacg atccctgttc   8640
ttggatggcc gggcggcatg gatttcttcc cgctgatcgg tggcggtttt ctgatcgcgc   8700
tgtttgcagc cgaacgcttt atcgatcttg ccatcggcga ggaaatcgcg gcggatgtgt   8760
ttgtgcagga ggccgcgtaa atggcttaca caatcctctt cggtgtcttc acccttctga   8820
tgctgatcgg tacgccgatt gcgttctgcc tcggcattgc ctccttcgcc accgtcttta   8880
tctcggcctg ccgcccatag tggtcttcca gcagatgaac tccggcatga acgtgtttgc   8940
gatgatggcg atcccgttct tcatcttcgc gggtgacctc atggtccgcg gcggtatagc   9000
ccatcgtctg atccgttttt gcggccggtc ttgtcggtca tctgcgcggc ggtctggggc   9060
aggtcaacat cgtcgcttcg acattgtccg gcg                                9093
```

<210> SEQ ID NO 25
<211> LENGTH: 26644
<212> TYPE: DNA
<213> ORGANISM: Artificial Sequence
<220> FEATURE:
<223> OTHER INFORMATION: Plasmid pDAB9698

<400> SEQUENCE: 25

```
ttgtacaaag tggtgatgat ccggctgcta acaaagcccg aaaggaagct gagttggctg     60
ctgccaccgc tgagcaataa ctagcataac cccttggggc ctctaaacgg gtcttgaggg    120
gttttttgct gaaaggagga actatatccg gatatccaca ggacgggtgt ggtcgccatg    180
atcgcgtagt cgatagtggc tccaagtagc gaagcgagca ggactgggcg gcggccaaag    240
cggtcggaca gtgctccgag aacgggtgcg catagaaatt gcatcaacgc atatagcgct    300
agcagcacgc catagtgact ggcgatgctg tcggaatgga cgatatcccg caagaggccc    360
ggcagtaccg gcataaccaa gcctatgcct acagcatcca gggtgacggt gccgaggatg    420
acgatgagcg cattgttaga tttcatacac ggtgcctgac tgcgttagca atttaactgt    480
gataaactac cgcattaaag cttatcgatg ataagctgtc aaacatgaga attcttgaag    540
acgaaagggc ctcgtgatac gcctattttt ataggttaat gtcatgataa taatggtttc    600
ttagacgtca ggtggcactt ttcggggaaa tgtgcgcgga acccctattt gtttattttt    660
ctaaatacat tcaaatatgt atccgctcat gagacaataa ccctgataaa tgcttcaata    720
atattgaaaa aggaagagta tgagtattca acatttccgt gtcgccctta ttcccttttt    780
tgcggcattt tgccttcctg tttttgctca cccagaaacg ctggtgaaag taaaagatgc    840
tgaagatcag ttgggtgcac gagtgggtta catcgaactg gatctcaaca gcggtaagat    900
ccttgagagt tttcgccccg aagaacgttt tccaatgatg agcactttta aagttctgct    960
atgtggcgcg gtattatccc gtgttgacgc cgggcaagag caactcggtc gccgcataca   1020
ctattctcag aatgacttgg ttgagtactc accagtcaca gaaaagcatc ttacggatgg   1080
catgacagta agagaattat gcagtgctgc cataaccatg agtgataaca ctgcggccaa   1140
cttacttctg acaacgatcg gaggaccgaa ggagctaacc gcttttttgc acaacatggg   1200
ggatcatgta actcgccttg atcgttggga accggagctg aatgaagcca taccaaacga   1260
cgagcgtgac accacgatgc ctgcagcaat ggcaacaacg ttgcgcaaac tattaactgg   1320
cgaactactt actctagctt cccggcaaca attaatagac tggatggagg cggataaagt   1380
tgcaggacca cttctgcgct cggcccttcc ggctggctgg tttattgctg ataaatctgg   1440
agccggtgag cgtgggtctc gcggtatcat tgcagcactg gggccagatg gtaagccctc   1500
ccgtatcgta gttatctaca cgacggggag tcaggcaact atggatgaac gaaatagaca   1560
gatcgctgag ataggtgcct cactgattaa gcattggtaa ctgtcagacc aagtttactc   1620
atatatactt tagattgatt taaaacttca tttttaattt aaaaggatct aggtgaagat   1680
cctttttgat aatctcatga ccaaaatccc ttaacgtgag ttttcgttcc actgagcgtc   1740
agaccccgta gaaaagatca aaggatcttc ttgagatcct ttttttctgc gcgtaatctg   1800
ctgcttgcaa acaaaaaaac caccgctacc agcggtggtt tgtttgccgg atcaagagct   1860
accaactctt tttccgaagg taactggctt cagcagagcg cagataccaa atactgtcct   1920
tctagtgtag ccgtagttag gccaccactt caagaactct gtagcaccgc ctacatacct   1980
cgctctgcta atcctgttac cagtggctgc tgccagtggc gataagtcgt gtcttaccgg   2040
```

```
gttggactca agacgatagt taccggataa ggcgcagcgg tcgggctgaa cggggggttc   2100
gtgcacacag cccagcttgg agcgaacgac ctacaccgaa ctgagatacc tacagcgtga   2160
gctatgagaa agcgccacgc ttcccgaagg gagaaaggcg gacaggtatc cggtaagcgg   2220
cagggtcgga acaggagagc gcacgaggga gcttccaggg ggaaacgcct ggtatcttta   2280
tagtcctgtc gggtttcgcc acctctgact tgagcgtcga tttttgtgat gctcgtcagg   2340
ggggcggagc ctatggaaaa acgccagcaa cgcggccttt ttacggttcc tggccttttg   2400
ctggcctttt gctcacatgt tctttcctgc gttatcccct gattctgtgg ataaccgtat   2460
taccgccttt gagtgagctg ataccgctcg ccgcagccga acgaccgagc gcagcgagtc   2520
agtgagcgag gaagcggaag agcgcctgat gcggtatttt ctccttacgc atctgtgcgg   2580
tatttcacac cgcatatatg gtgcactctc agtacaatct gctctgatgc cgcatagtta   2640
agccagtata cactccgcta tcgctacgtg actgggtcat ggctgcgccc cgacacccgc   2700
caacacccgc tgacgcgccc tgacgggctt gtctgctccc ggcatccgct tacagacaag   2760
ctgtgaccgt ctccgggagc tgcatgtgtc agaggttttc accgtcatca ccgaaacgcg   2820
cgaggcagct gcggtaaagc tcatcagcgt ggtcgtgaag cgattcacag atgtctgcct   2880
gttcatccgc gtccagctcg ttgagtttct ccagaagcgt taatgtctgg cttctgataa   2940
agcgggccat gttaagggcg gtttttttcct gtttggtcac tgatgcctcc gtgtaagggg   3000
gatttctgtt catgggggta atgataccga tgaaacgaga gaggatgctc acgatacggg   3060
ttactgatga tgaacatgcc cggttactgg aacgttgtga gggtaaacaa ctggcggtat   3120
ggatgcggcg ggaccagaga aaaatcactc agggtcaatg ccagcgcttc gttaatacag   3180
atgtaggtgt tccacagggt agccagcagc atcctgcgat gcagatccgg aacataatgg   3240
tgcagggcgc tgacttccgc gtttccagac tttacgaaac acggaaaccg aagaccattc   3300
atgttgttgc tcaggtcgca gacgttttgc agcagcagtc gcttcacgtt cgctcgcgta   3360
tcggtgattc attctgctaa ccagtaaggc aaccccgcca gcctagccgg gtcctcaacg   3420
acaggagcac gatcatgcgc acccgtggcc aggacccaac gctgcccgag atgcgccgcg   3480
tgcggctgct ggagatggcg gacgcgatgg atatgttctg ccaagggttg gtttgcgcat   3540
tcacagttct ccgcaagaat tgattggctc caattcttgg agtggtgaat ccgttagcga   3600
ggtgccgccg gcttccattc aggtcgaggt ggcccggctc catgcaccgc gacgcaacgc   3660
ggggaggcag acaaggtata gggcggcgcc tacaatccat gccaacccgt tccatgtgct   3720
cgccgaggcg gcataaatcg ccgtgacgat cagcggtcca gtgatcgaag ttaggctggt   3780
aagagccgcg agcgatcctt gaagctgtcc ctgatggtcg tcatctacct gcctggacag   3840
catggcctgc aacgcgggca tcccgatgcc gccggaagcg agaagaatca taatggggaa   3900
ggccatccag cctcgcgtcg cgaacgccag caagacgtag cccagcgcgt cggccgccat   3960
gccggcgata atggcctgct tctcgccgaa acgtttggtg gcgggaccag tgacgaaggc   4020
ttgagcgagg gcgtgcaaga ttccgaatac cgcaagcgac aggccgatca tcgtcgcgct   4080
ccagcgaaag cggtcctcgc cgaaaatgac ccagagcgct gccggcacct gtcctacgag   4140
ttgcatgata aagaagacag tcataagtgc ggcgacgata gtcatgcccc gcgcccaccg   4200
gaaggagctg actgggttga aggctctcaa gggcatcggt cgatcgacgc tctcccttat   4260
gcgactcctg cattaggaag cagcccagta gtaggttgag gccgttgagc accgccgccg   4320
caaggaatgg tgcatgcaag gagatggcgc ccaacagtcc cccggccacg gggcctgcca   4380
ccatacccac gccgaaacaa gcgctcatga gcccgaagtg gcgagcccga tcttccccat   4440
```

```
cggtgatgtc ggcgatatag gcgccagcaa ccgcacctgt ggcgccggtg atgccggcca   4500
cgatgcgtcc ggcgtagagg atcgagatct cgatcccgcg aaattaatac gactcactat   4560
agggagacca caacggtttc cctctagatc acaagtttgt acaaaaaagc aggctccgaa   4620
ttcgccctta gctttcgttg caaaaatccg ccgtttcttt gctccgctta tgtatagtgg   4680
catcaaaagg ttggatgata tggcgacagt ttcggtgaca catattttga tcgtggatga   4740
tgatccggag atacgtacat tgctcgcgaa atatctcggc tcgcaggggt ttcgcgtttc   4800
tatggcagcc gacaggcgtg agttcgaaga acagttcgcc tgctccgatc ccgatctcat   4860
cgtgctcgac gtgatgctgc cggatggttc cggcctcgat atctgccgcg atctccaagg   4920
ccgccggccg cgcacgcccg tcattctcct gacagcgctc aaggaggatg tcgaccggat   4980
cgttgggctg gaaattggcg ccgacgacta tcttggcaaa cccttcaatc cgcgagaact   5040
gacggcgcgg atcaaggccg tgctgcgccg cgcagtacct caggaagtac ctcgcggctc   5100
atccaccgct tatggttttt cggacttcac cgccgatccg gaacagcgct ccgtcatcca   5160
cgccagcggt gagaggatcg agctgacggg ggcggagttc gatctgctga aagtcttcct   5220
cgacaggccc ggccggcttc tttcccgcga tcagctgctc gatcttacgc agggcaagga   5280
ccgcggaccg ttcgaccgct ccgtcgacgt gttgatgagc cggttgcgca agaagctcga   5340
aaccgatgcc cgggctccga tcttcaaaac cgttcgcaat ggcggttacc agatgacggt   5400
tcaggtcaga accctgccgg tgcatcgatg agctcgctca gaaaccgtat cgccgcactg   5460
ttgatcgtct ccatcatcgc ggtcatcgcg cttgcaactg tggtggcaga tcagacattg   5520
cagccgccgc cgccagatgc caccatcgag cccgttgccc gcagccttgc ctttgccgtg   5580
accatggccg aacgcgaccc ctcgctgcaa caacccggct atttccgcat tgaacagaag   5640
ccgcctgaag gtgatcttga cggaatgctt tcggagtttc tagaaaaggc ccttgcacag   5700
gttggcgagc cgcgcaccgc aattgtgatc cgcgcgcctg gaagtaatgc cccggtggcg   5760
gctatagcgc tggaaaaaag cggatggctg gtcgcggaaa ttccgcatat gggtcctccc   5820
ccgggcggct ggaagatttt cggcatgtgg atcgggctga tcattcttgg cagtgctgct   5880
gtttccatct tcgccgccag aaagatcacc cgccccctcg acatgctgga aaacgccgct   5940
gcaagcatcg gacccgatgg ttcgctaccc catttgtcgg aaacaggtcc gggtgaaatc   6000
cgcgccacgg cgcgggcctt gaacgaactc gcccgccgcc tgaaggcggc aatgggaaag   6060
ccgaatgcgc ctcgtcgcag ccgctggcca tgacttgaga accccaatga cccgcatgcg   6120
tctgcgggca gaattcatcg aaaacgacga agagcggggc aaatggctgg cggacctcga   6180
ggaactgaac gccatcgcgg atagcgccat tctgcttgtg cgcgaggaag tgagccagga   6240
taccgtcaag atgatcgata tcggcaggct tctcggcgaa atcgttagcg aactttctga   6300
tctcggttac gctgatgcgc tcgactttat gaaaccggaa gccgccatga tcatcaaggc   6360
cgctccactt gcgcttaaaa gagccttgcg caacctcatc ctcaatgccg tcacccatgg   6420
acaaaacggc acggatcgat ctaaccgagg acgagagcga ggtcgtcgtt acaatccgcg   6480
atgaaggccc tggcattccg caggaactga tcggccggat tttcgagccc ttctttcggg   6540
tcgatctcgg gcggcgaaag tcgatccctg gtgtggggtt gggtctagcc atcgccagag   6600
aaatcatcga gcgcttcggt ggcacgatca caatcgcgaa ccacaaaaaa cagggcctga   6660
tccagacggt gatcttggca aaagtggcat gatctcatgc cacaaaacac cctgtgcccg   6720
ttaagatgac cgcgccgtca tgccaaaagc aggctttcgg cataggccat catcagcggc   6780
```

-continued

```
ccgacgcctt tggcgtcatc ggatacaacc ggctcggtca ggtaataatc cggagaccca   6840
tcgcgataat tgccctcgaa accgccgagg cccgcgacat gcacgatgcc ggtgagacgg   6900
acgataccct tttcgtccac cttgagctgt ctctcaagca gggcctcaag cgcggaccgg   6960
cccgccgaaa gagccgcatt tgcttcctct ccctgcaaaa gccccaaccg cgcagcccgc   7020
agtaaggcat aggcgaacat cgccgaagcg gaggtttcct cgtagtttcc ggcaagatcc   7080
ggtttgtcca aacctgcatc cagagaccgg ttttagtctg ccgggcaaca ataccggcca   7140
gaagcaggcc cgcgcgttcc cgaagtccga tcgttgcgcc atcagccggc aacatcacca   7200
acgcatcgac cagcgccatg gcgagccagc cgacggcgcg ggcccatacc gccggggatt   7260
ggccgctcac gggatcggcc cagcgctggt tgcggctttc gtcataacca tggacataga   7320
gcccaccggc atccgccgtc agcgtgagtg cggttgagaa ttgctgtagc gcatcgtcga   7380
taagttcggc gtcactagtc gcctgcgcat attcgatctg gaaaggaagt cccatataaa   7440
ggccatccag ccagacctga tgcggataac gcttcttgtg ccaataatta ccggcgcccg   7500
tacgcggatg gctgcggagt tggcccgcaa gatgttccgc cgcagcgaga taacgtggat   7560
cgcccgtttc cgctgccaga ggaaacagaa tgcgaccggc gaggatgtga tcgatattgt   7620
attcctgcgg atcgtaaccg gcgagcactc cgtctgccgc tatctgggtg tcagccagac   7680
gatgcagatg ttcgttccag cgccggtcgc cggtcgcttc gaacaggtgc tgcaaacccc   7740
ccatcctcat aacaccagct cccgcccttg tagtgcctat agcggctgga gaattgatca   7800
aaataatcag tggctttcat gggttttctc gattgaaatc tgtgagtggg aaacggcaga   7860
ggcgctcagc agctgcaggc gcgccaggcc ggcctgcgat cgctgtttaa acgtcgactt   7920
aattaagccc gggcatttta cactccgcta tcgctacgtg actgggtcat ggctgcgccc   7980
cgacacccgc caacacccgc tgacgcgccc tgacgggctt gtctgctccc ggcatccgct   8040
tacagacaag ctgtgaccgt ctccgggagc tgcatgtgtc agaggttttc accgtcatca   8100
ccgaaacgcg cgaggcagct gctcgcgcag gctgggtgcc aagctctcgg gtaacatcaa   8160
ggcccgatcc ttggagccct tgccctcccg cacgatgatc gtgccgtgat cgaaatccag   8220
atccttgacc cgcagttgca aaccctcact gatccgcatg cccgttccat acagaagctg   8280
ggcgaacaaa cgatgctcgc cttccagaaa accgaggatg cgaaccactt catccggggt   8340
cagcaccacc ggcaagcgcc gcgacggccg aggtcttccg atctcctgaa gccagggcag   8400
atccgtgcac agcaccttgc cgtagaagaa cagcaaggcc gccaatgcct gacgatgcgt   8460
ggagaccgaa accttgcgct cgttcgccag ccaggacaga aatgcctcga cttcgctgct   8520
gcccaaggtt gccgggtgac gcacaccgtg gaaacggatg aaggcacgaa cccagttgac   8580
ataagcctgt tcggttcgta aactgtaatg caagtagcgt atgcgctcac gcaactggtc   8640
cagaaccttg accgaacgca gcggtggtaa cggcgcagtg gcggttttca tggcttgtta   8700
tgactgtttt tttgtacagt ctatgcctcg ggcatccaag cagcaagcgc gttacgccgt   8760
gggtcgatgt ttgatgttat ggagcagcaa cgatgttacg cagcagggca gtcgccctaa   8820
aacaaagtta ggcatcacaa agtacagcat cgtgaccaac agcaccgatt ccgtcacact   8880
gcgcctcatg actgagcatg accttgcgat gctctatgag tggctaaatc gatctcatat   8940
cgtcgagtgg tggggcggag aagaagcacg cccgacactt gctgacgtac aggaacagta   9000
cttgccaagc gttttagcgc aagagtccgt cactccatac attgcaatgc tgaatggaga   9060
gccgattggg tatgcccagt cgtacgttgc tcttggaagc ggggacggat ggtgggaaga   9120
agaaaccgat ccaggagtac gcggaataga ccagtcactg gcgaatgcat cacaactggg   9180
```

```
caaaggcttg ggaaccaagc tggttcgagc tctggttgag ttgctgttca atgatcccga   9240
agtcaccaag atccaaacgg acccgtcgcc gagcaacttg cgagcgatcc gatgctacga   9300
gaaagcgggg tttgagaggc aaggtactgt aaccacccca gatggtccag ccgtgtacat   9360
ggttcaaaca cgccaggcat tcgagcgaac acgcagtgat gcctaaccct tccatcgagg   9420
gggacgtcca agggctggcg cccttggccg cccctcatgt caaacgttag acatcatgac   9480
ccgggtagac ggatggaagt ctagccctgc tcaatatgaa atcaacagta catttacagt   9540
caatactgaa tatacttgct acatttgcaa ttgtcttata acgaatgtga aataaaaata   9600
gtgtaacaac gcttttactc atcgataatc acaaaaacat ttatacgaac aaaaatacaa   9660
atgcactccg gtttcacagg ataggcggga tcagaatatg caacttttga cgttttgttc   9720
tttcaaaggg ggtgctggca aaaccaccgc actcatgggc ctttgcgctg ctttggcaaa   9780
tgacggtaaa cgagtggccc tctttgatgc cgacgaaaac cggcctctga cgcgatggag   9840
agaaaacgcc ttacaaagca gtactgggat cctcgctgtg aagtctattc cgccgacgaa   9900
atgccccttc ttgaagcagc ctatgaaaat gccgagctcg aaggatttga ttatgcgttg   9960
gccgatacgc gtggcggctc gagcgagctc aacaacacaa tcatcgctag ctcaaacctg  10020
cttctgatcc ccaccatgct aacgccgctc gacatcgatg aggcactatc tacctaccgc  10080
tacgtcatcg agctgctgtt gagtgaaaat ttggcaattc ctacagctgt tttgcgccaa  10140
cgcgtcccgg tcggccgatt gacaacatcg caacgcagga tgtcagagac gctagagagc  10200
cttccagttg taccgtctcc catgcatgaa agagatgcat ttgccgcgat gaaagaacgc  10260
ggcatgttgc atcttacatt actaaacacg ggaactgatc cgacgatgcg cctcatagag  10320
aggaatcttc ggattgcgat ggaggaagtc gtggtcattt cgaaactgat cagcaaaatc  10380
ttggaggctt gaagatggca attcgcaagc ccgcattgtc ggtcggcgaa gcacggcggc  10440
ttgctggtgc tcgacccgag atccaccatc ccaacccgac acttgttccc cagaagctgg  10500
acctccagca cttgcctgaa aaagccgacg agaaagacca gcaacgtgag cctctcgtcg  10560
ccgatcacat ttacagtccc gatcgacaac ttaagctaac tgtggatgcc cttagtccac  10620
ctccgtcccc gaaaaagctc caggtttttc tttcagcgcg accgcccgcg cctcaagtgt  10680
cgaaaacata tgacaacctc gttcggcaat acagtccctc gaagtcgcta caaatgattt  10740
taaggcgcgc gttggacgat ttcgaaagca tgctggcaga tggatcattt cgcgtggccc  10800
cgaaaagtta tccgatccct tcaactacag aaaaatccgt tctcgttcag acctcacgca  10860
tgttcccggt tgcgttgctc gaggtcgctc gaagtcattt tgatccgttg gggttggaga  10920
ccgctcgagc tttcggccac aagctggcta ccgccgcgct cgcgtcattc tttgctggag  10980
agaagccatc gagcaattgg tgaagaggga cctatcggaa cccctcacca aatattgagt  11040
gtaggtttga ggccgctggc cgcgtcctca gtcacctttt gagccagata attaagagcc  11100
aaatgcaatt ggctcaggct gccatcgtcc ccccgtgcga aacctgcacg tccgcgtcaa  11160
agaaataacc ggcacctctt gctgttttta tcagttgagg gcttgacgga tccgcctcaa  11220
gtttgcggcg cagccgcaaa atgagaacat ctatactcct gtcgtaaacc tcctcgtcgc  11280
gtactcgact ggcaatgaga agttgctcgc gcgatagaac gtcgcggggt ttctctaaaa  11340
acgcgaggag aagattgaac tcacctgccg taagtttcac ctcaccgcca gcttcggaca  11400
tcaagcgacg ttgcctgaga ttaagtgtcc agtcagtaaa acaaaaagac cgtcggtctt  11460
tggagcggac aacgttgggg cgcacgcgca aggcaacccg aatgcgtgca agaaactctc  11520
```

```
tcgtactaaa cggcttagcg ataaaatcac ttgctcctag ctcgagtgca acaactttat  11580
ccgtctcctc aaggcggtcg ccactgataa ttatgattgg aatatcagac tttgccgcca  11640
gatttcgaac gatctcaagc ccatcttcac gacctaaatt tagatcaaca accacgacat  11700
cgaccgtcgc ggaagagagt actctagtga actgggtgct gtcggctacc gcggtcactt  11760
tgaaggcgtg gatcgtaagg tattcgataa taagatgccg catagcgaca tcgtcatcga  11820
taagaagaac gtgtttcaac ggctcacctt tcaatctaaa atctgaaccc ttgttcacag  11880
cgcttgagaa attttcacgt gaaggatgta caatcatctc cagctaaatg ggcagttcgt  11940
cagaattgcg gctgaccgcg gatgacgaaa atgcgaacca agtatttcaa ttttatgaca  12000
aaagttctca atcgttgtta caagtgaaac gcttcgaggt tacagctact attgattaag  12060
gagatcgcct atggtctcgc cccggcgtcg tgcgtccgcc gcgagccaga tctcgcctac  12120
ttcataaacg tcctcatagg cacggaatgg aatgatgaca tcgatcgccg tagagagcat  12180
gtcaatcagt gtgcgatctt ccaagctagc accttgggcg ctacttttga caagggaaaa  12240
cagtttcttg aatccttgga ttggattcgc gccgtgtatt gttgaaatcg atcccggatg  12300
tcccgagacg acttcactca gataagccca tgctgcatcg tcgcgcatct cgccaagcaa  12360
tatccggtcc ggccgcatac gcagacttgc ttggagcaag tgctcggcgc tcacagcacc  12420
cagcccagca ccgttcttgg agtagagtag tctaacatga ttatcgtgtg gaatgacgag  12480
ttcgagcgta tcttctatgg tgattagcct ttcctggggg gggatggcgc tgatcaaggt  12540
cttgctcatt gttgtcttgc cgcttccggt agggccacat agcaacatcg tcagtcggct  12600
gacgacgcat gcgtgcagaa acgcttccaa atccccgttg tcaaaatgct gaaggatagc  12660
ttcatcatcc tgattttggc gtttccttcg tgtctgccac tggttccacc tcgaagcatc  12720
ataacgggag gagacttctt taagaccaga aacacgcgag cttggccgtc gaatggtcaa  12780
gctgacggtg cccgagggaa cggtcggcgg cagacagatt tgtagtcgtt caccaccagg  12840
aagttcagtg gcgcagaggg ggttacgtgg tccgacatcc tgctttctca gcgcgcccgc  12900
taaaatagcg atatcttcaa gatcatcata agagacgggc aaaggcatct tggtaaaaat  12960
gccggcttgg cgcacaaatg cctctccagg tcgattgatc gcaatttctt cagtcttcgg  13020
gtcatcgagc cattccaaaa tcggcttcag aagaaagcgt agttgcggat ccacttccat  13080
ttacaatgta tcctatctct aagcggaaat ttgaattcat taagagcggc ggttcctccc  13140
ccgcgtggcg ccgccagtca ggcggagctg gtaaacacca aagaaatcga ggtcccgtgc  13200
tacgaaaatg gaaacggtgt caccctgatt cttcttcagg gttggcggta tgttgatggt  13260
tgccttaagg gctgtctcag ttgtctgctc accgttattt tgaaagctgt tgaagctcat  13320
cccgccaccc gagctgccgg cgtaggtgct agctgcctgg aaggcgcctt gaacaacact  13380
caagagcata gctccgctaa aacgctgcca gaagtggctg tcgaccgagc ccggcaatcc  13440
tgagcgaccg agttcgtccg cgcttggcga tgttaacgag atcatcgcat ggtcaggtgt  13500
ctcggcgcga tcccacaaca caaaaacgcg cccatctccc tgttgcaagc cacgctgtat  13560
ttcgccaaca acggtggtgc cacgatcaag aagcacgata ttgttcgttg ttccacgaat  13620
atcctgaggc aagacacact ttacatagcc tgccaaattt gtgtcgattg cggtttgcaa  13680
gatgcacgga attattgtcc cttgcgttac cataaaatcg gggtgcggca agagcgtggc  13740
gctgctgggc tgcagctcgg tgggtttcat acgtatcgac aaatcgttct cgccggacac  13800
ttcgccattc ggcaaggagt tgtcgtcacg cttgccttct tgtcttcggc ccgtgtcgcc  13860
ctgaatggcg cgtttgctga ccccttgatc gccgctgcta tatgcaaaaa tcggtgtttc  13920
```

```
ttccggccgt ggctcatgcc gctccggttc gcccctcggc ggtagaggag cagcaggctg  13980
aacagcctct tgaaccgctg gaggatccgg cggcacctca atcggagctg gatgaaatgg  14040
cttggtgttt gttgcgatca aagttgacgg cgatgcgttc tcattcacct tcttttggcg  14100
cccacctagc caaatgaggc ttaatgataa cgcgagaacg acacctccga cgatcaattt  14160
ctgagacccc gaaagacgcc ggcgatgttt gtcggagacc agggatccag atgcatcaac  14220
ctcatgtgcc gcttgctgac tatcgttatt catcccttcg cccccttcag gacgcgtttc  14280
acatcgggcc tcaccgtgcc cgtttgcggc ctttggccaa cgggatcgta agcggtgttc  14340
cagatacata gtactgtgtg gccatccctc agacgccaac ctcgggaaac cgaagaaatc  14400
tcgacatcgc tccctttaac tgaatagttg gcaacagctt ccttgccatc aggattgatg  14460
gtgtagatgg agggtatgcg tacattgccc ggaaagtgga ataccgtcgt aaatccattg  14520
tcgaagactt cgagtggcaa cagcgaacga tcgccttggg cgacgtagtg ccaattactg  14580
tccgccgcac caagggctgt gacaggctga tccaataaat tctcagcttt ccgttgatat  14640
tgtgcttccg cgtgtagtct gtccacaaca gccttctgtt gtgcctccct tcgccgagcc  14700
gccgcatcgt cggcggggta ggcgaattgg acgctgtaat agagatcggg ctgctcttta  14760
tcgaggtggg acagagtctt ggaacttata ctgaaaacat aacggcgcat cccggagtcg  14820
cttgcggtta gcacgattac tggctgaggc gtgaggacct ggcttgcctt gaaaaataga  14880
taatttcccc gcggtagggc tgctagatct ttgctatttg aaacggcaac cgctgtcacc  14940
gtttcgttcg tggcgaatgt tacgaccaaa gtagctccaa ccgccgtcga gaggcgcacc  15000
acttgatcgg gattgtaagc caaataacgc atgcgcggat ctagcttgcc cgccattgga  15060
gtgtcttcag cctccgcacc agtcgcagcg gcaaataaac atgctaaaat gaaaagtgct  15120
tttctgatca tggttcgctg tggcctacgt ttgaaacggt atcttccgat gtctgatagg  15180
aggtgacaac cagacctgcc gggttggtta gtctcaatct gccgggcaag ctggtcacct  15240
tttcgtagcg aactgtcgcg gtccacgtac tcaccacagg cattttgccg tcaacgacga  15300
gggtcctttt atagcgaatt tgctgcgtgc ttggagttac atcatttgaa gcgatgtgct  15360
cgacctccac cctgccgcgt ttgccaagaa tgacttgagg cgaactggga ttgggatagt  15420
tgaagaattg ctggtaatcc tggcgcactg ttggggcact gaagttcgat accaggtcgt  15480
aggcgtactg agcggtgtcg gcatcataac tctcgcgcag gcgaacgtac tcccacaatg  15540
aggcgttaac gacggcctcc tcttgagttg caggcaatcg cgagacagac acctcgctgt  15600
caacggtgcc gtccggccgt atccatagat atacgggcac aagcctgctc aacggcacca  15660
ttgtggctat agcgaacgct tgagcaacat ttcccaaaat cgcgatagct gcgacagctg  15720
caatgagttt ggagagacgt cgcgccgatt tcgctcgcgc ggtttgaaag gcttctactt  15780
ccttatagtg ctcggcaagg ctttcgcgcg ccactagcat ggcatattca ggccccgtca  15840
tagcgtccac ccgaattgcc gagctgaaga tctgacggag taggctgcca tcgccccaca  15900
ttcagcggga agatcgggcc tttgcagctc gctaatgtgt cgtttgtctg gcagccgctc  15960
aaagcgacaa ctaggcacag caggcaatac ttcatagaat tctccattga ggcgaatttt  16020
tgcgcgacct agcctcgctc aacctgagcg aagcgacggt acaagctgct ggcagattgg  16080
gttgcgccgc tccagtaact gcctccaatg ttgccggcga tcgccggcaa agcgacaatg  16140
agcgcatccc ctgtcagaaa aaacatatcg agttcgtaaa gaccaatgat cttggccgcg  16200
gtcgtaccgg cgaaggtgat tacaccaagc ataagggtga gcgcagtcgc ttcggttagg  16260
```

```
atgacgatcg ttgccacgag gtttaagagg agaagcaaga gaccgtaggt gataagttgc  16320
ccgatccact tagctgcgat gtcccgcgtg cgatcaaaaa tatatccgac gaggatcaga  16380
ggcccgatcg cgagaagcac tttcgtgaga attccaacgg cgtcgtaaac tccgaaggca  16440
gaccagagcg tgccgtaaag gacccactgt gccccttgga aagcaaggat gtcctggtcg  16500
ttcatcggac cgatttcgga tgcgattttc tgaaaaacgg cctgggtcac ggcgaacatt  16560
gtatccaact gtgccggaac agtctgcaga ggcaagccgg ttacactaaa ctgctgaaca  16620
aagtttggga ccgtcttttc gaagatggaa accacatagt cttggtagtt agcctgccca  16680
acaattagag caacaacgat ggtgaccgtg atcacccgag tgataccgct acgggtatcg  16740
acttcgccgc gtatgactaa aataccctga acaataatcc aaagagtgac acaggcgatc  16800
aatggcgcac tcaccgcctc ctggatagtc tcaagcatcg agtccaagcc tgtcgtgaag  16860
gctacatcga agatcgtatg aatggccgta aacggcgccg gaatcgtgaa attcatcgat  16920
tggacctgaa cttgactggt ttgtcgcata atgttggata aaatgagctc gcattcggcg  16980
aggatgcggg cggatgaaca aatcgcccag ccttagggga gggcaccaaa gatgacagcg  17040
gtcttttgat gctccttgcg ttgagcggcc gcctcttccg cctcgtgaag gccggcctgc  17100
gcggtagtca tcgttaatag gcttgtcgcc tgtacatttt gaatcattgc gtcatggatc  17160
tgcttgagaa gcaaaccatt ggtcacggtt gcctgcatga tattgcgaga tcgggaaagc  17220
tgagcagacg tatcagcatt cgccgtcaag cgtttgtcca tcgtttccag attgtcagcc  17280
gcaatgccag cgctgtttgc ggaaccggtg atctgcgatc gcaacaggtc cgcttcagca  17340
tcactaccca cgactgcacg atctgtatcg ctggtgatcg cacgtgccgt ggtcgacatt  17400
ggcattcgcg gcgaaaacat ttcattgtct aggtccttcg tcgaaggata ctgatttttc  17460
tggttgagcg aagtcagtag tccagtaacg ccgtaggccg acgtcaacat cgtaaccatc  17520
gctatagtct gagtgagatt ctccgcagtc gcgagcgcag tcgcgagcgt ctcagcctcc  17580
gttgccgggt cgctaacaac aaactgcgcc cgcgcgggct gaatatatag aaagctgcag  17640
gtcaaaactg ttgcaataag ttgcgtcgtc ttcatcgttt cctaccttat caatcttctg  17700
cctcgtggtg acgggccatg aattcgctga gccagccaga tgagttgcct tcttgtgcct  17760
cgcgtagtcg agttgcaaag cgcaccgtgt tggcacgccc cgaaagcacg gcgacatatt  17820
cacgcatatc ccgcagatca aattcgcaga tgacgcttcc actttctcgt ttaagaagaa  17880
acttacggct gccgaccgtc atgtcttcac ggatcgcctg aaattccttt tcggtacatt  17940
tcagtccatc gacataagcc gatcgatctg cggttggtga tggatagaaa atcttcgtca  18000
tacattgcgc aaccaagctg gctcctagcg gcgattccag aacatgctct ggttgctgcg  18060
ttgccagtat tagcatcccg ttgtttttc gaacggtcag gaggaatttg tcgacgacag  18120
tcgaaaattt agggtttaac aaataggcgc gaaactcatc gcagctcatc acaaaacggc  18180
ggccgtcgat catggctcca atccgatgca ggagatatgc tgcagcggga gcgcatactt  18240
cctcgtattc gagaagatgc gtcatgtcga agccggtaat cgacggatct aactttactt  18300
cgtcaacttc gccgtcaaat gcccagccaa gcgcatggcc ccggcaccag cgttggagcc  18360
gcgctcctgc gccttcggcg ggcccatgca acaaaaattc acgtaacccc gcgattgaac  18420
gcatttgtgg atcaaacgag agctgacgat ggataccacg gaccagacgg cggttctctt  18480
ccggagaaat cccaccccga ccatcactct cgatgagagc cacgatccat tcgcgcagaa  18540
aatcgtgtga ggctgctgtg ttttctaggc cacgcaacgg cgccaacccg ctgggtgtgc  18600
ctctgtgaag tgccaaatat gttcctcctg tggcgcgaac cagcaattcg ccaccccggt  18660
```

```
ccttgtcaaa gaacacgacc gtacctgcac ggtcgaccat gctctgttcg agcatggcta  18720
gaacaaacat catgagcgtc gtcttacccc tcccgatagg cccgaatatt gccgtcatgc  18780
caacatcgtg ctcatgcggg atatagtcga aaggcgttcc gccattggta cgaaatcggg  18840
caatcgcgtt gccccagtgg cctgagctgg cgccctctgg aaagttttcg aaagagacaa  18900
accctgcgaa attgcgtgaa gtgattgcgc cagggcgtgt gcgccactta aaattccccg  18960
gcaattggga ccaataggcc gcttccatac caataccttc ttggacaacc acggcacctg  19020
catccgccat tcgtgtccga gcccgcgcgc ccctgtcccc aagactattg agatcgtctg  19080
catagacgca aaggctcaaa tgatgtgagc ccataacgaa ttcgttgctc gcaagtgcgt  19140
cctcagcctc ggataatttg ccgatttgag tcacggcttt atcgccggaa ctcagcatct  19200
ggctcgattt gaggctaagt ttcgcgtgcg cttgcgggcg agtcaggaac gaaaaactct  19260
gcgtgagaac aagtggaaaa tcgagggata gcagcgcgtt gagcatgccc ggccgtgttt  19320
ttgcagggta ttcgcgaaac gaatagatgg atccaacgta actgtctttt ggcgttctga  19380
tctcgagtcc tcgcttgccg caaatgactc tgtcggtata aatcgaagcg ccgagtgagc  19440
cgctgacgac cggaaccggt gtgaaccgac cagtcatgat caaccgtagc gcttcgccaa  19500
tttcggtgaa gagcacaccc tgcttctcgc ggatgccaag acgatgcagg ccatacgctt  19560
taagagagcc agcgacaaca tgccaaagat cttccatgtt cctgatctgg cccgtgagat  19620
cgttttccct ttttccgctt agcttggtga acctcctctt taccttccct aaagccgcct  19680
gtgggtagac aatcaacgta aggaagtgtt cattgcggag gagttggccg gagagcacgc  19740
gctgttcaaa agcttcgttc aggctagcgg cgaaaacact acggaagtgt cgcggcgccg  19800
atgatggcac gtcggcatga cgtacgaggt gagcatatat tgacacatga tcatcagcga  19860
tattgcgcaa cagcgtgttg aacgcacgac aacgcgcatt gcgcatttca gtttcctcaa  19920
gctcgaatgc aacgccatca attctcgcaa tggtcatgat cgatccgtct tcaagaagga  19980
cgatatggtc gctgaggtgg ccaatataag ggagatagat ctcaccggat ctttcggtcg  20040
ttccactcgc gccgagcatc acaccattcc tctccctcgt gggggaaccc taattggatt  20100
tgggctaaca gtagcgcccc cccaaactgc actatcaatg cttcttcccg cggtccgcaa  20160
aaatagcagg acgacgctcg ccgcattgta gtctcgctcc acgatgagcc gggctgcaaa  20220
ccataacggc acgagaacga cttcgtagag cgggttctga acgataacga tgacaaagcc  20280
ggcgaacatc atgaataacc ctgccaatgt cagtggcacc ccaagaaaca atgcgggccg  20340
tgtggctgcg aggtaaaggg tcgattcttc caaacgatca gccatcaact accgccagtg  20400
agcgtttggc cgaggaagct cgccccaaac atgataacaa tgccgccgac gacgccggca  20460
accagcccaa gcgaagcccg cccgaacatc caggagatcc cgatagcgac aatgccgaga  20520
acagcgagtg actggccgaa cggaccaagg ataaacgtgc atatattgtt aaccattgtg  20580
gcggggtcag tgccgccacc cgcagattgc gctgcggcgg gtccggatga ggaaatgctc  20640
catgcaattg caccgcacaa gcttggggcg cagctcgata tcacgcgcat catcgcattc  20700
gagagcgaga ggcgatttag atgtaaacgg tatctctcaa agcatcgcat caatgcgcac  20760
ctccttagta taagtcgaat aagacttgat tgtcgtctgc ggatttgccg ttgtcctggt  20820
gtggcggtgg cggagcgatt aaaccgccag cgccatcctc ctgcgagcgg cgctgatatg  20880
acccccaaac atcccacgtc tcttcggatt ttagcgcctc gtgatcgtct tttggaggct  20940
cgattaacgc gggcaccagc gattgagcag ctgtttcaac ttttcgcacg tagccgtttg  21000
```

```
caaaaccgcc gatgaaatta ccggtgttgt aagcggagat cgcccgacga agcgcaaatt  21060
gcttctcgtc aatcgtttcg ccgcctgcat aacgactttt cagcatgttt gcagcggcag  21120
ataatgatgt gcacgcctgg agcgcaccgt caggtgtcag accgagcata gaaaaatttc  21180
gagagtttat ttgcatgagg ccaacatcca gcgaatgccg tgcatcgaga cggtgcctga  21240
cgacttgggt tgcttggctg tgatcttgcc agtgaagcgt ttcgccggtc gtgttgtcat  21300
gaatcgctaa aggatcaaag cgactctcca ccttagctat cgccgcaagc gtagatgtcg  21360
caactgatgg ggcacacttg cgagcaacat ggtcaaactc agcagatgag agtggcgtgg  21420
caaggctcga cgaacagaag gagaccatca aggcaagaga aagcgacccc gatctcttaa  21480
gcatacctta tctccttagc tcgcaactaa caccgcctct cccgttggaa gaagtgcgtt  21540
gttttatgtt gaagattatc gggagggtcg gttactcgaa aattttcaat tgcttcttta  21600
tgatttcaat tgaagcgaga aacctcgccc ggcgtcttgg aacgcaacat ggaccgagaa  21660
ccgcgcatcc atgactaagc aaccggatcg acctattcag gccgcagttg gtcaggtcag  21720
gctcagaacg aaaatgctcg gcgaggttac gctgtctgta aacccattcg atgaacggga  21780
agcttccttc cgattgctct tggcaggaat attggcccat gcctgcttgc gctttgcaaa  21840
tgctcttatc gcgttggtat catatgcctt gtccgccagc agaaacgcac tctaagcgat  21900
tatttgtaaa aatgtttcgg tcatgcggcg gtcatgggct tgacccgctg tcagcgcaag  21960
acggatcggt caaccgtcgg catcgacaac agcgtgaatc ttggtggtca aaccgccacg  22020
ggaacgtccc atacagccat cgtcttgatc ccgctgtttc ccgtcgccgc atgttggtgg  22080
acgcggacac aggaactgtc aatcatgacg acattctatc gaaagccttg gaaatcacac  22140
tcagaatatg atcccagacg tctgcctcac gccatcgtac aaagcgattg tagcaggttg  22200
tacaggaacc gtatcgatca ggaacgtctg cccagggcgg gcccgtccgg aagcgccaca  22260
agatgacatt gatcacccgc gtcaacgcgc ggcacgcgac gcggcttatt tgggaacaaa  22320
ggactgaaca acagtccatt cgaaatcggt gacatcaaag cggggacggg ttatcagtgg  22380
cctccaagtc aagcctcaat gaatcaaaat cagaccgatt tgcaaacctg atttatgagt  22440
gtgcggccta aatgatgaaa tcgtccttct agatcgcctc cgtggtgtag caacacctcg  22500
cagtatcgcc gtgctgacct tggccaggga attgactggc aagggtgctt tcacatgacc  22560
gctcttttgg ccgcgataga tgatttcgtt gctgctttgg gcacgtagaa ggagagaagt  22620
catatcggag aaattcctcc tggcgcgaga gcctgctcta tcgcgacggc atcccactgt  22680
cgggaacaga ccggatcatt cacgaggcga aagtcgtcaa cacatgcgtt ataggcatct  22740
tcccttgaag gatgatcttg ttgctgccaa tctggaggtg cggcagccgc aggcagatgc  22800
gatctcagcg caacttgcgg caaaacatct cactcacctg aaaaccacta gcgagtctcg  22860
cgatcagacg aaggcctttt acttaacgac acaatatccg atgtctgcat cacaggcgtc  22920
gctatcccag tcaatactaa agcggtgcag gaactaaaga ttactgatga cttaggcgtg  22980
ccacgaggcc tgagacgacg cgcgtagaca gttttttgaa atcattatca aagtgatggc  23040
ctccgctgaa gcctatcacc tctgcgccgg tctgtcggag agatgggcaa gcattattac  23100
ggtcttcgcg cccgtacatg cattggacga ttgcagggtc aatggatctg agatcatcca  23160
gaggattgcc gcccttacct tccgtttcga gttggagcca gcccctaaat gagacgacat  23220
agtcgacttg atgtgacaat gccaagagag agatttgctt aacccgattt ttttgctcaa  23280
gcgtaagcct attgaagctt gccggcatga cgtccgcgcc gaaagaatat cctacaagta  23340
aaacattctg cacaccgaaa tgcttggtgt agacatcgat tatgtgacca agatccttag  23400
```

```
cagtttcgct tggggaccgc tccgaccaga aataccgaag tgaactgacg ccaatgacag  23460
gaatcccttc cgtctgcaga taggtaccgg atcccgcagg atcgtcgcaa atgatttcag  23520
cctgttcgaa aacgatcccc tcatgcagca tggggcgcac cccatcggcc atgatcggcg  23580
gtgtggccac ggctacagga tcacgcgaga cgattgtgag attgcgaatg gcgatattgc  23640
ggattggggc ctccgctaaa ccgagaaaga cgccggcggc atgtgccaga tggcggattt  23700
ccacatcttc gacagtaatt ccgtcgataa acggggtccc gtcgtcgaca ggtgcagggt  23760
ctcgcgactg cacccagccg tcatgcccat cggcatcgca atggtaatgg gcattggcgg  23820
aaagcgcggt atgcacgcca tccagcaaca cgcggcgcat ggtgatatcg ctgactgaac  23880
cgccacggcc ccgccgcgtc ttgagacgca agccgcgatc cgtgccaacc atgtcgcagt  23940
cctctacggt tacgtcatgc acgccacccg acatttccga gccgatcacc agcccgccat  24000
ggccgcgctc catcaggcaa tggcgcacgc tgacgccgcg tgtttccgcc agatggtcgt  24060
cctcgccgtt cggcccgcgt ttgcctgcct tcacagcaat gcaatcgtcg cccactgaaa  24120
agcgcacgcc tgatatcgtc acgttgcggc agctttccgg gttgaaacca tcggtattgg  24180
ggctgttatg cggagcgctg attgtgagac ccgccgctgt cagggtctcg caccettgtg  24240
gatggaccgt ccaggacggt gcattgcgaa tggtgaaacc gaaaagcccg acattgcggc  24300
aggagacgag atgcaggccg cgcggtcggc gcgcgccgtc acgggtttct ttcggccagc  24360
tccaccagtc gcctctgtcg ccggaaccat cgaggacgcc tgtgccttcg atcacgagat  24420
tatctgcgcc gatggcatgg accggcgcag cgaaacaggc atccggtagc ccttcccaac  24480
tgccgagcat gcggcccgtc tcatcgcggg caggcaggat cggccagcca ttgcgggtgg  24540
agggtgcgcg cagcacggcc ccttccgcaa gatgaaacgt catgtcgctt ttcaaccgca  24600
cgggaaacgc tgtccagagg ccggcagcaa atcgcaacgt gccgcccgca ggcacggcgg  24660
caactgcctc ttccagagcg cgggcgttgg cgcgtgcgcc ggcttcgtcg tcaagcgcaa  24720
tatccggcgt cagcgaaaat gccgtcgcct cgacaagccc cgcgcagggc gctgtcctga  24780
actccaggct tgcgaaccca tccgcttcga acagataccg tgtatccgga cgcagatcat  24840
gcagcagcgt caccacggtg gcggtttttc cggctcgtaa atcaccatct tgcgaagtca  24900
gccgccatgc cgtctgcggc aggcgatatc gcgcaccggg tacagcgagg caaagcgccg  24960
ccgttcgcgc cgaaagcgcg atgatagagg gttcgttcat gctcgtttct cgttgttcgt  25020
gcatgtcccg cgaaaacaat cggcgggaat gcccatgtca cccggcaacc ggataaagag  25080
cccgccgccg caagcgcggc gggccattgt cgtcaatcga atttggccag aacgtcattg  25140
gtcgtatcga tgatctgccg cctcttccgc cgtcagctgg ccataggcat attcctccag  25200
cgtatcgatg aagccggagc ggatttccgg atgttcgttg aagggcgaaa ctaccggtcc  25260
agatgccgcc atgacgatgg cgttggcggc gcgcacttcc ggctcaccct tgtcgcccag  25320
acgctgcgcc gcagccttgg aagcaggcag gccgcgagac gtgccaagcg catcgatgcc  25380
ctcaggctcg ttcagcaggc agttcaggat ttgcgctgcc gcttcagggt tcttcgagtt  25440
tttcgagata gaaaagacca tggaaggctt gcgataaacg ccttccgtta cggcatcggc  25500
aagcttcagc atcggcacgg gtttcagcac ctgcccatcc ttcaggggat cggcatattt  25560
cgaataggtg gaatcccatt cataggaacc agcgatacgg ccttcggacc acgacggctt  25620
ttcataaaga ttgacgttgc catcggccgc ttcctctttc tgggagcgaa tggagccggt  25680
ttccaccagc ttgccgacga acgagatacc ttccgccagt tcctccggcg tccaggcgac  25740
```

```
acggttggtc ttggggtcga ccagatcgtt tccggttttc tgcaccacgg cgagtgtcac  25800

gagaagctgg gcagtctcct ttacggcatt gaaggtgtaa tgatccttgc cgagcttttc  25860

cttgatggtt tttgttgccg cgaagaattc atcccatgtc ttggggattt caacgccagc  25920

cttctcgaag gtggtggcgt tgaaaaaaaa cacgcggccg gtggtggaga ctgaaaggcc  25980

ctgaagcacc ccgttcatag aacccgcttc cagatccgtc tcggcccatt gcgaaagatc  26040

gagaggtttc agctgacgca gatcagcaaa accttcacca ttcttggaaa acagcggcat  26100

ccatggccag ttcacctgaa cgatatcagc ctccgtcttg cctgccattt gcgtggtcag  26160

tttttccaga tatccatcga agccggtaaa ttcacctttg accgtgtggc tgtatttttc  26220

accgcaggcg gcaatcgcct tctgagtggc gacatgacgg ctttcgccgc cccaccacga  26280

catacgcagt tccgcggcac ccgccgcagg cgcagccacc gtggccagat aggcagcgcc  26340

ggccagcatc gccattgttc tcgtcatcgt cgtcatcttc attgttcttc tcctcctcga  26400

aaaatcaggc acgctcgtcc cctcctcaca gcgagacatt gcggccatcg gccttgtcga  26460

aaatatgcag cttctcgggg tccggcttca gtcgcagaat gccgtcgcgc ccaagcgcct  26520

cgaattcggc tgctcccacc acgctcacga gcttctgtcc gcccagatcg gcatgcagat  26580

agacctcgtg ccccatgaat tcggcgttgg tcagtttagc aagggcgaat tcgacccagc  26640

tttc                                                               26644
```

<210> SEQ ID NO 26
<211> LENGTH: 27
<212> TYPE: DNA
<213> ORGANISM: Artificial Sequence
<220> FEATURE:
<223> OTHER INFORMATION: Primer H3-2 Down

<400> SEQUENCE: 26

```
atcttacctt ccttttcgtt ttccaac                                         27
```

<210> SEQ ID NO 27
<211> LENGTH: 25
<212> TYPE: DNA
<213> ORGANISM: Artificial
<220> FEATURE:
<223> OTHER INFORMATION: Primer Set2 5'

<400> SEQUENCE: 27

```
ctgcttggat gcccgaggca tagac                                           25
```

<210> SEQ ID NO 28
<211> LENGTH: 24
<212> TYPE: DNA
<213> ORGANISM: Artificial Sequence
<220> FEATURE:
<223> OTHER INFORMATION: Primer Vir Screen 1 5'

<400> SEQUENCE: 28

```
catccaagca gcaagcgcgt tacg                                            24
```

<210> SEQ ID NO 29
<211> LENGTH: 25
<212> TYPE: DNA
<213> ORGANISM: Artificial Sequence
<220> FEATURE:
<223> OTHER INFORMATION: Primer Vir Screen 4 3'

<400> SEQUENCE: 29

```
gtctatgcct cgggcatcca agcag                                           25
```

<210> SEQ ID NO 30
<211> LENGTH: 24
<212> TYPE: DNA
<213> ORGANISM: Artificial Sequence
<220> FEATURE:
<223> OTHER INFORMATION: Primer Vir Screen 5 5'

<400> SEQUENCE: 30
gagaccgtag gtgataagtt gccc 24

<210> SEQ ID NO 31
<211> LENGTH: 24
<212> TYPE: DNA
<213> ORGANISM: Artificial Sequence
<220> FEATURE:
<223> OTHER INFORMATION: Primer Vir Screen 8 3'

<400> SEQUENCE: 31
tctcatttag gggctggctc caac 24

<210> SEQ ID NO 32
<211> LENGTH: 24
<212> TYPE: DNA
<213> ORGANISM: Artificial Sequence
<220> FEATURE:
<223> OTHER INFORMATION: Primer VirG

<400> SEQUENCE: 32
tgcgagcaac atggtcaaac tcag 24

<210> SEQ ID NO 33
<211> LENGTH: 24
<212> TYPE: DNA
<213> ORGANISM: Artificial Sequence
<220> FEATURE:
<223> OTHER INFORMATION: Primer VirB 1 3'

<400> SEQUENCE: 33
gacatgcaga acaacgagaa acga 24

<210> SEQ ID NO 34
<211> LENGTH: 24
<212> TYPE: DNA
<213> ORGANISM: Artificial Sequence
<220> FEATURE:
<223> OTHER INFORMATION: Primer PSB1-1 5'

<400> SEQUENCE: 34
gcacaccgaa atgcttggtg taga 24

<210> SEQ ID NO 35
<211> LENGTH: 25
<212> TYPE: DNA
<213> ORGANISM: Artificial Sequence
<220> FEATURE:
<223> OTHER INFORMATION: Primer nilA For1

<400> SEQUENCE: 35
ggccgtgcac ggcatcaatc tcgaa 25

METHOD OF INCREASING PLANT TRANSFORMATION FREQUENCY USING MODIFIED STRAINS OF *AGROBACTERIA*

CROSS-REFERENCE TO RELATED APPLICATIONS

This application is a national phase entry under 35 U.S.C. §371 of International Patent Application PCT/US2011/046028, filed Jul. 29, 2011, designating the United States of America and published in English as International Patent Publication WO 2012/016222 on Jun. 21, 2012, which claims the benefit under Article 8 of the Patent Cooperation Treaty and under 35 U.S.C. §119(e) to U.S. Provisional Patent Application Ser. No. 61/368,965, filed Jul. 29, 2010, the disclosure of each of which is hereby incorporated herein by this reference in its entirety.

TECHNICAL FIELD

The present invention relates to *Agrobacterium* strains that harbor transformation-enhancing genes on a plasmid capable of replication independently of the *Agrobacterium* chromosome, the Ti plasmid, and plant transformation binary vectors, and uses for these *Agrobacterium* strains.

STATEMENT ACCORDING TO 37 C.F.R. §1.821(c) OR (e)-SEQUENCE LISTING SUBMITTED AS ASCII TEXT FILE

Pursuant to 37 C.F.R. §1.821(c) or (e), a file containing an ASCII text version of the Sequence Listing has been submitted concomitant with this application, the contents of which are hereby incorporated by reference.

BACKGROUND

Plant transformation generally encompasses the methodologies required and utilized for the introduction of a plant-expressible foreign gene into plant cells, such that fertile progeny plants may be obtained which stably maintain and express the foreign gene. Numerous members of the monocotyledonous and dicotyledonous classifications have been transformed. Transgenic agronomic crops, as well as fruits and vegetables, are of commercial interest. Such crops include but are not limited to maize, rice, soybeans, canola, sunflower, alfalfa, sorghum, wheat, cotton, peanuts, tomatoes, potatoes, and the like. Despite the development of plant transformation systems for introducing plant-expressible foreign genes into plant cells, additional improvements which allow for increased transformation efficiency are desirable and provide significant advantages in overcoming operational disadvantages when transforming plants with foreign genes.

Several techniques are known for introducing foreign genetic material into plant cells, and for obtaining plants that stably maintain and express the introduced gene. Such techniques include acceleration of genetic material coated onto microparticles directly into cells (e.g., U.S. Pat. Nos. 4,945,050 and 5,141,131). Other transformation technology includes silicon carbide or WHISKERS™ technology. See, e.g., U.S. Pat. Nos. 5,302,523 and 5,464,765. Electroporation technology has also been used to transform plants. See, e.g., WO 87/06614, U.S. Pat. Nos. 5,472,869, 5,384,253, WO 92/09696, and WO 93/21335. Additionally, fusion of plant protoplasts with liposomes containing the DNA to be delivered, direct injection of the DNA, as well as other possible methods, may be employed.

Once the inserted DNA has been integrated into the plant genome, it is usually relatively stable throughout subsequent generations. The transformed cells grow inside the plants in the usual manner. They can form germ cells and transmit the transformed trait(s) to progeny plants. Such plants can be grown in the normal manner and may be crossed with plants that have the same transformed hereditary factors or other hereditary factors. The resulting hybrid individuals have the corresponding phenotypic properties, for example, the ability to control the feeding of plant pest insects.

A number of alternative techniques can also be used for inserting DNA into a host plant cell. Those techniques include, but are not limited to, transformation with T-DNA delivered by *Agrobacterium tumefaciens* or *Agrobacterium rhizogenes* as the transformation agent. Plants may be transformed using *Agrobacterium* technology, as described, for example, in U.S. Pat. Nos. 5,177,010, 5,104,310, European Patent Application No. 0131624B1, European Patent Application No. 120516, European Patent Application No. 159418B1, European Patent Application No. 176112, U.S. Pat. Nos. 5,149,645, 5,469,976, 5,464,763, 4,940,838, 4,693,976, European Patent Application No. 116718, European Patent Application No. 290799, European Patent Application No. 320500, European Patent Application No. 604662, European Patent Application No. 627752, European Patent Application No. 0267159, European Patent Application No. 0292435, U.S. Pat. Nos. 5,231,019, 5,463,174, 4,762,785, 5,004,863, and 5,159,135. The use of T-DNA-containing vectors for the transformation of plant cells has been intensively researched and sufficiently described in European Patent Application 120516; An et al. (1985, *Embo J.* 4:277-284), Fraley et al. (1986, *Crit. Rev. Plant Sci.* 4:1-46), and Lee and Gelvin (2008, *Plant Physiol.* 146: 325-332), and is well established in the field.

The biology of T-DNA transfer from *Agrobacterium* to plant cells is known. See, e.g., Gelvin (2003) *Microbiol. Molec. Biol. Rev.* 67:16-37; and Gelvin (2009) *Plant Physiol.* 150:1665-1676. At minimum, at least a T-DNA right border repeat, but often both the right border repeat and the left border repeat of the Ti or Ri plasmid will be joined as the flanking region of the genes desired to be inserted into the plant cell. The left and right T-DNA border repeats are crucial cis-acting sequences required for T-DNA transfer. Various trans-acting components are encoded within the total *Agrobacterium* genome. Primary amongst these are the proteins encoded by the vir genes, which are normally found as a series of operons on the Ti or Ri plasmids. Various Ti and Ri plasmids differ somewhat in the complement of vir genes, with, for example, virF not always being present. Proteins encoded by vir genes perform many different functions, including recognition and signaling of plant cell/bacteria interaction, induction of vir gene transcription, formation of a Type IV secretion channel, recognition of T-DNA border repeats, formation of T-strands, transfer of T-strands to the plant cell, import of the T-strands into the plant cell nucleus, and integration of T-strands into the plant nuclear chromosome, to name but a few. See, e.g., Tzfira and Citovsky (2006) *Curr. Opin. Biotechnol.* 17:147-154.

If *Agrobacterium* strains are used for transfoimation, the DNA to be inserted into the plant cell can be cloned into special plasmids, for example, either into an intermediate (shuttle) vector or into a binary vector. Intermediate vectors are not capable of independent replication in *Agrobacterium* cells, but can be manipulated and replicated in common *Escherichia coli* molecular cloning strains. Such intermediate vectors comprise sequences are commonly framed by the right and left T-DNA border repeat regions, that may include a selectable marker gene functional for the selection of transformed plant cells, a cloning linker, a cloning polylinker, or other sequence which can function as an introduction site for genes destined for plant cell transformation. Cloning and manipulation of genes desired to be transferred to plants can thus be easily performed by standard methodologies in *E. coli*, using the shuttle vector as a cloning vector. The finally manipulated shuttle vector can subsequently be introduced into *Agrobacterium* plant transformation strains for further work. The intermediate shuttle vector can be transferred into *Agrobacterium* by means of a helper plasmid (via bacterial conjugation), by electroporation, by chemically mediated direct DNA transformation, or by other known methodologies. Shuttle vectors can be integrated into the Ti or Ri plasmid or derivatives thereof by homologous recombination owing to sequences that are homologous between the Ti or Ri plasmid, or derivatives thereof, and the intermediate plasmid. This homologous recombination (i.e., plasmid integration) event thereby provides a means of stably maintaining the altered shuttle vector in *Agrobacterium*, with an origin of replication and other plasmid maintenance functions provided by the Ti or Ri plasmid portion of the co-integrant plasmid. The Ti or Ri plasmid also comprises the vir regions comprising vir genes necessary for the transfer of the T-DNA. The plasmid carrying the vir region is commonly a mutated Ti or Ri plasmid (helper plasmid) from which the T-DNA region, including the right and left T-DNA border repeats, have been deleted. Such pTi-derived plasmids, having functional vir genes and lacking all or substantially all of the T-region and associated elements are descriptively referred to herein as helper plasmids.

The superbinary system is a specialized example of the shuttle vector/homologous recombination system (reviewed by Komari et al. (2006) in *Methods in Molecular Biology* (K. Wang, ed.) No. 343: *Agrobacterium Protocols* ($2^{nd}$ Edition, Vol. 1) HUMANA PRESS Inc., Totowa, N.J., pp. 15-41; and Komori et al. (2007) *Plant Physiol.* 145:1155-1160). The *Agrobacterium tumefaciens* host strain employed with the superbinary system is LBA4404(pSB1). Strain LBA4404 (pSB1) harbors two independently replicating plasmids, pAL4404 and pSB1. pAL4404 is a Ti-plasmid-derived helper plasmid which contains an intact set of vir genes (from Ti plasmid pTiACH5), but which has no T-DNA region (and thus no T-DNA left and right border repeat sequences). Plasmid pSB1 supplies an additional partial set of vir genes derived from pTiBo542; this partial vir gene set includes the virB operon and the virC operon, as well as genes virG and virD1. One example of a shuttle vector used in the superbinary system is pSB11, which contains a cloning polylinker that serves as an introduction site for genes destined for plant cell transformation, flanked by right and left T-DNA border repeat regions. Shuttle vector pSB11 is not capable of independent replication in *Agrobacterium*, but is stably maintained as a co-integrant plasmid when integrated into pSB1 by means of homologous recombination between common sequences present on pSB1 and pSB11. Thus, the fully modified T-DNA region introduced into LBA4404(pSB1) on a modified pSB11 vector is productively acted upon and transferred into plant cells by Vir proteins derived from two different *Agrobacterium* Ti plasmid sources (pTiACH5 and pTiBo542). The superbinary system has proven to be particularly useful in transformation of monocot plant species. See Hiei et al. (1994) *Plant J.* (6:271-282); and Ishida et al. (1996) *Nat. Biotechnol.* 14:745-750.

In addition to the vir genes harbored by *Agrobacterium* Ti plasmids, other, chromosomally borne virulence controlling genes (termed chv genes) are known to control certain aspects of the interactions of *Agrobacterium* cells and plant cells, and thus affect the overall plant transformation frequency (Pan et al. (1995) *Molec. Microbiol.* 17:259-269). Several of the chromosomally borne genes required for virulence and attachment are grouped together in a chromosomal locus spanning 29 kilobases (Matthysse et al. (2000) *Biochim. Biophys. Acta* 1490:208-212).

Regardless of the particular plasmid system employed, the *Agrobacterium* cells so transformed are used for the transformation of plant cells. Plant explants (for example, pieces of leaf, segments of stalk, roots, but also protoplasts or suspension-cultivated cells) can advantageously be cultivated with *Agrobacterium tumefaciens* or *Agrobacterium rhizogenes* for the transfer of the DNA into the plant cell. Whole plants may then be regenerated from the infected plant material following placement in suitable growth conditions and culture medium, which may contain antibiotics or herbicides for selection of the transformed plant cells. The plants so obtained can then be tested for the presence of the inserted DNA.

These techniques for introducing foreign genetic material into plants can be used to introduce beneficial traits into the plants. For example, billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through the introduction of Bt insecticidal protein genes has revolutionized modern agriculture and heightened the importance and value of insecticidal proteins and their genes.

Several Bt proteins have been used to create the insect-resistant transgenic plants that have been successfully developed and in many cases registered and commercialized. These include Cry1Ab, Cry1Ca, Cry1Fa, and Cry3Bb in corn, Cry1Ac and Cry2Ab in cotton, and Cry3A in potato.

The commercial products expressing Bt proteins express a single protein except in cases where the combined insecticidal spectrum of two proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm).

That is, some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. 1998, *Nature Biotechnol.* 16:144-146).

If Bt proteins are selected for use in combination, they need to exert their insecticidal effect independently so that resistance developed to one protein does not confer resistance to the second protein (i.e., there is not cross resistance to the proteins). A robust assessment of cross-resistance is typically made using populations of a pest species normally sensitive to the insecticidal protein that has been selected for resistance to the insecticidal proteins. If, for example, a pest population selected for resistance to "Protein A" is sensitive to "Protein B," we would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (U.S. Pat. No. 6,855,873). The key predictor of lack of cross resistance integral to this approach is that the insecticidal proteins do not compete for receptors in a sensitive insect species.

In the event that two Bt Cry toxins compete for the same receptor, then if that receptor mutates in that insect so that one of the toxins no longer binds to that receptor and thus is no longer insecticidal against the insect, it might also be the case that the insect will also be resistant to the second toxin (which competitively bound to the same receptor). However, if two toxins bind to two different receptors, this could be an indication that the insect would not be simultaneously resistant to those two toxins.

Cry1Fa is useful in controlling many lepidopteran pests species including the European corn borer (ECB; *Ostrinia nubilalis* (Hübner)) and the fall armyworm (FAW; *Spodoptera frugiperda*), and is active against the sugarcane borer (SCB; *Diatraea* saccharalis).

The Cry1Fa protein, as produced in corn plants containing event TC1507, is responsible for an industry-leading insect resistance trait for FAW control. Cry1Fa is further deployed in the HERCULEX®, SMARTSTAX™, and WIDESTRIKE™ products.

The ability to conduct (competitive or homologous) receptor binding studies using Cry1Fa protein is limited because the most common technique available for labeling proteins for detection in receptor binding assays inactivates the insecticidal activity of the Cry1Fa protein.

Cry1Ab and Cry1Fa are insecticidal proteins currently used (separately) in transgenic corn to protect plants from a variety of insect pests. A key pest of corn that these proteins provide protection from is the European corn borer (ECB). U.S. Patent Application No. 2008/0311096 relates in part to the use of Cry1Ab to control a Cry1F-resistant ECB population.

This application describes strains of *Agrobacterium tumefaciens* that have been modified to increase plant transformation frequency. The use of these strains provides novel plant transformation systems for the introduction of plant-expressible foreign genes into plant cells. In addition, these strains provide additional improvements which allow for increased transformation efficiency and provide significant advantages in overcoming operational disadvantage when transforming plants with foreign genes.

SUMMARY OF THE INVENTION

*Agrobacterium* strains that harbor transformation-enhancing genes on a plasmid capable of replication independently of the *Agrobacterium* chromosome, the Ti plasmid, and plant transformation binary vectors and methods for their use are described herein. The *Agrobacterium* strains are deficient in DNA recombination functions that result in instability or rearrangement of plant transformation binary vectors, and harbor transformation-enhancing genes on a plasmid capable of replication independently of the *Agrobacterium* chromosome, the Ti plasmid, and plant transformation binary vectors. Additional *Agrobacterium* strains that harbor transformation-enhancing genes integrated into the *Agrobacterium* chromosome at a locus that does not interfere with or otherwise compromise the normal growth and plant transformation ability of the *Agrobacterium* cells and their use are also described.

In one embodiment of the methods described herein, a plant is transformed by contacting a cell of the plant with an *Agrobacterium* strain having at least one pTi helper plasmid comprising a 14.8 KpnI fragment of pSB1 and a pTi plasmid having at least one disarmed T-DNA region, the T-DNA region comprising at least a right T-DNA border and exogenous DNA adjacent to the border, wherein the plasmids have differing origins of replication relative to each other.

In a further embodiment of the methods described herein, a plant is transformed by contacting a cell of the plant with a bacterium of the genus *Agrobacterium* having a 14.8 KpnI VirBCDG fragment of pSB1 and a pTi plasmid having at least one disarmed T-DNA region, wherein the 14.8 KpnI VirBCDG fragment has been integrated into a neutral integration site of a chromosome of the bacterium.

In an additional embodiment of the methods described herein, an *Agrobacterium* strain includes at least one pTi helper plasmid comprising a 14.8 KpnI fragment of pSB1 and a pTi plasmid having at least one disarmed T-DNA region, wherein the plasmids have differing origins of replication relative to each other.

In a further embodiment, an *Agrobacterium* strain with transformation-enhancing properties includes a 14.8 KpnI VirBCDG fragment isolated from pSB1 and a pTi plasmid having at least one disarmed T-DNA region.

In another embodiment, a nilA genomic locus of *Agrobacterium tumefaciens* includes a polynucleotide sequence that is integrated into the nilA genomic locus.

In an additional embodiment, an *Agrobacterium* strain with a 14.8 KpnI VirBCDG fragment of SB1 is integrated into a neutral integration site on the *Agrobacterium* chromosome.

In another embodiment an *Agrobacterium* strain LB4404 includes a 14.8 KpnI VirBCDG fragment of pSB1 on a pTi helper plasmid and a pTi plasmid having at least one disarmed T-DNA region and has exogenous DNA adjacent to at least one *Agrobacterium* T-DNA border, wherein the plasmids have differing origins of replication relative to each other.

In a further embodiment an *Agrobacterium* strain LBA4404 includes at least one vir gene from a 14.8 KpnI VirBCDG fragment isolated from pSB1 integrated into a neutral integration site on the *Agrobacterium* chromosome.

In additional embodiments plants are provided that are made according to the transformation methods described herein.

In yet another embodiment, a fertile transgenic corn plant, or progeny thereof, expresses insecticidal amounts of Cry1Ca protein, Cry1F insecticidal protein, Cry1Ab1 insecticidal protein, and herbicide-tolerant amounts of AAD-1 protein, wherein the Cry1Ca, Cry1F, Cry1Ab1, and AAD1 proteins are collectively expressed from a single locus of recombinant DNA stably incorporated in the genome of the plant.

DESCRIPTION OF THE DRAWINGS

FIG. 1 shows a cloning scheme for the construction of plasmid pDAB9292. The double-stranded oligonucleotide fragment of Step 1 is shown at the bottom of FIG. 1, with top strand (SEQ ID NO:2) and bottom strand (SFQ ID NO:3).

FIG. 4A shows a map of binary vector plasmid pDAB101513.

FIG. 4B shows a map of binary vector plasmid pDAB101514.

DETAILED DESCRIPTION OF THE INVENTION

Figure 2:
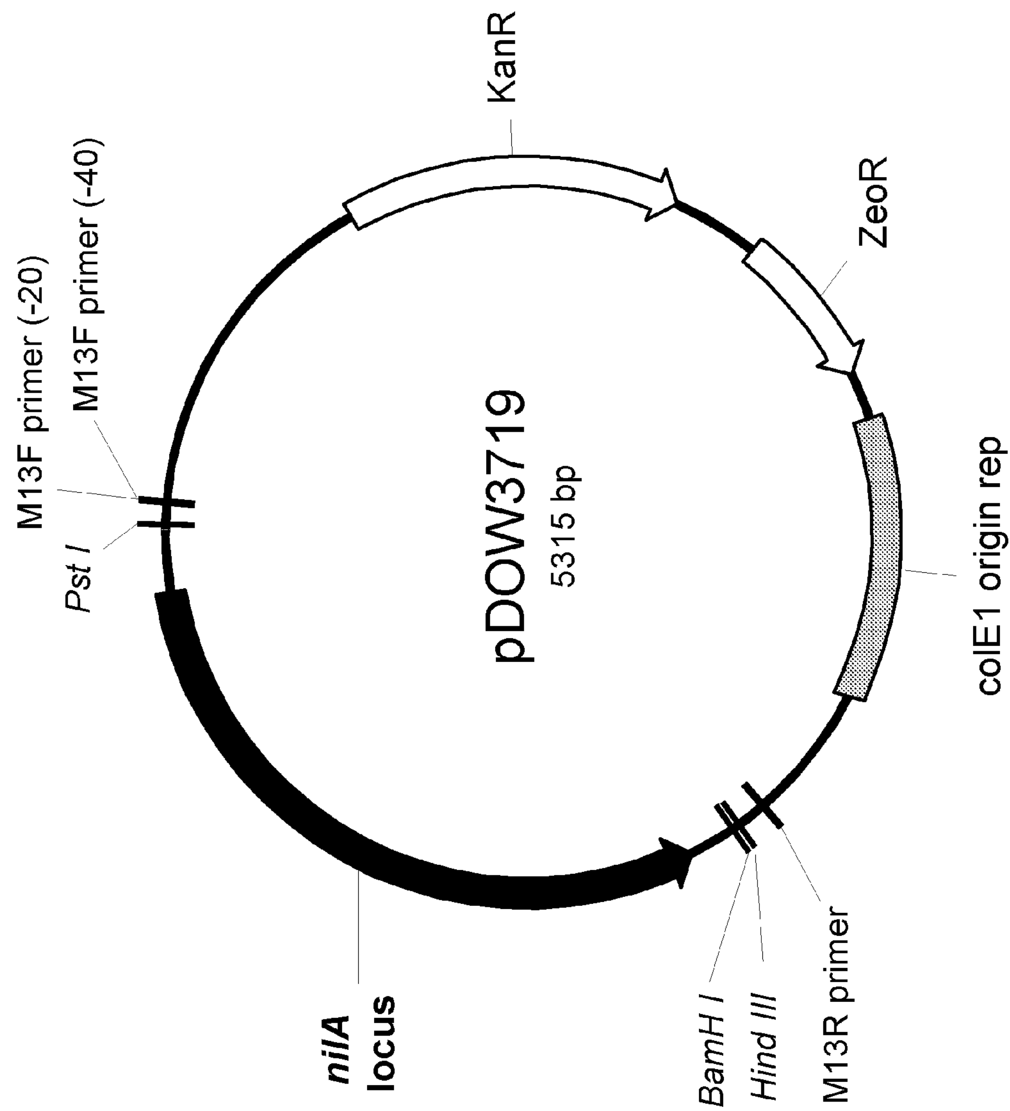
FIG. 2 shows a map of plasmid pDOW3719.

Strains of *Agrobacterium* differ from one another in their ability to transform plant cells. Wild-type, oncogenic *Agrobacterium* strains are known for their ability to induce crown galls (tumorous overgrowths) on many host plants, especially dicot species. This transformation of normally growing plant cells into non-self regulated tumor cells comes about as the result of the transfer of specialized DNA sequences (T-DNA), which encodes plant expressible genes encoding plant hormones, from the tumor-inducing (Ti) plasmid into the plant cells, wherein they are stably integrated into plant chromosomes. The Ti plasmid from strain Bo542 (i.e., pTiBo542) is notable in that, when placed in some *Agrobacterium* chromosomal backgrounds, it promotes the induction of especially large, vigorously growing tumors on some plants (Hood et al. (1986) *J. Bacteriol.* 168:1291-1301). The genes responsible for this "supervirulence" phenotype reside on pTiBo542 outside the T-DNA regions. Further work found that a plasmid containing a "15.8" kilobase pair (kbp) KpnI fragment derived from pTiBo542 and which contained the entire virG, virB, and virC operons promoted increased tumor formation by strain A281, when compared to strains lacking the plasmid (Jin et al. (1987) *J. Bacteriol.* 169:4417-4425). The virG gene of pTiBo542 is believed to be responsible for the supervirulent phenotype of *Agrobacterium* strain A281. virG from pTiBo542 causes a 1.7-fold increase in virB expression compared with virG from pTiA6, due to differences between the two genes in the promoter regions, coding sequences, and 3' untranslated regions (Chen et al. (1991) *Molec. Gen. Genet.* 230:302-309). Thus, the virG gene from pTiBo542 can be advantageously used to promote higher T-DNA transfer efficiencies, and thus higher plant transformation frequencies, especially when present on a large KpnI fragment of the pTiBo542 plasmid that also harbors the pTiBo542 virB and virC operons.

The complete, annotated sequence of pTiBo542 was submitted to GENBANK as Accession Number DQ058764 on May 12, 2005. Examination of the KpnI restriction fragment map and gene annotations reveals that the entire virB operon (which includes the genes virB1, virB2, virB3, virB4, virB5, virB6, virB7, virB8, virB9, virB10, and virB11), the virG gene, the virC operon (which comprises genes virC1 and virC2) and the part of the virD operon comprising gene virD1 are isolatable on a KpnI fragment comprising 14,815 base pairs (bp). Assumedly, the size of the "15.8 kbp" KpnI fragment referred to in Jin et al. (supra.) was estimated from agarose gel mobility of the fragment, and that the true size of the referenced fragment is, in fact, 14.8 kbp. One skilled in the field of molecular biology will understand that size estimation of such large DNA fragments by means of agarose gel electrophoresis mobility can differ from the true fragment size determined by DNA sequence analysis by 1 kbp or more. For ease of description, this fragment derived from pTiBo542 will be referred to herein as the 14.8 KpnI VirBCDG fragment.

An embodiment of methods described herein includes uses of the transformation-enhancing properties encoded on the 14.8 KpnI VirBCDG fragment isolated from pSB1 in *Agrobacterium* strains harboring at least one disarmed pTi helper plasmid, wherein the 14.8 KpnI VirBCDG fragment is borne on a plasmid having a replication origin of an incompatibility group other than IncP to transform a plant. A further embodiment includes the *Agrobacterium* strain as described for use in the method. A T-DNA region to be introduced to a plant using this *Agrobacterium* strain can be borne on a plasmid having a T-DNA region adjacent to at least one *Agrobacterium* T-DNA border, the plasmid having a replication origin of an IncP incompatibility group or an incompatability group that is compatible with the incompatibility group of the 14.8 KpnI VirBCDG fragment that is borne on a plasmid having a replication origin of an incompatibility group other than IncP. The T-DNA region of this plasmid can be adjacent right and left *Agrobacterium* T-DNA borders.

Plasmids are assigned to incompatibility groups (genotypic designation: inc; group designation: Inc) based on sequences contained in the plasmid. The inc determinant typically serves to prevent other plasmids of the same or related incompatibility group from coexisting in the same host, and helps maintain a certain copy number of the plasmid within the cell. See, e.g., Fernandez-Lopez, et al. (2006) *FEMS Microbiol. Rev.* 30:942-66; and Adamczyk and Jagura-Burdzy (2003) *Acta Biochim. Pol.* 50:425-53. Two plasmids are incompatible if either is less stable in the presence of the other than it was by itself. Competition for cell resources can result when two plasmids of the same incompatibility group are found in the same cell. Whichever plasmid is able to replicate faster, or provides some other advantage, will be represented to a disproportionate degree among the copies allowed by the incompatibility system. Surprisingly, plasmids can also be incompatible when they both possess the same functions for partitioning themselves into daughter cells.

Plasmids typically fall into only one of the many existing incompatibility groups. There are more than 30 known incompatibility groups. Plasmids belonging to incompatibility group IncP have been studied thoroughly and a large number of plasmids which derive from this IncP group have been constructed (Schmidhauser et al. (1988) *Biotechnology* 10:287-332). Exemplary plasmids containing the IncP incompatibility group include: pMP90RK, pRK2013, pRK290, pRK404, and pRK415. These plasmids may be maintained in numerous bacterial species including *E. coli* and *Agrobacterium tumefaciens*. Examples of other incompatibility groups include, but are not limited to; IncN, IncW, IncL/M, IncT, IncU, IncW, IncY, IncB/O, IncFII, IncII, IncK, IncCom9, IncFI, IncFII, IncFIII, IncHI1, IncHI2, IncX, IncA/C, IncD, IncFIV, IncFV/FO, IncFVI, IncH1 3, IncHII, Inc12, IncI, IncJ, IncV, IncQ, and the like, including variants thereof, e.g., exhibiting substantial sequence or functional relationship. Table 1 lists several commonly known incompatibility groups and provides examples of plasmids which represent these incompatibility groups (this listing of incompatability groups and plasmids is provided by way of example only and is not intended to be limiting on the incompatibility groups and plasmids useful with the *Agrobacterium* strains and methods described herein).

Another embodiment of the methods described herein includes uses of transformation-enhancing properties encoded on the 14.8 KpnI VirBCDG fragment isolated from pSB1 in *Agrobacterium* strains having a deficiency in RecA function, and harboring at least one disarmed pTi helper plasmid, wherein the 14.8 KpnI VirBCDG fragment is borne on a plasmid having a replication origin of an incompatibility group other than IncP. A further embodiment includes the *Agrobacterium* strain as described for use in the method. A T-DNA region to be introduced to a plant using this *Agrobacterium* strain can be borne on a plasmid having a T-DNA region adjacent to at least one *Agrobacterium* T-DNA border, the plasmid having a replication origin of an IncP incompatibility group or an incompatability group that is compatible with the incompatibility group of the 14.8 KpnI VirBCDG fragment that is borne on a plasmid having a replication origin of an incompatibility group other than IncP.

Yet another embodiment of the methods described herein includes uses of the transformation-enhancing properties encoded on the 14.8 KpnI VirBCDG fragment isolated from pSB1, and harboring at least one disarmed pTi helper plasmid, wherein the 14.8 KpnI VirBCDG fragment is integrated into a chromosomally located neutral integration site of an *Agrobacterium* strain different from strain C58. A further embodiment includes the *Agrobacterium* strain as described for use in the method. A T-DNA region to be introduced to a plant using this *Agrobacterium* strain further comprises a plasmid having a T-DNA region adjacent to at least one *Agrobacterium* T-DNA border.

Although superbinary systems are known, for example, see WO 94/00977A1, WO 95/06722A1, and WO 95/16031A1, and are further described by Komari et al. (supra), and Komori et al. (supra), these systems possess a number of disadvantages. An operational disadvantage of the superbinary system, which is overcome by the *Agrobacterium* strains and methods described herein, is the necessity for formation of a co-integrant plasmid between pSB1 and pSB11 (and its derivatives) as the means by which the altered T-DNA borne on pSB11 derivatives is to be stably maintained in *Agrobacterium*. This co-integration event generates a pair of large (ca. 2.3 kbp) directly repeated sequences due to recombination between the homologous regions of pSB1 and pSB11. As is well known to those skilled in the field of molecular biology, large repeated sequences such as these are preferred targets for intramolecular recombination that leads eventually to DNA deletions and other rearrangements, particularly when the repeats are a part of plasmid structure. In the *Agrobacterium* superbinary system, such rearrangements may lead to partial rearrangement or complete loss of the T-DNA region introduced by pSB11 derivatives, ultimately resulting in little or no transfer of intact desired foreign genes into the host plant cells.

A further disadvantage to the above-described superbinary system, and which is also overcome by the *Agrobacterium* strains and methods described herein, is that the formation of the co-integrant plasmid between pSB1 and pSB11 derivatives generates a large plasmid (minimally, greater than 43 kbp) having two distinct ColE1-type (incompatibility group pMB1/ColE1) origins of replication (ori), as well as a third on derived from the RK2 plasmid (incompatibility group IncP). Although in normal circumstances the ColE1 ori is nonfunctional in *Agrobacterium*, genomic mutations are known which allow the stable maintenance of plasmids having a ColE1 on in *Agrobacterium* (Ruslyakova et al. (1999) *Russian J. Genet.* 35:327-331). In cells having such mutations, a plasmid such as the pSB1::pSB11 derivative co-integrant having three functional origins of replication would be expected to be highly unstable. Thus, the superbinary system has imperfections that are advantageously addressed by elements of the *Agrobacterium* strains and methods for transforming plants described herein.

The DNA structure of the foreign gene or genes destined for introduction and expression in transgenic plant cells by *Agrobacterium*-mediated transformation can have a profound influence on the stability of the binary vector plasmid or shuttle vector plasmid harboring those genes in cells of *Escherichia coli* and *Agrobacterium*. Instability is particularly manifested when the foreign genes comprise gene components that are employed multiple times within the gene constructs. For example, it is not uncommon that a particular plant-expressible promoter may be used to drive the expression of different protein coding regions in a transgenic plant. Other gene components such as 3' untranslated regions (3'UTR) (i.e., transcription termination and polyadenylation addition determining sequences) and even highly similar protein coding regions may be duplicated or present in multiple copies within a single T-DNA region. As mentioned above, these repeated sequence elements, which may exist in either inverted or directly repeated orientations, are targets for intramolecular recombinations that may lead to DNA deletions and other rearrangements, particularly as the repeats are a part of plasmid structure.

Multiple specialized strains of *E. coli* have been developed to serve as molecular cloning hosts that help to overcome such instability difficulties (e.g., STBL2™, STBL3™, and STBL4™ strains offered by INVITROGEN; Carlsbad, Calif.). A feature common to all such *E. coli* cloning strains is the presence of a genomic mutation in a recA gene. The RecA protein is a multifunctional enzyme that plays a role in homologous recombination, DNA repair, and induction of the bacterial SOS response. In the homologous recombination process, the protein functions as a DNA-dependent ATPase, promoting synapsis, heteroduplex formation and strand exchange between homologous DNAs. Thus, cells deficient in RecA function are more prone to tolerate homologous DNA sequences without rearrangement or deletion.

RecA-deficient strains of *Agrobacterium* have been developed to help address the instability problems observed when cloning large DNA fragments containing repeated sequences (Klapwicj et al. (1979) *Molec. Gen. Genet.* 173:171-175; Farrand et al. (1989) *J. Bacteria* 171:5314-5321; Lazo et al. (1991) *Bio/Technology* 9:963-967). These strains have proven useful in helping stabilize high molecular weight transfoiming constructs in some cases (Frary and Hamilton (2001), *Transgenic Res.* 10:121-132), but not in all instances (Song et al. (2003) *Theor. Appl. Genet.* 107:958-964). Thus, *Agrobacterium* chromosomal backgrounds that are recA defective in developing strains that are highly efficient in plasmid maintenance and plant transformation capability can be advantageously used. In addition to using *Agrobacterium* chromosomal backgrounds that are recA defective in developing strains for use in the methods described herein, the recA functionality can be deactivated in an existing or produced strain to make that strain useful in the methods described herein. See, e.g., Farrand et al. (supra). For example, a strain can be developed with RecA functionality and any chromosomal additions desired, e.g., the addition of vir genes, can be made then the RecA functionality disabled.

BIBAC vectors designed to enable efficient transformation of large DNA fragments into plant and non-plant host cells can be used. See, e.g., U.S. Pat. Nos. 5,733,744, 5,977,439, and U.S. Patent Application No. 2002/0123100A1. One *Agrobacterium* strain that can be utilized with the BIBAC vectors is the RecA-deficient strain UIA143 developed by Farrand et al. (supra). Refinements to the BIBAC system have used subsets of the genes harbored on the 14.8 KpnI VirBCDG fragment in combination with other vir genes to enhance the plant transformation capability of engineered *Agrobacterium* strains. In particular, the virG gene from the 14.8 KpnI VirBCDG fragment has been employed alone or in combination with the virE1 and virE2 genes from pTiA6 in the UIA143 RecA-deficient strain. See, e.g., Hamilton et al. (1996) *Proc. Natl. Acad. Sci.* 93:9975-9979; Hamilton (1997), *Gene* 200:107-116; Frary and Hamilton (supra).

In addition, a suitable vector used to transform plant cell using the methods described herein can contain a selectable marker gene encoding a protein that confers on the transformed plant cells resistance to an antibiotic or a herbicide. The individually employed selectable marker gene may accordingly permit the selection of transformed cells while the growth of cells that do not contain the inserted DNA can be suppressed by the selective compound. The particular selectable marker gene(s) used may depend on experimental design or preference, but any of the following selectable markers may be used, as well as any other gene not listed herein that could function as a selectable marker. Examples of selectable markers include, but are not limited to, genes that provide resistance or tolerance to antibiotics such as Kanamycin, G418, Hygromycin, Bleomycin, and Methotrexate, or to herbicides, such as Phosphinothricin (Bialaphos), Glyphosate, Imidazolinones, Sulfonylureas, Triazolopyrimidines, Chlorosulfuron, Bromoxynil, and DALAPON.

In addition to a selectable marker, a reporter gene may also be used. In some instances a reporter gene could be used without a selectable marker. Reporter genes are genes that typically do not provide a growth advantage to the recipient organism or tissue. Reporter genes typically encode for a protein that provides for a phenotypic change or enzymatic property. Suitable reporter genes include, but are not limited to, those that encode glucuronidase (GUS), firefly luciferase, or fluorescent proteins such as green fluorescent protein and yellow fluorescent protein.

In addition to numerous technologies for transforming plants, the type of tissue that is contacted with the foreign genes may vary as well. Such tissue may include, but is not limited to, embryogenic tissue, callus tissue types I and II, hypocotyl, and meristem. Almost all plant tissues may be transformed during dedifferentiation using appropriate techniques within the skill of the art. One skilled in the field of plant transformation will understand that multiple methodologies are available for the production of transformed plants, and that they may be modified and specialized to accommodate biological differences between various host plant species.

Regardless of the particular transformation technique employed, the foreign gene can be incorporated into a gene transfer vector adapted to express the foreign gene in a plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), a promoter from sugarcane bacilliform virus, and the like may be used. Plant-derived promoters include, but are not limited to, ribulose-1,6-bisphosphate (RUBP) carboxylase small subunit (ssu) promoter, beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include, but are not limited to, alcohol dehydrogenase 1 (ADH1) intron 1 and ADH1-intron 6. Constitutive promoters may be used. Constitutive promoters direct continuous gene expression in nearly all cells types and at nearly all times (e.g., actin promoter, ubiquitin promoter, CaMV 35S promoter). Tissue specific promoters are responsible for gene expression in specific cell or tissue types, such as the leaves or seeds. Examples of other promoters that may be used include those that are active during a certain stage of the plant's development, as well as active in specific plant tissues and organs. Examples of such promoters include, but are not limited to, promoters that are root specific, pollen-specific, embryo specific, corn silk specific, cotton fiber specific, seed endosperm specific, and phloem specific.

Under certain circumstances, the use of an inducible promoter may be desirable. An inducible promoter is responsible for expression of genes in response to a specific signal, such as physical stimulus (e.g., heat shock gene promoters); light (e.g., Ribulose-bis-phosphate 1,5 carboxylase promoter); hormone (e.g., glucocorticoid); antibiotic (e.g., Tetracycline); metabolites; and stress (e.g., drought). Other desirable transcription and translation elements that function in plants also may be used, such as, for example, 5' untranslated leader sequences, RNA transcription termination sequences and poly-adenylate addition signal sequences. Any suitable plant-specific gene transfer vector known to the art may be used.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by multiple seed companies. These include combinations of IR traits conferred by Bt (*Bacillus thuringiensis*) insecticidal proteins and HT traits such as tolerance to Acetolactate Synthase (ALS) inhibitors such as Sulfonylureas, Imidazolinones, Triazolopyrimidine, Sulfonanilides, and the like, Glutamine Synthetase (GS) inhibitors such as Bialaphos, Glufosinate, and the like, 4-HydroxyPhenylPyruvate Dioxygenase (HPPD) inhibitors such as Mesotrione, Isoxaflutole, and the like, 5-EnolPyruvylShikimate-3-Phosphate Synthase (EPSPS) inhibitors such as Glyphosate and the like, and Acetyl-Coenzyme A Carboxylase (ACCase) inhibitors such as Haloxyfop, Quizalofop, Diclofop, and the like. Other examples are known in which transgenically provided proteins provide plant tolerance to herbicide chemical classes such as phenoxy acids herbicides and pyridyloxyacetates auxin herbicides (see WO 2007/053482A2), or phenoxy acids herbicides and aryloxyphenoxypropionates herbicides (see WO 2005107437A2,A3). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a Bt insecticidal protein with one or more additional HT traits such as those mentioned above, plus one or more additional input traits (e.g., other insect resistance conferred by Bt-derived or other insecticidal proteins, insect resistance conferred by mechanisms such as RNAi and the like, disease resistance, stress tolerance, improved nitrogen utilization, and the like), or output traits (e.g., high oils content, healthy oil composition, nutritional improvement, and the like). Such combinations may be obtained either through conventional breeding (e.g., breeding stack) or jointly as a novel transformation event involving the simultaneous introduction of multiple genes (e.g., molecular stack). Benefits include the ability to manage insect pests and improved weed control in a crop plant that provides secondary benefits to the producer and/or the consumer. Thus, the *Agrobacterium* strains and methods described herein can be used to provide transformed plants with combinations of traits that comprise a complete agronomic package of improved crop quality with the ability to flexibly and cost effectively control any number of agronomic issues.

The virG genes of various pTi plasmids have been studied to understand their ability to enhance plant transformation frequency. Liu et al. (1992, *Plant Molec. Biol.* 20:1071-1087) found that extra copies of virG genes from multiple sources (i.e., from different pTi plasmids, but including pTiBo542) enhanced the transient transformation of some plants, and the magnitude of the effect depended on the identity of the helper pTi plasmid with which the particular virG gene was paired. A mutant of a virG gene (presumably from pTiA6), named virGN54D (the mutation replaces amino acid Asn54 with Asp), is constitutively expressed in *Agrobacterium* (induction of wild-type virG genes requires an acidic pH, a high monosaccharide concentration, and the presence of phenolic inducers, such as acetosyringone). See Pazour et al. (1992) *J. Bacteriol.* 174:4169-4174. VirGN54D of pTiA6 was effective in enhancing maize transformation, whereas multiple copies of the parent wild-type virG were ineffective. See Hansen et al. (1994) *J. Bacteriol.* 174:4169-4174. A "ternary" (i.e., three-plasmid) system wherein a copy of the constitutive mutant virGN54D gene from pTi15955 was co-resident on a pBBR1-derived plasmid in *Agrobacterium tumefaciens* strain LBA4404 that contained the disarmed pTi helper plasmid pAL4404 and a binary vector harboring genes for plant transformation has been described. See van der Fits et al. (2000) *Plant Molec. Biol.* 43:495-502. The constitutively expressed virGN54D gene was found to dramatically increase both transient and stable transformation efficiencies of several plant species. Plasmids containing the pBRRI replication control region cannot be classed as belonging to any known incompatibility group and, thus, may co-exist with a broad range of other plasmids in a single host. Further, the abilities of various combinations of vir genes to affect plant transformation efficiencies in tobacco, cotton and rice have been tested, specifically: the mutant virGN54D gene derived from pTiA6, the virG gene from pTiBo542, the VirEl/E2 genes from pTiA6, and a combination of the latter two gene sets. See Park et al. (2000) *Theor. Appl. Genet.* 101:1015-1020. Increases in transformation efficiencies were observed with some plant species and additional copies of vir genes.

European Patent Application No. 2042602A1 and U.S. Patent Application No. 2010/0132068A1 describe cosmid binary vectors and "booster" plasmids that, when present in an *Agrobacterium* cell harboring a pTi helper plasmid, constitute further examples of ternary plasmid systems. Booster plasmids as disclosed therein possess a replication origin of the IncW incompatibility group, and comprise plasmid pVGW, having the virGN54D gene, and plasmid pVGW2, which is a derivative of pVGW having modifications to facilitate cloning and selection.

The functions encoded by chromosomal genes in *Agrobacterium* have classically been determined by two genetic approaches. The first, or forward genetics method, entails obtaining a molecular clone of the gene to be studied, followed by placement of the cloned gene in a genetic environment wherein a "gain of function" phenotype can be assessed. A second, or "reverse genetics method," requires disruption of the genes' structure by insertion or deletion of sequences in or around the gene in the chromosome, followed by determination of which proteins or phenotypes have been removed by the loss of gene function. This is the approach used to construct the previously described RecA-deficient mutant of strain C58. See Farrand et al., supra. Those skilled in the field of genetic manipulation of *Agrobacterium* cells will understand that diverse vectors and numerous methods have been described to enable such gene disruption experiments. The method has proven to be particularly useful when used to identify genes that are not involved in vitality, growth, and plant transformation capability of the mutated strain. One such genetic locus in *Agrobacterium* strain C58 is the pgl/picA locus. See, Lee et al. (2001) *Plant Microbe Interact.* 14:577-579; and Lee (2006) in *Methods in Molecular Biology* (K. Wang, ed.) No. 343: *Agrobacterium Protocols* (2nd Edition, Vol. 1) HUMANA PRESS Inc., Totowa, N.J. pp. 55-66. Cells in which a virD2 gene has been integrated into this chromosomal locus by homologous recombination were found to have a plant transformation phenotype identical to that resulting from *A. tumefaciens* strains harboring the virD2 gene located on a replicating plasmid. See Lee et al., supra. Further, a T-DNA region integrated into the pgl/picA locus of C58 may be functionally delivered to the plant cell (Oltmanns et al. (2010) *Plant Physiol.* 152:1158-1166). Thus, in strain C58, the pgl/picA locus can serve as a "neutral integration site" for introduction of genes into the C58 chromosome. As used herein, "neutral integration site" refers to a gene or chromosomal locus, natively present on the chromosome of an *Agrobacterium* cell, whose normal function is not required for the growth of the cell or for the capability of the cell to perform all the functions required for plant transformation. When disrupted by the integration of a DNA sequence not normally present within that gene, the cell harboring a disrupted neutral integration site gene can productively perform plant transformation. By way of example, Hoekema et al. (1984, *EMBO J.* 3:2485-2490) demonstrated that a functional T-region integrated into an uncharacterized locus in the C58 chromosome by means of Tn3 transposition was productively transferred to plant cells.

The *Agrobacterium* strains discussed herein can be used advantageously to introduce one or more genes into a plant, e.g., to provide individual or multiple insecticidal or herbicidal properties to the plant. For example, the *Agrobacterium* strains can be used to introduce one or more, two or more, three or more, four or more, five or more, or six or more genes into a plant. Using the *Agrobacterium* strains described herein, the polynucleotide containing the selectable gene sequences is inserted into a single location in the plant cell when the plant cell is transformed. In terms of the size of the T-DNA regions used to insert the genes, the T-DNA regions can be equal to or greater than 15,000 nucleotide base pairs, greater than or equal to 20,000 nucleotide base pairs, equal to or greater than 25,000 nucleotide base pairs, equal to or greater than 26,000 nucleotide base pairs, equal to or greater than 27,000 nucleotide base pairs, equal to or greater than 28,000 nucleotide base pairs, equal to or greater than 29,000 nucleotide base pairs, or equal to or greater than 30,000 nucleotide base pairs. When using the *Agrobacterium* strains described herein, the selectable gene sequences can have equal to or greater than 60%, equal to or greater than 65%, equal to or greater than 67%, equal to or greater than 69.5%, equal to or greater than 70%, equal to or greater than 75%, or equal to or greater than 80% sequence homology and retain their transcribable sequence identities. The types of genes that can be introduced can encode insecticidal proteins, herbicidal proteins, or a mixture of insecticidal proteins and herbicidal proteins. Specific examples of genes that can be introduced include the genes encoding the Cry1Ca insecticidal protein, Cry1F insecticidal protein, Cry1Ab1 insecticidal protein, and AAD1 herbicidal protein, which can be introduced in various combinations or as a set including all four. Monocotyledonous (monocot) and dicotyledonous (dicot) species can be transformed using these *Agrobacterium* strains.

Also disclosed herein is the nilA genomic locus of *Agrobacterium tumefaciens*, into which a polynucleotide sequence can be integrated. Such an integrated polynucleotide sequence can include any vir gene or vir operon or other useful genes. Examples 17-20 show the identification, characterization, and use of the nilA genomic locus of *Agrobacterium tumefaciens* as well as the production of an *Agrobacterium tumefaciens* strain with multiple vir genes located on the chromosome. The nilA genomic locus, or any locus which shares 85-100% nucleotide sequence identity, could be identified in other *Agrobacterium* strains using the techniques for identification and characterization described herein, and any such identified nilA loci could be used in a manner similar to that described herein to integrate vir or other suitable genes which can, e.g., increase the efficiency of plant transformation. The techniques for identification and characterization of such a genomic locus described herein could also be used to identify other neutral integration sites on the *Agrobacterium* chromosome at which polynucleotide sequences containing vir or other genes can be integrated such that the *Agrobacterium* strain remains capable of transforming plants. Some chromosomal sites are already known that could be used as neutral integration sites, for example, the RecA site in a RecA-deficient strain, and the pgl/picA locus in *Agrobacterium tumefaciens* strain C58. However, there is a need to identify new neutral sites in *Agrobacterium tumefaciens* strains besides C58, as the pgl/picA locus is not detected in some other strains, for example, strain LBA4404 (Oltmanns et al., supra). Additional chromosomal sites which can be used as neutral integration sites are described in U.S. Pat. No. 6,323,396. Thus, an *Agrobacterium* strain with a vir gene integrated into a neutral integration site on the *Agrobacterium* chromosome is also disclosed. Such an *Agrobacterium* strain could use a nilA genomic locus or other neutral integration site for the integration of vir genes.

Multiple types of useful genes could be added to the chromosome in this way making the use of T-helper plasmids unnecessary. For example, additional vir genes and multiple copies of useful vir genes from different strains could be used.

Also disclosed herein is an *Agrobacterium* strain containing vir genes on a helper plasmid having a replication origin of an incompatibility group other than IncP and a plasmid having a T-DNA region adjacent to at least one *Agrobacterium* T-DNA border, the plasmid having a replication origin of an IncP incompatibility group.

Further disclosed are plants made by the methods described herein using the *Agrobacterium* strains described herein. Such plants stably integrate any T-DNA regions introduced using the methods described herein. Further, such plants express any genes and exhibit any genetic traits conferred by those T-DNA regions. Additionally, any progeny of the plants made by the methods described herein using the *Agrobacterium* strains described herein stably produce any genes and exhibit any genetic traits conferred by those T-DNA regions found in the parent.

In a specific embodiment, a plant is described that stably expresses Cry1Ca insecticidal proteins, Cry1F insecticidal proteins, Cry1Ab1 insecticidal proteins, and AAD1 herbicidal proteins. This plant, for example, can be maize.

While certain example *Agrobacterium* strains are described herein, the functionality discussed could be moved to other *Agrobacterium* strains with the same criteria, e.g., other strains which are deficient in RecA or could be made deficient in RecA. Examples of other strains that could be used with the strains and methods described herein include, but are not limited to, *Agrobacterium tumefaciens* strain C58, *Agrobacterium tumefaciens* strain Chry5, *Agrobacterium rhizogenes* strains, *Agrobacterium tumefaciens* strain EHA101, *Agrobacterium tumefaciens* strain EHA105, *Agrobacterium tumefaciens* strain MOG101, and *Agrobacterium tumefaciens* strain T37.

All patents, patent applications, provisional applications, and publications referred to or cited herein are incorporated by reference in their entirety to the extent they are not inconsistent with the explicit teachings of this specification.

Following are examples that illustrate procedures for utilizing the *Agrobacterium* strains and practicing the methods described herein. These examples should not be construed as limiting. All percentages are by weight and all solvent mixture proportions are by volume unless otherwise noted. All temperatures are in degrees Celsius.

Unless specifically indicated or implied, the terms “a,” “an,” and “the” signify “at least one” as used herein.

EXAMPLE 1

Construction of a Deletion Variant of Plasmid pUCD2

Construction of plasmid pUCD2 was described by Close et al. (1984, *Plasmid* 12:111-118), and the complete 13,239 bp DNA sequence is disclosed for the first time herein as SEQ ID NO:1. pUCD2 harbors four genes conferring bacterial resistance to antibiotics: specifically, resistance to Spectinomycin, Kanamycin, Tetracycline, and Ampicillin (FIG. 1). Standard molecular biology methods, as taught, for example, in Sambrook et al. (1989, *Molecular Cloning: A Laboratory Manual* (2nd Edition., COLD SPRING HARBOR LABORATORY PRESS, Plainview, N.Y.) and Ausubel et al. (1995, *Current Protocols in Molecular Biology* (GREENE PUBLISHING AND WILEY-INTERSCIENCE, New York), and updates thereof, were employed in this and other steps described in this example and in other examples of this disclosure. A first modification to pUCD2 was made by cleaving pUCD2 DNA with restriction enzymes Sac I and Sac II and ligation to a mostly double-stranded oligonucleotide fragment having appropriate overhanging “sticky ends” compatible with Sac I- or Sac II generated overhangs. This double-stranded oligonucleotide (FIG. 1) was created by annealing two complementary oligonucleotide sequences, disclosed as SEQ ID NO:2 and SEQ ID NO:3. The sequences of the oligonucleotides of SEQ ID NO:2 and SEQ ID NO:3 are designed to restore a functional Kanamycin resistance gene upon ligation with pUCD2 DNA cleaved with Sac I and Sac II. This manipulation created plasmid pDAB9290 (FIG. 1), which differs from pUCD2 by the deletion of the coding region for Spectinomycin resistance, elimination of a Kpn I restriction enzyme recognition site from within the coding region for Kanamycin resistance, and creation of a new Kpn I site downstream of the Kanamycin resistance coding region.

DNA of plasmid pDAB9290 was further manipulated to render inoperative the genes encoding Tetracycline resistance and Ampicillin resistance by first cleaving with restriction enzymes Pst I and Sal I, treating the overhanging ends left by these enzymes with the QUICK BLUNTING™ kit (NEW ENGLAND BIOLABS; Ipswich, Mass.) to create blunt ends, and self ligation to circularize the fragments thus produced. The resulting plasmid (pDAB9291) retains only the Kanamycin bacterial antibiotic resistance gene, and has a unique site for cleavage by Kpn I downstream of the Kanamycin resistance gene. The sequence of pDAB9291 is disclosed as SEQ ID NO:4. Plasmid pDAB9291 has two origins of replication, one (colE1 incompatibility group) derived from plasmid pBR322, and a second derived from plasmid pSa (incompatibility group W). Thus, plasmid pDAB9291 is capable of medium-copy-number maintenance in *E. coli* and *Agrobacterium.*

EXAMPLE 2

Cloning of a 14.8 Kpn I virBCDG Fragment into pDAB9291

A 14.8-kbp Kpn I fragment containing the virG, virB, and virC operons and virD1 from the "supervirulent" pTiBo542 (FIG. 1) was isolated from plasmid pSB1 (Komari et al., supra; and Komori et al., supra), and cloned into the unique Kpn I site of pDAB9291. Plasmids containing each of the two possible orientations of the insert fragment were obtained, and were named pDAB9292 and pDAB9293. One plasmid, pDAB9292 (FIG. 1) was selected for further work. The DNA sequence of pDAB9292 is disclosed as SEQ ID NO:5.

EXAMPLE 3

Construction of a RecA-Deficient *Agrobacterium* Strain Harboring the Helper Plasmid pTiEHA105

*Agrobacterium* strain UIA143 is a RecA-deficient strain having the C58 genetic background and was constructed and described by Farrand et al. (supra). The chromosomal recA gene was deleted and replaced with a gene cassette conferring resistance to Erythromycin at 150 μg/mL. The UIA143 strain contains no Ti plasmid or Ti plasmid derivative.

*Agrobacterium* strain EHA105, constructed and described by Hood et al. (1993, *Transgenic Research* 2:208-221), harbors a helper plasmid (herein called pTiEHA105) derived from the "supervirulent" pTiBo542 plasmid. Plasmid pTiEHA105 DNA was prepared from strain EHA105 and introduced by electroporation into cells of strain UIA143 made electrocompetent by standard methods (Weigel and Glazebrook (2002) *Arabidopsis: A Laboratory Manual*, COLD SPRING HARBOR PRESS, Cold Spring Harbor, N.Y., 354 pages; Mersereau et al. (1990) *Gene* 90:149-151; Mattanovich, et al. (1989) *Nucl. Acids Res.* 17:6747)). Strain UIA143 cells transformed with pTiEHA105 were selected by their ability to grow on AB minimal medium (Watson, et al. (1975) *J. Bacteria* 123:255-264) using purified agar and mannopine (2 mg/mL) as a sole source of carbon and nitrogen for growth (Guyon et al. (1980) *Proc. Natl. Acad. Sci.* 77:2693-2697; Dessaux et al. (1987) *Molec. Gen. Genet.* 208:301-308).

The presence of pTiEHA105 was verified by polymerase chain reaction (PCR) using primers designed to amplify fragments of the pTiBo542 virD2 and virG genes, and further characterized by Southern blot analysis of total DNA prepared from candidate colonies probed with 32P-labeled DNA of pTiEHA101 purified by cesium chloride gradient centrifugation. This *Agrobacterium* strain (i.e., UIA143 containing pTiEHA105) is named DA2552.

EXAMPLE 4

Construction of a RecA-Deficient *Agrobacterium* Strain Harboring the Helper Plasmid pTiC58Δ

Strain Z707 was derived by replacing the entire T-DNA region of the pTiC58 plasmid of *Agrobacterium tumefaciens* strain C58 with the npt I gene of Tn903, which confers resistance to Kanamycin. The entire vir region of the resulting plasmid, herein called pTiC58Δ, was left intact (Hepburn et al. (1985) *J. Gen. Microbiol.* 131:2961-2969). The helper plasmid pTiC58Δ from strain Z707 was purified by cesium chloride gradient centrifugation and was electroporated into electrocompetent UIA143 cells. A transformant was selected on the basis of the pTiC58Δ plasmid-borne Kanamycin resistance gene and chromosomally borne Erythromycin resistance gene, and the strain was named DA2569. Presence of pTiC58Δ in DA2569 was verified by PCR amplification using primers to detect selected vir gene regions and by Southern blot analysis of total DNA prepared from DA2569 candidate colonies probed with 32P-labeled DNA of pTiC58Δ purified by cesium chloride gradient centrifugation from cells of strain Z707.

EXAMPLE 5

Construction of a RecA-Deficient *Agrobacterium* Strain Harboring the Helper Plasmid pMP90

*Agrobacterium tumefaciens* strain GV3101(pMP90) harbors a deleted version of pTiC58 called pMP90, from which the entire T-DNA region has been deleted and replaced with a gene conferring resistance to Gentamicin (Koncz and Schell (1986) *Mol. Gen. Genet.* 204:383-396). DNA of plasmid pMP90 is prepared by methods such as cesium chloride gradient centrifugation or the MACHEREY-NAGEL NUCLEOBOND XTRA MAXI KIT "LOW COPY" (MACHEREY-NAGEL Inc.; Bethelem, Pa.) and is electroporated into UIA143 cells. A transformant is selected on the basis of the pMP90 plasmid-borne Gentamicin resistance gene (100 μg/mL) and the strain is named DAt20538. Presence of pMP90 in DAt20538 is verified by PCR amplification using primers to detect selected vir gene regions and by Southern blot analysis of total DNA prepared from DAt20538.

EXAMPLE 6

Construction of a RecA-Deficient *Agrobacterium* Strain Harboring the Helper Plasmid pMP90RK The helper plasmid pMP90 described in Example 5 was further modified by the introduction (via double crossover homologous recombination) of a 42-kbp EcoR I fragment derived from plasmid pRK2013 (Figurski and Helinski (1979) *Proc. Natl. Acad. Sci. USA* 79:1648-1652). The 42-kbp fragment contains plasmid RK2-derived genes for plasmid replication and mobilization (e.g., trfA, tra1, tra2, tra3, and oriT), and a gene conferring resistance to Kanamycin. This manipulation replaced the Gentamicin resistance gene of plasmid pMP90, and the resulting plasmid was named pMP90RK (Koncz and Schell, supra). DNA of plasmid pMP90RK is prepared by methods such as cesium chloride gradient centrifugation or the MACHEREY-NAGEL NUCLEOBOND XTRA MAXI KIT "LOW COPY" and is electroporated into electrocompetent UIA143 cells. A transformant is selected on the basis of the pMP90RK plasmid-borne Kanamycin resistance gene and the strain is named DAt20539. Presence of pMP90RK in DAt20539 is verified by PCR amplification using primers to detect selected vir gene regions and by Southern blot analysis of total DNA prepared from DAt20539.

EXAMPLE 7

Electroporation of pDAB9292 DNA into *Agrobacterium* Strain DA2552

Electrocompetent DA2552 cells were prepared using a standard protocol (see Example 3). 50 μL of the competent DA2552 cells were thawed on ice and were transformed using 300 to 400 ng of plasmid pDAB9292 DNA. The DNA and cell mix was electroporated using prechilled electroporation cuvettes (0.2 cm) and a BIO-RAD GENE PULSER electroporator (BIO-RAD Inc.; Hercules, Calif.) with the following conditions: Voltage: 2.5 kV, Pulse length: 5 msec, Capacitance output: 25 μFarad, Resistance: 200 ohms. After electroporation, 1 mL of YEP (gm/L: Yeast Extract 10, Peptone 10, NaCl 5) broth was added to the cuvette and the cell-YEP suspension was transferred to a 15 mL culture tube. The cells were incubated at 28° C. with gentle agitation for four hours after which the culture was plated on YEP+agar containing Kanamycin at 50 μg/mL and Erythromycin at 150 μg/mL. The plates were incubated for two to four days at 28° C. and colonies were selected and streaked onto fresh YEP+agar plates with antibiotics as above and incubated at 28° C. for one to three days. These colonies were verified as *Agrobacterium* using the ketolactose test (Bouzar et al. (1995) in *Methods in Molecular Biology* (K. Gartland and M. Davey, eds.) *Agrobacterium Protocols* (Vol. 44) HUMANA PRESS, Totowa, N.J. pp. 9-13. Several ketolactose positive colonies were selected to start 3 mL YEP (with antibiotics) seed cultures that were grown overnight at 28° C. while shaking. 300 μL of each seed culture was used to inoculate a 200 mL YEP (with antibiotics) overnight culture grown at 28° C. while shaking at 200 rpm. Plasmid DNA was prepared from 165 mL of each 200 mL overnight culture using a MACHEREY-NAGEL NUCLEOBOND® XTRA MAXI PLASMID DNA PURIFICATION kit. The manufacturer's protocol was followed, except 30 mL each of buffer RES, LYS, and NEU was used. The eluted DNA was stored at 4° C.

Restriction enzyme digestion of the plasmid DNA with BamH I was used to validate the presence of pDAB9292 in these isolates, and colonies having the correct patterns were then further purified using two passages of single colony isolation. Plasmid DNA was prepared from overnight cultures as described above and restriction digest analysis was used to verify the presence of the intact pDAB9292. Plasmid DNA of the pDAB9292 vector originally used in the DA2552 transformation was included as a digested standard. Four separate digest reactions (Pst I, BamH I, Mfe I and Hind III) were run using 750 ng to 1 μg of DNA. The reaction was allowed to run one to two hours and was analyzed by agarose gel electrophoresis (0.8% w/v) and the DNA fragments were visualized by ethidium bromide staining. This *Agrobacterium* strain (i.e., DA2552 harboring pDAB9292) is named DAt13192. This strain provides the basis for a recombination-deficient "ternary" plant transformation system.

EXAMPLE 8

Electroporation of pDAB9292 DNA into *Agrobacterium* Strain GV3101(pMP90)

Cells of *Agrobacterium tumefaciens* strain GV3101 (pMP90) (Koncz and Schell, supra) were made electrocompetent by a standard protocol (see Example 3). 50 μL of the competent GV3101(pMP90) cells were thawed on ice and were transformed using 300 to 400 ng of plasmid pDAB9292 DNA. The DNA and cell mix was electroporated using prechilled electroporation cuvettes (0.2 cm) and a BIO-RAD GENE PULSER electroporator with the following conditions: Voltage: 2.5 kV, Pulse length: 5 msec, Capacitance output: 25 μFarad, Resistance: 200 ohms. After electroporation, 1 mL of YEP broth was added to the cuvette and the cell-YEP suspension was transferred to a 15 mL culture tube. The cells were incubated at 28° C. with gentle agitation for four hours after which the culture was plated on YEP+agar containing Kanamycin at 50 μg/mL and Gentamicin at 100 μg/mL. The plates were incubated for two to four days at 28° C. and colonies were selected and streaked onto fresh YEP+agar plates with antibiotics as above and incubated at 28° C. for one to three days. These colonies were verified as *Agrobacterium* using the ketolactose test. Several ketolactose positive colonies were selected to start 3 mL YEP (with antibiotics) seed cultures that were grown overnight at 28° C. while shaking. 300 μL of each seed culture was used to inoculate a 200 mL YEP (with antibiotics) overnight culture grown at 28° C. while shaking at 200 rpm. Plasmid DNA was prepared from 165 mL of each 200 mL overnight culture using a MACHEREY-NAGEL NUCLEOBOND® XTRA MAXI PLASMID DNA PURIFICATION. The manufacturer's protocol was followed, except 30 mL each of buffer RES, LYS and NEU was used. The eluted DNA was stored at 4° C.

Restriction enzyme digestion of the plasmid DNA with BamH I was used to validate the presence of pDAB9292 in these isolates, and colonies having the correct patterns were then further purified using two passages of single colony isolation. Plasmid DNA was prepared from overnight cultures as described above and restriction digest analysis was used to verify the presence of the intact pDAB9292. Plasmid DNA of the pDAB9292 vector originally used in the GV3101(pMP90) transformation was included as a digested standard. Four separate digest reactions (Pst I, BamH I, Mfe I and Hind III) were run using 750 ng to 1 μg of DNA. The reaction was allowed to run one to two hours and was analyzed by agarose gel electrophoresis (0.8% w/v) and the DNA fragments were visualized by ethidium bromide staining. The *A. tumefaciens* GV3101 isolate harboring the pMP90 Ti helper plasmid and pDAB9292 is called DAt20712.

EXAMPLE 9

Electroporation of pDAB9292 DNA into *Agrobacterium* Strain LBA4404

Cells of *Agrobacterium tumefaciens* strain LBA4404 (Ooms et al. (1982) *Plasmid* 7:15-29) were made electrocompetent by a standard protocol (see Example 3). 50 μL of the competent LBA4404 cells were thawed on ice and were transformed using 300 to 400 ng of plasmid pDAB9292 DNA. The DNA and cell mix was electroporated using prechilled electroporation cuvettes (0.2 cm) and a BIO-RAD GENE PULSER electroporator with the following conditions: Voltage: 2.5 kV, Pulse length: 5 msec, Capacitance output: 25 μFarad, Resistance: 200 ohms. After electroporation, 1 mL of YEP broth was added to the cuvette and the cell-YEP suspension was transferred to a 15 mL culture tube. The cells were incubated at 28° C. with gentle agitation for four hours after which the culture was plated on YEP+ agar containing Kanamycin at 50 μg/mL and Streptomycin at 250 μg/mL. The plates were incubated for two to four days at 28° C. and colonies were selected and streaked onto fresh YEP+agar plates with antibiotics as above and incubated at 28° C. for one to three days. These colonies were verified as *Agrobacterium* using the ketolactose test and were further purified using two passages of single colony isolation.

Several ketolactose positive colonies were selected to start 3 mL YEP (with antibiotics) seed cultures that were grown overnight at 28° C. while shaking. 300 μL of each seed culture was used to inoculate a 200 mL YEP (with antibiotics) overnight culture grown at 28° C. while shaking at 200 rpm. Plasmid DNA was prepared from 165 mL of each 200 mL overnight culture using a MACHEREY-NAGEL NUCLEOBOND® XTRA MAXI PLASMID DNA PURIFICATION kit. The manufacturer's protocol was followed, except 30 mL each of buffer RES, LYS and NEU was used. The eluted DNA was stored at 4° C.

The presence of the intact pDAB9292 plasmid was verified by restriction digest analysis. Plasmid DNA of the pDAB9292 vector originally used in the LBA4404 transformation was included as a digested standard. Three separate digest reactions (Pst I, BamH I, and Hind III) were run using 750 ng to 1 μg of DNA. The reaction was allowed to run one to two hours and was analyzed by agarose gel electrophoresis (0.8% w/v) and the DNA fragments were visualized by ethidium bromide staining. The *A. tumefaciens* LBA4404 isolate harboring pDAB9292 is called DAt20711. This strain provides the basis for a recombination-proficient "ternary" system.

EXAMPLE 10

Electroporation of pDAB9292 DNA into *Agrobacterium* Strain DAt20538

Electrocompetent DAt20538 cells are prepared using a standard protocol (see Example 3). 50 μL of competent DAt20538 cells are thawed on ice and are transformed using 300 to 400 ng of plasmid pDAB9292 DNA. The DNA and cell mix is electroporated using prechilled electroporation cuvettes (0.2 cm) and a BIO-RAD GENE PULSER electroporator with the following conditions: Voltage: 2.5 kV, Pulse length: 5 msec, Capacitance output: 25 μFarad, Resistance: 200 ohms. After electroporation, 1 mL of YEP broth are added to the cuvette and the cell-YEP suspension is transferred to a 15 mL culture tube. The cells are incubated at 28° C. with gentle agitation for four hours after which the culture is plated on YEP+agar containing Kanamycin at 50 μg/mL and Gentamicin at 100 μg/mL. The plates are incubated for two to four days at 28° C. and colonies are selected and streaked onto fresh YEP+agar plates with antibiotics as above and incubated at 28° C. for one to three days. These colonies are verified as *Agrobacterium* using the ketolactose test and ketolactose positive colonies are further isolated using two passages of single colony isolation.

Colonies are selected to start 3 mL YEP (with antibiotics) seed cultures that are grown overnight at 28° C. while shaking. 300 μL of each seed culture is used to inoculate a 200 mL YEP (with antibiotics) overnight culture grown at 28° C. while shaking at 200 rpm. Plasmid DNA is prepared from 165 mL of each 200 mL overnight culture using a MACHEREY-NAGEL NUCLEOBOND® XTRA MAXI PLASMID DNA PURIFICATION kit. The manufacturer's protocol is followed, except 30 mL each of buffer RES, LYS and NEU are used. The eluted DNA is stored at 4° C.

Restriction digest analysis is used to verify the presence of the intact pDAB9292 plasmid. Plasmid DNA of the pDAB9292 vector originally used in the DAt20538 transformation is included as a digested standard. Four separate digest reactions such as Pst BamHI, Mfe I and Hind III are run using 750 ng to 1 μg of DNA. The reaction is allowed to run one to two hours and is analyzed by agarose gel electrophoresis (0.8% w/v) and the DNA fragments are visualized by ethidium bromide staining. The *A. tumefaciens* DAt20538 isolate harboring pDAB9292 is called DAt20538 (pDAB9292).

EXAMPLE 11

Construction of Plant Transformation Vectors Having Multiple Repeated Sequence Elements and Introduction into *Agrobacterium* Strains The utility of an engineered *Agrobacterium tumefaciens* strain having a deficiency in RecA function in combination with the auxiliary vir genes provided by the 14.8 KpnI VirBCDG fragment is illustrated herein. A binary plant transformation vector, pDAB101513 (FIG. 4A), was constructed in *E. coli* cloning strain STBL2™ by a combination of standard cloning methods (as described, for example, in Sambrook et al. (1989, supra) and Ausubel et al. (1995, supra)) and GATEWAY™ technology (INVITROGEN). Binary vector pDAB101513 is based on the IncP-type replication origin of plasmid RK2, and the vector backbone harbors a bacterial gene conferring resistance to Spectinomycin (SpcR in FIG. 4) at 100 μg/mL The T-DNA border repeats are derived from the TL region of pTi15955. Within the Right Border (T-DNA Border B in FIG. 4) and triple Left Borders (T-DNA Border A in FIG. 4) of the T-DNA region of plasmid pDAB101513 are positioned four plant-expressible, plant-codon-optimized protein coding sequences (CDS), the transcription of each one being driven by a 1,991 bp maize ubiquitin) promoter with associated intron) (U.S. Pat. No. 5,510,474). Three of the coding regions encode separate Bt Cry1 proteins (Cry1Ca, SEQ ID NO:7; Cry1Fa, SEQ ID NO:9; and Cry1Ab, SEQ ID NO:11), each comprising around 3,500 bp. These coding regions were codon optimized for expression in maize plants using a maize (*Zea mays*) codon bias table calculated from analysis of 706 maize protein coding regions obtained from GENBANK deposits. Additional guidance regarding the design and production of synthetic genes can be found in, for example, WO 97/13402A1, U.S. Pat. No. 6,166,302, and U.S. Pat. No. 5,380,831. The three B.t protein coding regions are related to one another in the following fashion: The coding region for cry1Ca (SEQ ID NO:6) and the coding region for cry1Fa (SEQ ID NO:8) share 67% sequence homology; the coding regions for cry1Ca (SEQ ID NO:6) and cry1Ab (SEQ ID NO:10) share 69.5% sequence homology, and the coding regions for cry1Fa (SEQ ID NO:8) and cry1Ab (SEQ ID NO:10) share 67% sequence homology. Further, the C-terminal 1,600 bp of the CDS for cry1Ca, cry1Fa, and cry1Ab share 73% sequence homology. Each of these three coding regions is terminated by a 365 bp maize Per5 3' Untranslated Region (3'UTR) (U.S. Pat. No. 6,384,207). The fourth gene comprises a plant-codon-optimized aad1 coding region (SEQ ID NO:12) that encodes the AAD1 selectable marker protein (SEQ ID NO:13) (U.S. Pat. No. 7,838,733) The aad1 coding region is not related to the CDS for cry1Ca, cry1Fa, or cry1Ab. The coding region for aad1 was designed using a plant-codon bias table. A maize codon bias table was calculated from 706 maize protein coding sequences obtained from sequences deposited in GENBANK. Codon usage tables for tobacco (*Nicotiana tabacum,* 1268 CDS), canola (*Brassica napus,* 530 CDS), cotton (*Gossypium hirsutum,* 197 CDS), and soybean (*Glycine max*; ca. 1000 CDS) were downloaded from data at the website http://www.kazusa.or.jp/codon/. A biased codon set that comprises frequently used codons common to both maize and dicot datasets, in appropriate resealed average relative amounts, was calculated after omitting any redundant codon used less than about 10% of total codon uses for that amino acid in either plant type. The aad1 gene is temiinated by a maize Lipase 3'UTR (U.S. Pat. No. 7,179,902). Thus, within the 22,729 bp T-DNA region of pDAB101513, the four copies of the maize ubi1 promoter comprise a total of 7,964 bases arranged in four direct repeats of almost 2 kbp (kilobase pairs) each, with each repeat being 100% related to the other. The three copies of the Per5 3'UTR comprise a total of 1,095 bases arranged in three direct repeat units, each one being 100% related to the other, and the three coding regions cry1Ca, cry1Fa, and cry1Ab are arranged as direct repeats having between 67% and 73% homology to one another. In total, the T-region of pDAB101513 comprises about 86% highly repeated sequences, and may be conveniently illustrated below:

RB>Ubi1 promoter: cry1Ca CDS:Per5 3'UTR>Ubi1 promoter:cry1Fa CDS:Per5 3'UTR>Ubi1 promoter: cry1Ab CDS:Per5 3'UTR>Ubi1 promoter:aad1 CDS: Lip 3'UTR>LB The highly repeated nature of this construct required that the cloning steps be completed in the *E. coli* cloning strain STBL2™, which is specially engineered to maintain the integrity of clones containing such highly repeated DNA sequences.

Plasmid pDAB101513 was introduced by electroporation into electrocompetent cells of *A. tumefaciens* strain EHA105 (rendered Streptomycin resistant by virtue of a spontaneous chromosomal mutation), and Spectinomycin/Streptomycin-resistant isolates were verified by restriction digestion analysis to contain intact plasmid pDAB101513 prior to preparation of frozen glycerol stocks and storage at −80° C. This strain is named EHA105(pDAB101513). Numerous individual cultures established from cells obtained from frozen glycerol stocks of EHA105(pDAB101513) were found to contain re-arranged or deleted versions of the pDAB101513 plasmid. For maize transformations, bulk cells of strain EHA105(pDAB101513) were harvested from an agar plate inoculated from a frozen glycerol stock and used directly as described in Example 13.

Plasmid pDAB101513 was successfully introduced by electroporation into electrocompetent cells of *A. tumefaciens* strain DA2552 (essentially a RecA-deficient version of strain EHA105) to produce strain DA2552(pDAB101513). Transformants selected by means of resistance to Erythromycin and Spectinomycin were validated by restriction enzyme digestion of plasmid DNA prior to preparation of frozen glycerol stocks and storage at −80° C. Numerous individual cultures established from cells obtained from frozen glycerol stocks were found to contain intact pDAB101513 plasmid. Bulk cells of strain DA2552 (pDAB101513) were harvested from an agar plate inoculated from a frozen glycerol stock and used for maize transformations (Example 13).

Plasmid pDAB101513 was successfully introduced by electroporation into electrocompetent cells of *A. tumefaciens* strain DAt13192 (strain DA2552 harboring plasmid pDAB9292) to produce strain DAt13192(pDAB101513). Transformants selected by means of resistance to Erythromycin, Kanamycin, and Spectinomycin were validated by restriction enzyme digestion of plasmid DNA prior to preparation of frozen glycerol stocks and storage at −80° C. Numerous individual cultures established from cells obtained from the frozen stocks were found to contain intact pDAB101513 plasmid. Bulk cells of strain DAt13192 (pDAB101513) were harvested from an agar plate inoculated from a frozen glycerol stock and used for maize transformations (see Example 13).

In similar fashion, a derivative of pSB11 (the shuttle vector of the superbinary system) was constructed having a T-DNA region analogous to that of pDAB101513. Multiple attempts to construct a superbinary plasmid by standard methods in LBA4404(pSB1) were unsuccessful. All attempts resulted in isolation of highly rearranged and deleted pSB1-based cointegrant plasmids.

EXAMPLE 12

Construction of Plant Transformation Vector pDAB101514 Having Multiple Repeated Sequence Elements and Introduction into *Agrobacterium* Strains The utility of an engineered *A. tumefaciens* strain having a deficiency in RecA function in combination with the auxiliary vir genes provided by the 14.8 KpnI VirBCDG fragment is further illustrated herein. A binary plant transformation vector, pDAB101514 (FIG. 4B), was constructed in *E. coli* cloning strain STBL2™ by a combination of standard cloning methods and GATEWAY™ technology. The structure of binary vector pDAB101514 is nearly the same as that of pDAB101513 (previous Example) with the exception of the expression elements used to drive expression of the cry1Ca gene. The transcription of the cry1Ca CDS in pDAB101514 is driven by a 1429 bp sugarcane bacilliform virus promoter (SCBV; Tzafrir et al. (1998) *Plant Molec. Biol.* 38:347-356). The 5'UTR is comprised essentially of intron 6 of the maize alcohol dehydrogenase gene (GENBANK Accession X04049), flanked by twenty bases of exon 6 and eleven bases of exon 7. The transcription of this gene is terminated by a potato pinII 3'UTR (An et al. (1989) *Plant Cell* 1:115-122). The expression elements used to control expression of the cry1Fa, cry1Ab, and aad1 genes are the same as were employed in pDAB101513. Thus, within the 22,586 bp T-DNA region of pDAB101514, the three copies of the maize ubi1 promoter comprise a total of 5,973 bases arranged in three direct repeats of almost 2 kbp each, with each repeat being 100% related to the other. The two copies of the Per5 3'UTR comprise a total of 730 bases arranged in two direct repeat units, each one being 100% related to the other, and the three coding regions cry1Ca, cry1Fa, or cry1Ab are arranged as direct repeats having between 67% and 73% DNA sequence homology to one another. In total, the T-region of pDAB101514 comprises about 76% highly repeated DNA sequences, and the physical arrangement may be conveniently illustrated below:

RB>SCBV promoter:cry1Ca CDS:pinII 3'UTR>Ubi1 promoter:cry1Fa CDS:Per5 3'UTR>Ubi1 promoter: cry1Ab CDS:Per5 3'UTR>Ubi1 promoter:aad1 CDS: Lip 3'UTR>LB The highly repeated nature of this construct required that the cloning steps be completed in the *E. coli* cloning strain STBL2™, which is specially engineered to maintain the integrity of clones containing such highly repeated DNA sequences.

Plasmid pDAB101514 was introduced by electroporation into electrocompetent cells of *A. tumefaciens* strain EHA105 (rendered Streptomycin resistant by virtue of a spontaneous chromosomal mutation), and Spectinomycin/Streptomycin-resistant isolates were verified by restriction digestion analysis to contain intact plasmid pDAB101514 prior to preparation of frozen glycerol stocks and storage at −80° C. This strain was named EHA105(pDAB101514). Numerous individual cultures established from EHA105(pDAB101514) cells obtained from frozen glycerol stocks were found to contain re-arranged or deleted versions of the pDAB101514 plasmid. For maize transformations, bulk cells of strain EHA105(pDAB101514) were harvested from an agar plate inoculated from a frozen glycerol stock and used by methods disclosed in Example 13.

Plasmid pDAB101514 was successfully introduced by electroporation into electrocompetent cells of *A. tumefaciens* strain DA2552 (essentially a RecA-deficient version of strain EHA105) to produce strain DA2552(pDAB101514). Transformants selected by means of resistance to Erythromycin and Spectinomycin were validated by restriction enzyme digestion of plasmid DNA prior to preparation of frozen glycerol stocks and storage at −80° C. Numerous individual cultures established from cells obtained from frozen glycerol stocks were found to contain intact pDAB101514 plasmid. Bulk cells of strain DA2552 (pDAB101514) were harvested from an agar plate inoculated from a frozen glycerol stock and used for maize transformations by methods disclosed in Example 13.

Plasmid pDAB101514 was successfully introduced by electroporation into cells of *A. tumefaciens* strain DAt13192 (strain DA2552 harboring plasmid pDAB9292) to produce strain DAt13192(pDAB101514). Transformants selected by means of resistance to Erythromycin, Kanamycin, and Spectinomycin were validated by restriction enzyme digestion of plasmid DNA prior to preparation of frozen glycerol stocks and storage at −80° C. Numerous individual cultures established from DAt13192(pDAB101514) cells obtained from the frozen stocks were found to contain intact pDAB101514 plasmid. Bulk cells of strain DAt13192(pDAB101514) were harvested from an agar plate inoculated from a frozen glycerol stock and used for maize transformations by methods disclosed in Example 13.

In similar fashion, a derivative of pSB11 (the shuttle vector of the superbinary system) was constructed having a T-DNA region analogous to that of pDAB101514. Multiple attempts to construct a superbinary plasmid by standard methods in LBA4404(pSB1) were unsuccessful. All attempts resulted in isolation of highly rearranged and deleted pSB1-based cointegrant plasmids.

EXAMPLE 13

Transformation of Maize by *Agrobacterium* Strains Harboring Binary Vectors pDAB101513 and pDAB101514

*Agrobacterium*-Mediated Transformation of Maize: Seeds from a Hi-II F1 cross (Armstrong et al. (1991) *Maize Genet. Coop. Newslett.* 65:92-93) were planted into 5-gallon-pots containing a mixture of 95% METRO-MIX 360 soilless growing medium (SUN GRO HORTICULTURE; Bellevue, Wash.) and 5% clay/loam soil. The plants were grown in a greenhouse using a combination of high pressure sodium and metal halide lamps with a sixteen hours light/eight hours dark photoperiod. Controlled sib-pollinations were performed to obtain immature F2 embryos for transformation. Maize ears were harvested at approximately eight to ten days post-pollination when immature embryos were between 1.0 mm and 2.0 mm in size.

Infection and co-cultivation: Maize ears were dehusked and surface sterilized by scrubbing with liquid soap, immersing in 20% commercial bleach (containing 5% sodium hypochlorite) for about 20 minutes, then rinsing three times with sterile water. A suspension of *A. tumefaciens* cells harboring pDAB101513 or pDAB101514, binary vectors having three genes encoding the Bt Cry1Ca, Cry1Fa, and Cry1Ab proteins, and containing the aad-1 plant selectable marker gene, was prepared by transferring one or two loops of bacteria (grown for two to three days at 28° C. on YEP agar medium containing appropriate antibiotics) into 5 mL of liquid infection medium (LS Basal Medium (Linsmaier and Skoog (1965) *Physiologia Plantarum* 18:100-127), N6 vitamins (Chu et al. (1975) *Scientia Sinica* 18:659-668), 1.5 mg/L 2,4-Dichlorophenoxyacetic acid (2,4-D), 68.5 gm/L sucrose, 36.0 gm/L glucose, 6 mM L-proline, pH 5.2] containing 200 μM acetosyringone. The solution was vortexed until a uniform suspension was achieved, and the concentration was adjusted to a final optical density of approximately 0.4 at 550 nm.

Immature embryos were isolated directly into a microcentrifuge tube containing 2 mL of the infection medium. The medium was removed and replaced with 1 mL of the *Agrobacterium* solution and the *Agrobacterium*/embryo solution was incubated for five to ten minutes at room temperature. Embryos were then transferred to cocultivation medium (LS Basal Medium, N6 vitamins, 1.5 mg/L 2,4-D, 30.0 gm/L sucrose, 6 mM L-proline, 0.85 mg/L AgNO3, 2.8 gm/L GELLAN GUM™ (PHYTOTECHNOLOGY LABORATORIES; Lenexa, Kans.), pH 5.8) containing 200 μM acetosyringone and cocultivated for three to four days at 20° C. in the dark.

After cocultivation, the embryos were transferred to resting medium containing MS salts and vitamins (Frame et al., 2011, *Genetic Transformation Using Maize Immature Zygotic Embryos. in Plant Embryo Culture Methods and Protocols: Methods in Molecular Biology*, T. A. Thorpe and E. C. Yeung (Eds), SPRINGER SCIENCE AND BUSINESS MEDIA, LLC. pp 327-341), 6 mM L-proline, 100 mg/L myo-inositol, 500 mg/L MES (2-(N-morpholino) ethanesulfonic acid monohydrate; PHYTOTECHNOLOGIES LABR.), 30 gm/L sucrose, 1.5 mg/L 2,4-D, 0.85 $AgNO_3$, 250 mg/L Cefotaxime, 2.8 gm/L GELLAN GUM™, pH 5.8. Approximately seven days later, embryos were transferred to the same medium supplemented with 100 nM Haloxyfop. Transformed isolates were identified after approximately eight weeks and were bulked up by transferring to fresh selection medium at two-week intervals for regeneration and analysis.

Regeneration and seed production: For regeneration, the cultures were transferred to "28" induction medium (MS salts and vitamins, 30 gm/L sucrose, 5 mg/L Benzylaminopurine, 0.25 mg/L 2, 4-D, 250 mg/L Cefotaxime, 2.5 gm/L GELLAN GUM™, pH 5.7) supplemented with 100 nM Haloxyfop. Incubation was for one week under low-light conditions (14 $\mu Em^{-2} s^{-1}$), then one week under high-light conditions (approximately 89 μEm$^{-2}$ s$^{-1}$). Tissues were subsequently transferred to "36" regeneration medium (same as induction medium except lacking plant growth regulators). When plantlets were 3 cm to 5 cm in length, they were transferred to glass culture tubes containing SHGA medium [(Schenk and Hildebrandt salts and vitamins, PHYTOTECHNOLOGIES LABR.), 1.0 gm/L myo-inositol, 10 gm/L sucrose and 2.0 gm/L GELLAN GUM™, pH 5.8] to allow for further growth and development of the shoot and roots. Plants were transplanted to the same soil mixture as described earlier and grown to flowering in the greenhouse. Samples of plant tissues were harvested and used in insect bioassays by methods disclosed in Example 14 and for molecular and biochemical analyses. Controlled pollinations for seed production are conducted.

Those skilled in the art of maize transformation will understand that other methods are available for maize transformation and for selection of transformed plants when other plant expressible selectable marker genes (e.g., herbicide tolerance genes) are used.

EXAMPLE 14

In vitro Bioassays of Leaf Samples Against Maize Insect Pests

The lepidopteran species assayed were the corn earworm (CEW; *Helicoverpa zea* (Boddie)), European corn borer (ECB; *Ostrinia nubilalis* (Hübner)), and fall armyworm (FAW; *Spodoptera frugiperda* (J. E. Smith)). Eggs for these insects were obtained from BENZON RESEARCH (Carlisle, Pa.).

First Tier Bioassay: High-throughput 96-well Bioassay: 96-well trays (TPP-US; St. Louis, Mo.) were partially filled with a 2% agar solution (SIGMA-ALDRICH) and agar was allowed to solidify. Using a standard hand-held paper punch, three ⅛ inch diameter leaf discs were sampled for each of the two insect species (CEW and FAW) tested in this format. One leaf disc was placed in a single well of the 96-well plate; there were three plates for each insect tested (one for each replicate/leaf disc). An egg-seeding device was used to administer insect eggs into each well of the 96-well plate. Plates were then sealed with perforated sticky lids and also enclosed with the plastic lid that accompanies the plates. Plates were held at 30° C., 40% Relative Humidity (RH), sixteen hours light/eight hours dark for three days. Grading was conducted using a 0-1-2 scale, in which 0 indicated <25% leaf disc damage, 1 indicated 25-50% leaf disc damage, and 2 indicated >50% leaf disc damage within each well. Damage scores for each test were averaged and used alongside protein expression analysis to conduct correlation analyses. Plants whose average insect damage score was 0.67 or less were considered active against the tested pest.

Second Tier Bioassay: 32-well Bioassay: 32-well trays (C-D INTERNATIONAL; Pitman, N.J.) were partially filled with a 2% agar solution and agar was allowed to solidify. Leaf sections approximately 1 inch square were taken from each plant and placed singly into wells of the 32-well trays. One leaf piece was placed into each well, and two leaf pieces were tested per plant and per insect. Insects (ECB and FAW) were mass-infested using a paintbrush, placing ten to twenty neonate larvae into each well. Trays were sealed with perforated sticky lids which allowed ventilation during the test. Trays were placed at 28° C., 40% RH, sixteen hours light/eight hours dark for three days. After the duration of the test, a simple percent damage score was taken for each leaf piece. Damage scores for each test were averaged and used alongside protein expression analysis to conduct correlation analyses. Plants whose average insect damage ratings were 25% or less were considered active against the tested pest.

Statistical Analysis: All analyses were conducted in JMP 8.0.2 (SAS INSTITUTE Inc., Cary, N.C.). One-way ANOVA analysis was used to determine significant differences between the treatments and the negative control plants for insect damage data. The Tukey-Kramer HSD comparison of means was also used to further evaluate significant differences among the treatments. In addition, linear regression (least fit squares) analysis was used to correlate quantitative protein expression with insect activity measurements.

Bioassay results are summarized in Table 2.

EXAMPLE 15

Biochemical and Molecular Characterization of Maize Tissues Transformed with pDAB101513

Multiple transformation experiments were performed with engineered *A. tumefaciens* strains EHA105 (pDAB101513), DA2552(pDAB101513) and DAt13192 (pDAB101513). Copy numbers of the four transgenes in transgenic $T_0$ plants were estimated by hydrolysis probe assays (Bubner and Baldwin (2004) *Plant Cell Rep.* 23:263-271) using gene-specific oligonucleotides. Protein extracts from plants with one to three copies ("Low Copy") of the genes were further examined for production of the Bt Cry1Ca, Cry1Fa, and Cry1Ab proteins, and for the AAD1 protein, by ELISA methods using commercially produced antibody kits (ENVIROLOGIX™, Portland, Mass.). Some plants were found that produced all four proteins (Table 3). In addition, leaf pieces from the plants were bioassayed for activity against three maize insect pests: corn earworm (CEW, *Helicoverpa zea*), fall armyworm (FAW, *Spodoptera frugiperda*) and European corn borer (ECB, *Ostrinia nubilalis*) in feeding assays (EXAMPLE 14). Some plants were found that had all four transgenes in low copy number, produced all four proteins, and had insect activity against all three pests (Table 4). No transformed plants meeting these criteria were obtained from experiments using the EHA105 (pDAB101513) or DA2552(pDAB101513) strains (Table 4). Thus, a feature of strain DAt13192, comprising a deletion of the chromosomal recA gene, further comprising a full set of pTiBo542-derived vir genes harbored on pTiEHA105, and even further comprising a partial set of pTiBo542-derived vir genes harbored on the 14.8 KpnI VirBCDG fragment of pDAB9292, is that it is able to efficiently produce transformed maize plants with large T-DNA regions comprised of highly repeated sequence elements.

EXAMPLE 16

Biochemical and Molecular Characterization of Maize Tissues Transformed with pDAB101514

Multiple transformation experiments were performed with engineered *A. tumefaciens* strains EHA105 (pDAB101514), DA2552(pDAB101514), and DAt13192 (pDAB101514). Copy numbers of the four transgenes in transgenic $T_0$ plants were estimated by hydrolysis probe assays (Bubner and Baldwin, supra) using gene-specific oligonucleotides. Protein extracts from plants with one to three copies ("Low Copy") of the genes were further examined for production of the Bt Cry1Ca, Cry1Fa, and Cry1Ab proteins, and for the AAD1 protein, by ELISA methods using commercially produced antibody kits (ENVIROLOGIX™, Portland, Mass.). In addition, leaf pieces from the plants were bioassayed for activity against three maize insect pests in feeding assays (Example 14). Some plants were found that had all four transgenes in low copy number, produced all four proteins, and had insect activity against all three pests (Table 5). No transformed plants meeting these criteria were obtained from experiments using the EHA105(pDAB101514) or DA2552(pDAB101514) strains. Thus, a feature of strain DAt13192, comprising a deletion of the chromosomal recA gene, further comprising a full set of pTiBo542-derived vir genes harbored on pTiEHA105, and even further comprising a partial set of pTiBo542-derived vir genes harbored on the 14.8 KpnI VirBCDG fragment of pDAB9292, is that it is able to efficiently produce transformed maize plants with large T-DNA regions comprised of highly repeated sequence elements.

EXAMPLE 17

Identification and Characterization of a Neutral Integration Site in the *Agrobacterium tumefaciens* LBA4404 Chromosome The plant-inducible picA/pgl locus of the *A. tumefaciens* strain C58 chromosome (GENBANK Accession AE0009243) was identified as a non-essential gene into which DNA fragments could be integrated (Rong et al. (1990) *J Bacteriol.* 172:5828-5836; Rong et al. (1991) *J. Bacteriol.* 173:5110-5120). A similar neutral integration site in the genome of *A. tumefaciens* strain LBA4404 has not been reported. We describe here the identification and sequencing of a genomic region of LBA4404 that includes sequences partially homologous to the C58 picA/pgl locus. Cells of LBA4404 (INVITROGEN) were grown in YM medium (gm/L: yeast extract, 0.4; mannitol, 10; NaCl, 0.1; $MgSO_4$ $7H_2O$, 0.2; $K_2HPO_4$ $3H_2O$, 0.5) at 30° C. overnight. Genomic DNA was prepared from a 1 mL culture using the EASY DNA kit (INVITROGEN) according to the manufacturer's protocols. Degenerate primers were designed based upon two regions of homology between the C58 PicA protein sequence and homologues identified from *Arabidopsis thaliana, Caldicellulosiruptor saccharolyticus, Alkaliphilus metalliredigenes*, and *Clostridium acetobutylicum*. LBA4404 genomic DNA was used as a template for the polymerase chain reaction (PCR) using HERCULASE™ MASTER MIX (STRATAGENE; San Diego, Calif.) and degenerate primers AtnilA1Fa (5'-GACAGTCCNAATACSGAYGG-3'; SEQ ID NO:14; corresponding to amino acids 273-279 of the C58 PicA protein) and AtnilA3R (5'-GTYTTSAGNCGSAGSCCSCGRTCSGT-3'; SEQ ID NO:15, corresponding to the complementary strand coding for amino acids 364-369 of the C58 PicA protein). Thermocycling conditions used were: one cycle of 94° C., 2 minutes; 25 cycles of (94° C., 30 seconds; 55° C., 30 seconds; 72° C., 60 seconds); one cycle of 72° C., 7 minutes. Degenerate nucleotide designations in the primer sequences correspond to DNA nucleotides as follows: N=A, C, G, or T; Y=T or C; R=A or G; and S=C or G. A 285 base pair (bp) product was isolated, cloned into the vector pCR2.1-TOPO (INVITROGEN) in *Escherichia coli* TOP10 cells (INVITROGEN), and the DNA sequence was determined. The sequence was found to be homologous, but not identical, to a region of the C58 picA gene (85% sequence identity), and the LBA4404 genomic region that it represents is referred to herein as the nilA fragment.

Additional primers complementary to the 285 bp LBA4404 nilA fragment were designed to be used as anchors for PCR amplification of genomic fragments flanking both ends of the 285 bp sequence. These were paired in the PCR reactions with primers designed from sequences of the flanking regions of the C58 picA gene. Sequences of amplified fragments originating from within the 285 bp sequence and extending into both nilA fragment flanking regions were determined and used to design other primers for subsequent PCR reactions. Using LBA4404 genomic DNA template with primers nilA2F (5'-CCATCCTCATAACACCAGCT-3'; SEQ ID NO:16) and nilA2R (5'-GCAGATCATCGATACGACCA-3'; SEQ ID NO:17), an approximately 2 kilobase (kbp) PCR fragment was generated and cloned into pCR®-BLUNT II/XL-TOPO® using the TOPO TA cloning kit (INVITROGEN) to produce plasmid pDOW3719 (FIG. 2). Sequence analysis of the insert fragment of pDOW3719 yielded an 1,796 bp sequence (SEQ ID NO:18) which comprises a longest open reading frame (ORF) that encodes a putative protein of 531 amino acids. A shorter ORF in the same reading frame encodes a putative protein of 523 amino acids. The LBA4404 523 amino acid putative protein shows 88% similarity, 85% identity with the C58 PicA protein. The coding sequences for the LBA4404 523 amino acid putative protein and the C58 PicA protein have 81% identity. Thus, the nilA fragment of LBA4404 represents a genomic segment that includes a putative gene that is substantially diverged from the C58 picA gene. In this disclosure, the 1.8-kbp genomic sequence represented by SEQ ID NO:18 is referred to as the nilA locus.

Plasmid pDOW3719, having the colE1 origin of replication, is not expected to replicate autonomously in *A. tumefaciens* cells. DNA of plasmid pDOW3719 was used to transform cells of *A. tumefaciens* strain LBA4404 by electroporation. Selection for Kanamycin resistance (harbored on pDOW3719) identified transformants that had integrated pDOW3719 into the chromosome of LBA4404 via recombination mediated by the 1.8-kbp homology regions present in the LBA4404 chromosome and on pDOW3719. Such an integration event results in the creation of a linear copy of the pDOW3719 vector plasmid sequence flanked on each side by the now-duplicated 1.8-kbp homology region. Kanamycin resistant LBA4404 transformants were isolated and screened for insertion of pDOW3719 by PCR analysis. Genomic DNA preparations of the transformants were used as template in PCR reactions with five primers sets: i) M13F primer paired with M13R primer, which flank the insert in pDOW3719, ii) M13F primer paired with primer AS4R (comprising bases complementary to residues 1041 to 1060 of SEQ ID NO:18), iii) M13F primer paired with primer AS10R (comprising bases complementary to residues 1,320 to 1,337 of SEQ ID NO:18), iv) M13F primer paired with primer AS11R (comprising bases complementary to residues 1,391 to 1,406 of SEQ ID NO:18), and v) M13R primer paired with primer AS9F (comprising bases 634 to 649 of SEQ ID NO:18). In control reactions, all of these primer sets amplified expected sized fragments when pDOW3719 plasmid DNA was used as template. However, when genomic DNA from a Kanamycin resistant LBA4404 transformant was used as template, PCR using the M13F and M13R primer pair did not yield amplified products, indicating that no intact (non-integrated) pDOW3719 plasmid DNA was co-purified with the genomic DNA. PCR analysis of the genomic DNA samples with the other four primer pairs showed production of expected sized DNA fragments. These results indicate that the Kanamycin resistance of the LBA4404 transformants is conferred by pDOW3719 DNA which has integrated into the genome.

One such transformant [LBA4404nilA-int1] was used to test the effect that the genomic insertion into the nilA locus has on the ability of the strain to transform *Arabidopsis thaliana*. Binary vector pDAB3779, which contains a plant expressible gene encoding the PAT protein (which confers resistance to the herbicide BASTA™) was transformed into cells of strains LBA4404nilA-int1 and LBA4404, with selection for Spectinomycin resistance. These strains were then used to conduct *Arabidopsis* transformation experiments using the methods of Weigel and Glazebrook (supra). No difference was seen in the transformation frequencies obtained with the two strains. Thus, a feature of the embodiments and methods described herein is that insertion of a foreign DNA fragment into the chromosomal nilA locus of *A. tumefaciens* strain LBA4404 that comprises SEQ ID NO:18 has no effect on the growth or plant transformation capability of such engineered strain.

EXAMPLE 18

Construction of a Suicide Derivative of pDOW3719 for Integration into the LBA4404 nilA Locus The insertion of a multiple cloning site in the nilA locus cloned in pDOW3719 was accomplished by splice overlap extension (SOE) PCR (Horton et al. (1990) *BioTechniques* 8:528-535). SOE PCR reactions were carried out using HERCULASE™ master mix according to the manufacturer's protocols. A portion of the nilA locus was amplified using pDOW3719 DNA as template with primer nilA5' (5'-CCGGCTCTTCCAGCTCCTCATGCACGAACAAC-GAGAAACGAGC-3'; SEQ ID NO:19) paired with primer nilA_MCS_SOER (5'-GAATGGTGAAACCTCTAGAT-TAATTAA GGATCCCCGGGTACCGAAAAGCCCGA-CATTGC-3'; SEQ ID NO:20) to produce an approximately 800 bp fragment. A second portion of the nilA locus was amplified using pDOW3719 DNA as template and primer nilA_MCS_SOEF (5'-GCAATGTCGGGCTTTTCGG TACCCGGGGATCCTTAATTAATCTAGAGGTTTCAC-CATTC-3'; SEQ ID NO:21) paired with primer nilA3' (5'-GGAATTCTCAGTGGCTTTCATGGGTTTTCTCG-3'; SEQ ID NO:22) to produce an approximately 900 bp fragment. The resulting fragments were then gel purified (NUCLEOSPIN™, CLONTECH; Mountain View, Calif.), and used as template for amplification with primers nilA5' and nilA3' to yield a 1.6-kbp fragment, which sequence is disclosed as SEQ ID NO:23 (nilA MCS). The resultant fragment was digested with Pvu I and Sap I (NEB) and ligated to pBCSK+sacBl DNA (INVITROGEN) digested with the same restriction enzymes, using T4 DNA ligase (NEB). *E. coli* TOP10 cells were transformed with the ligation mixture, and transformants were selected on LB soy agar (TEKNOVA; Hollister, Calif.) supplemented with 30 μg/mL Chloramphenicol. Clones were screened by restriction digestion with Pvu I and Kpn I (NEB). The nilA locus region of positive clones was sequence verified, and the resulting plasmid was named pDOW3721. A feature of pDOW3721 is that a multiple cloning site (MCS) containing recognition sequences for restriction enzymes Sph I, Kpn I, Sma I, BamH I, Pac I, Ase I and Xba I is flanked on one side by 852 bp of LBA4404-derived bases, and on the other side by 745 bp of LBA4404-derived bases.

Thus, a foreign DNA fragment may be cloned into the MCS of pDOW3721, and thence integrated into the LBA4404 chromosomal nilA locus by virtue of homologous recombination mediated by the LBA4404-derived flanking sequences. Single crossover events, by means of which the entire pDOW3721 plasmid sequence is integrated into the LBA4404 chromosome, may be resolved into double crossover events by counterselection on sucrose containing media. On such media, the sucrose is converted to a toxic product upon enzymolysis by the SacB protein encoded by the sacB gene (Reid and Collmer (1987) *Gene* 57:239-246; Quandt et al. (1993) *Gene* 127:15-21). Thus, transformants able to survive on sucrose-containing growth medium will have undergone a second crossover event that eliminates the pDOW3721 plasmid vector backbone from the chromosome, leaving behind the disrupted nilA locus containing the integrated foreign DNA fragment. Many reports have shown for the last ten years that the transfer of vector backbone sequences is quite common. The ratio of the plants that acquired the backbone sequences in transformants ranged typically between 20% and 50%, and was sometimes as high as 75% or more.

As one exemplification of the utility of pDOW3721, the 14.8 KpnI VirBCDG fragment was prepared from plasmid pSB1 and ligated to Kpn I digested pDOW3721 DNA, using T4 DNA ligase. *E. coli* TOP10 cells were transformed with the ligation mixture, and transformants were selected on LB soy agar supplemented with 30 μg/mL Chloramphenicol. Clones were screened by restriction digestion with EcoR I and Hind III. The resultant plasmid was named pDOW3722.

EXAMPLE 19

Identification of Nucleotide Sequences Upstream and Downstream of nilA

The LBA4404nilA-int1 strain of *A. tumefaciens*, containing a genomic integration of plasmid pDOW3719 (FIG. 2 and Example 18), was used to identify additional sequences positioned upstream and downstream of the nilA genomic region. pDOW3719 contains a 1,796 bp PCR amplicon of the *A. tumefaciens* strain LBA4404 nilA locus cloned into PCR-BLUNT II/XL-TOPO® (INVITROGEN). This plasmid was integrated into the genome of *A. tumefaciens* strain LBA4404 via homologous recombination. Colonies which contained the integrated plasmid were identified by resistance to Kanamycin (Example 17). The integrated plasmid, and the elements contained within it, may be used as tools for the isolation and characterization of additional nucleotide sequences via a "plasmid rescue" technique.

Genomic DNA (gDNA) was prepared from cells of the LBA4404nilA-int1 strain by a protocol for bacterial genomic DNA isolation (Sambrook et al., supra). One microgram of gDNA was individually digested with the following enzymes (all obtained from NEB): Hind III, BamH I, Pst I, Asc I, and Sac II. These restriction enzymes were chosen specifically to produce gDNA fragments that map upstream and downstream of the nilA locus. The Hind III, BamH I, and Pst I restriction enzymes were selected because their recognition sites are unique within the pDOW3719 sequence. Moreover, these enzyme recognition sites are located at the junctions between the nilA locus amplicon fragment and the PCR-BLUNT II/XL-TOPO® vector (FIG. 2). Cleavage of gDNA with these enzymes and self ligation of the resulting fragments thus results in a plasmid rescue fragment which contains the uncharacterized genomic sequences ligated adjacent to the M13 forward universal primer or the M13 reverse universal primer binding sites of the pDOW3917 plasmid. Such clones are isolated by transforming the ligation mixture into *E. coli* cells, with selection for the Kanamycin resistance gene harbored by pDOW3917.

Further, the pDOW3719 plasmid does not contain recognition sites for the Asc I and Sac II restriction enzymes. Therefore, gDNA fragments generated by these restriction enzymes would produce a chimeric DNA fragment which spans the entire length of the integrated pDOW3719 plasmid sequence and includes the gDNA regions which flank both sides of the integrated pDOW3719 plasmid.

The gDNA fragments which resulted from restriction enzyme digestion as described above were self-ligated using T4 Ligase (ROCHE APPLIED SCIENCES; Indianapolis, Ind.). The ligation products were transformed into *E. coli* ONESHOT® TOP10 CELLS (INVITROGEN) and plated on LB media containing Kanamycin (50 μg/mL). Individual colonies were selected and plasmid DNA was isolated and characterized via plasmid restriction enzyme digestion patterns. Clones which contained plasmids exhibiting a consistent restriction enzyme digestion banding pattern as compared to one another were advanced for use in sequencing reactions.

The nucleotide sequences of the gDNA upstream and downstream from the nilA locus were determined using a "genome walking" technique. Sequencing primers corresponding to the known gDNA sequence (as present in pDOW3719) were designed and used with the CEQ™ DYE TERMINATOR CYCLE SEQUENCING KIT according to the manufacturer's recommendations (BECKMAN COULTER; Fullerton, Calif.). From the determined sequence, a second set of primers, located in previously unknown genomic sequence, was designed and used to generate additional sequencing data. This process was repeated until all of the available gDNA nucleotide sequence was determined. This technique generated 2,936 bp of sequence upstream from the nilA locus, and 4,361 bp of sequence downstream from the nilA locus. In combination with the 1,796 bp of the previously identified nilA locus, the newly identified upstream and downstream flanking sequences regions netted a 9,093 bp sequence comprising the nilA genomic region (SEQ ID NO:24), which extends in both directions from the originally identified nilA locus.

EXAMPLE 20

Construction of a Vector for Integration into the LBA4404 nilA Genomic Region

Figure 3:
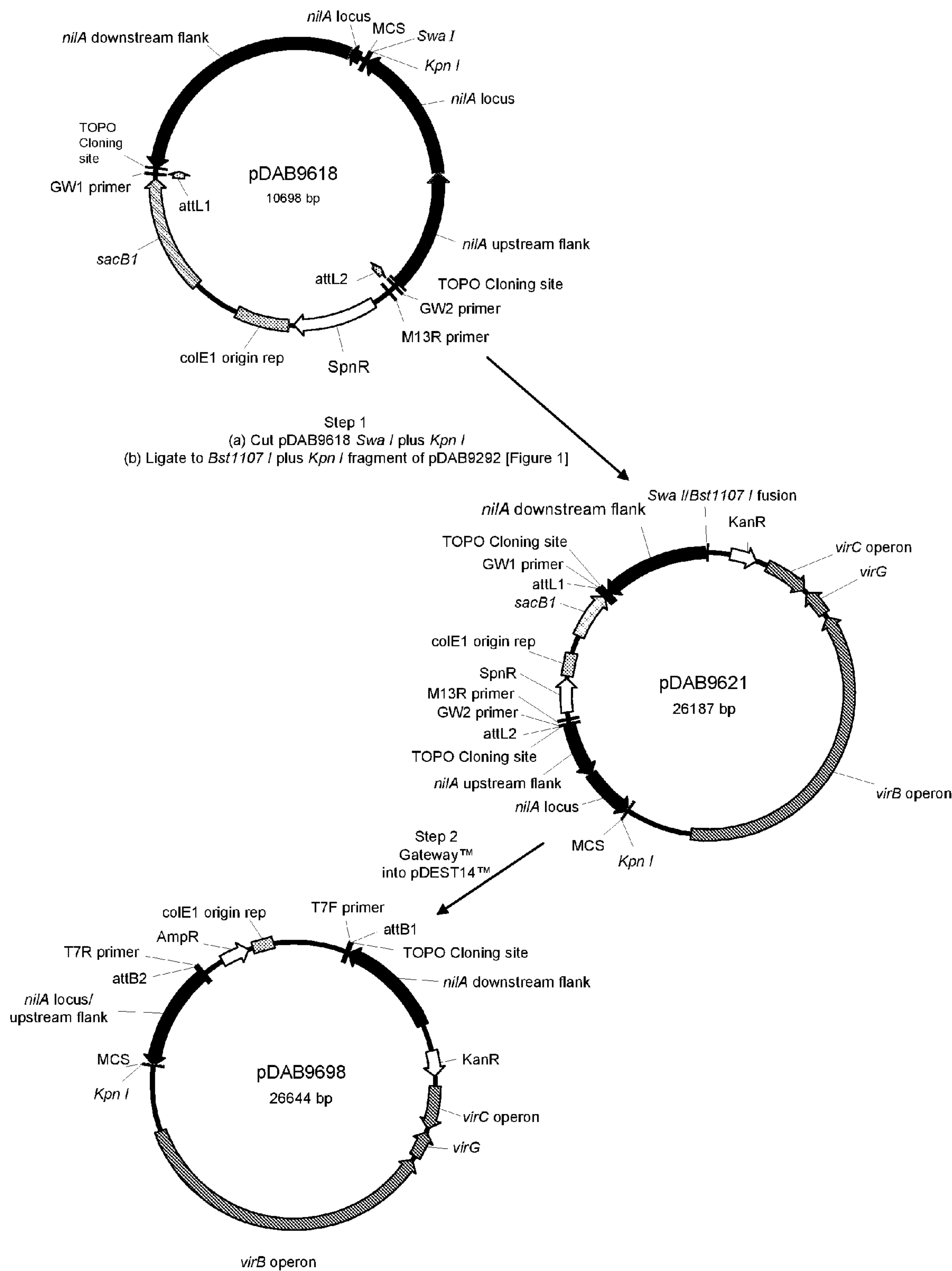
FIG. 3 shows a cloning scheme for the construction of plasmid pDAB9698.

An integration vector for homology-mediated integration of foreign DNA sequences into the *A. tumefaciens* LBA4404 nilA genomic region was designed and constructed. A 6.3-kbp fragment of the nilA genomic region spanning the nilA locus was PCR amplified using the FAILSAFE™ PCR KIT (EPICENTRE®, Madison, Wis.). The amplified fragment was ligated into the PCR®8/GW/TOPO® vector (INVITROGEN), and positive clones were confirmed via restriction enzyme digestion and DNA sequence verification. The resulting vector, pDAB9615, was further modified by the addition of an oligonucleotide fragment containing multiple unique restriction enzyme recognition sites. These restriction sites, flanked by 3,244 bp and 3,128 bp regions of the nilA genomic region, serve as cloning sites for the introduction of foreign nucleotide sequences. The resulting vector was named pDAB9618 (FIG. 3).

A 15,549 bp fragment containing the 14.8 KpnI VirBCDG fragment of pSB1 and a bacterial Kanamycin resistance gene was prepared by digestion of pDAB9292 DNA with Kpn I plus Bst1107 I. This fragment was then ligated to DNA of pDAB9618 that had been digested with Kpn I plus Swa I, to produce vector pDAB9621 (FIG. 3). The GATEWAY® reaction was then used to move the portion of pDAB9621 containing the 14.8 KpnI VirBCDG fragment and bacterial Kanamycin resistance gene, flanked on each side by 3 kbp of LBA4404 nilA genomic region sequences, into the GATEWAY® PDEST™14 vector via AN L-R CLONASE® reaction (INVITROGEN). The resulting plasmid, pDAB9698 (FIG. 3, SEQ ID NO:25), was confirmed via restriction enzyme digestion and DNA sequencing reactions. pDAB9698 served as an integration vector for integrating the pTiBo542-derived vir genes from pSB1 (harbored on the 14.8 KpnI VirBCDG fragment) into the nilA chromosomal region of *A. tumefaciens* strain LBA4404.

EXAMPLE 21

Chromosomal Integration of the 14.8 KpnI VirBCDG Fragment Via Homologous Recombination DNA of plasmid pDAB9698 was produced using a NUCLEOBOND® AX ANION EXCHANGE CHROMATOGRAPHY PLASMID DNA ISOLATION KIT (MACHEREY-NAGEL). The purified plasmid DNA was electroporated into *A. tumefaciens* LBA4404 CELLS (INVITROGEN). Briefly, 500 ng of plasmid DNA was incubated with the cells at 4° C. for ten minutes. This mixture was pipetted into an ice-chilled 0.2 cm GENE PULSER® CUVETTE (BIO-RAD) and electroporated using the BIO-RAD GENE PULSER with the following settings: capacitance output 25 μFarad, capacitance extender 960μ'Farad, resistance 200 ohms, and voltage 2.5 kVolts. Immediately after electroporation, 950 μL of SOC medium (INVITROGEN) was added and the mixture was transferred to a Falcon 2059 tube (BECTON DICKINSON AND CO.; Franklin Lakes, N.J.). The transformed cells were then incubated at 28° C. for five to six hours. After incubation, the cells were plated on separate YEP medium plates containing Kanamycin (50 μg/mL). The plates were grown inverted at 28° C. for 36 to 48 hours. Single colonies were picked and propagated in 5 mL of liquid YEP containing Kanamycin (50 μg/mL) for approximately 36 hours at 28° C. These cultures were used to prepare glycerol stock cultures by vigorous mixing with an equal volume of 100% sterile glycerol, followed by freezing and storage at −80° C.

EXAMPLE 22

Phenotypic and Molecular Confirmation of the Chromosomal Integration of the 14.8 KpnI VirBCDG Fragment pDAB9698, having the colE1 origin of replication, is not expected to replicate autonomously in *A. tumefaciens* cells. Thus, upon transformation of pDAB9698 DNA into LBA4404 cells, stable Kanamycin resistance results from the integration of DNA of pDAB9698 into autonomously replicating *Agrobacterium* genetic elements. These plasmid integrants will fall into four classes that can be used according to various embodiments of the *Agrobacterium* strains and methods for their use as described herein. The first class comprises cells in which pDAB9698 DNA has integrated into a site remote from the nilA genomic region by means of nonhomologous recombination. These cells should be Kanamycin resistant by virtue of the Kanamycin resistance gene adjacent to the 14.8 KpnI VirBCDG fragment, and additionally should be resistant to Ampicillin by virtue of the Ampicillin resistance gene harbored on the pDAB9698 backbone vector (pDEST™14). The second class comprises cells in which the pDAB9698 DNA has integrated into the autonomously replicating pAL4404 Ti helper plasmid (natively resident in LBA4404) by virtue of homologous recombination mediated by the pTiBo542-derived VirB-CDG genes present on pDAB9698 and the pTiACH5-derived VirBCDG genes present on pAL4404. These cells should also be resistant to both Kanamycin and Ampicillin. The third class comprises cells in which pDAB9698 DNA has integrated into the LBA4404 nilA genomic region by virtue of a single homologous recombination (crossover) event mediated by either of the approximately 3-kbp nilA genomic region sequences harbored on pDAB9698, and which flank the 15,549 bp fragment containing the 14.8 KpnI VirBCDG fragment of pSB1 and the Kanamycin resistance gene. These cells should also be resistant to both Kanamycin and Ampicillin. The fourth class comprises cells in which the single crossover event of class 3 cells above undergoes a second crossover event mediated by the now-duplicated 3-kbp nilA genomic region sequences that are generated as a consequence of the single crossover event. Depending upon which of the flanking 3-kbp nilA genomic region sequences generated the single crossover event, and which of these flanking sequences generates the second crossover event, the resultant cells should either be Kanamycin sensitive, and Ampicillin resistant, or Kanamycin resistant and Ampicillin sensitive. Preferred cells as described herein comprise the latter class, that is, cells that are Kanamycin resistant and Ampicillin sensitive. These double crossover events, which do not contain the pDEST™14 plasmid backbone, are desirable as they do not contain superfluous genetic elements such as the colE1 replication origin and Ampicillin resistance gene.

Putative transformants isolated in Example 21 were screened for a desirable double homologous recombination-mediated integration event. Kanamycin-resistant isolates having the 15,549 bp fragment containing the 14.8 KpnI VirBCDG fragment of pSB1 and the Kanamycin resistance gene (and lacking the pDEST™14 vector backbone) were identified via sensitivity to Ampicillin. The putative transformants were grown in 3 mL of YEP containing Kanamycin (50 μg/mL) at 28° C. for approximately 36 hours. These cultures were then streaked onto solid YEP media containing various single antibiotics as follows (concentrations in μg/mL): Rifampicin, 100; Kanamycin, 50; Streptomycin, 125; Chloramphenicol, 50; Erythromycin, 200; Tetracycline, 12.5; and Ampicillin, 100. The plates were incubated at 28° C. for 48 hours and colony growth was scored. A strain was identified that was resistant to Kanamycin, Rifampcin (chromosomal marker), and Streptomycin (pAL4404 marker; Ooms et al., supra). Moreover, the strain was sensitive to Chloramphenicol, Erythromycin, and Tetracycline. Most significantly, the strain was sensitive to Ampicillin. This drug screen phenotype is indicative of a desirable double crossover homologous recombination event, wherein the 15,549 bp fragment containing the 14.8 KpnI VirBCDG fragment of pSB1 and the Kanamycin resistance gene are integrated into the *A. tumefaciens* LBA4404 chromosome. This strain is called DAt16174.

The presence of the pTiBo542-derived VirBCDG genes in strain DAt16174 was further confirmed by molecular characterization. Genomic DNA of strain DAt16174 was isolated using a bacterial genomic DNA isolation protocol (Sambrook et al., supra and updates thereof). PCR primers were designed to amplify overlapping fragments of the chromosomally integrated VirBCDG genes. PCR reactions using the primers described in Table 6 were completed using the FAILSAFE™ PCR KIT (EPICENTRE®) per the manufacturer's directions. Due to the large total molecular size of the integrated VirBCDG genes, the amplifications were done to produce five overlapping fragments. Amplicons of the expected size were purified from agarose gels using the QIAEX II GEL EXTRACTION KIT (QIAGEN; Valencia, Calif.) according to the manufacturer's protocol. These fragments were cloned into the PCR2.1®-TOPO® TA vector using the PCR2.1®-TOPO®TA CLONING® KIT (INVITROGEN). Bacterial colonies suspected to contain clones of the PCR amplicons were confirmed via restriction enzyme digestion. The DNA sequences of the amplicon fragments were determined using the CEQ™ DYE TERMINATOR CYCLE SEQUENCING KIT according to the manufacturer's instructions, and the sequencing data were analyzed using SEQUENCHER™ version 4.1.4 software (GENE CODES CORP.; Ann Arbor, Mich.). The resulting sequences produced a 22-kbp contiguous sequence which spanned the entire 15,549 bp fragment containing the 14.8 KpnI VirBCDG fragment of pSB1 and the Kanamycin resistance gene, plus both of the approximately 3-kbp flanking nilA genomic regions, and extended further into the upstream and downstream nilA genomic regions (thereby including LBA4404 chromosomal sequence which was not originally contained in pDAB9698).

The *Agrobacterium tumefaciens* identity of strain DAt16174 was verified via the ketolactose test. Putatively transformed colonies were streaked out on lactose agar and incubated at 28° C. for 48 hours. The plates were then flooded with Benedict's Solution and monitored at room temperature. Isolates which turned the Benedict's Solution and underlying agar from blue to yellow were thus confirmed to be *Agrobacterium.*

A feature of *A. tumefaciens* strain DAt16174 is that it may be advantageously used as a plant transformation agent for the transfer of T-DNA genes from binary vectors having replication origins of, for example, the IncP, IncW, or VS1 classes. In broad terms, the introduced binary vector may have a replication origin of any class capable of replication in *Agrobacterium* while being compatible with the pTi origin of replication (and associated functions) of the pAL4404 plasmid resident in DAt16174. Thus, it is within the range of possible uses of strain DAt16174 that more than one binary vector plasmid may be co-resident in strain DAt16174 if the plasmids have compatible replication origins (i.e., are of different incompatibility groups). Selection for such introduced binary vectors should not rely on bacterial selectable marker genes conferring either Kanamycin, Rifampicin, or Streptomycin resistance, as the DAt16174 strain is resistant to these three antibiotics.

Binary vectors can replicate autonomously in both *E. coli* and *Agrobacterium* cells. They comprise sequences, framed by the right and left T-DNA border repeat regions, that may include a selectable marker gene functional for the selection of transformed plant cells, a cloning linker, cloning polylinker, or other sequence which can function as an introduction site for genes destined for plant cell transformation. They can be transformed directly into *Agrobacterium* cells by electroporation, by chemically mediated direct DNA transformation, introduced by bacterial conjugation, or by other methodologies. The *Agrobacterium* used as host cell harbors at least one plasmid carrying a vir region. The vir region is necessary to provide Vir proteins to perform all the requisite functions involved in the transfer of the T-DNA into the plant cell. The plasmid carrying the vir region is commonly a mutated Ti or Ri plasmid (helper plasmid) from which the T-DNA region, including the right and left T-DNA border repeats, have been deleted. Examples of *Agrobacterium* strains that contain helper plasmids and are useful for plant transformation, include, for example, LBA4404, GV3101(pMP90), GV3101(pMP90RK), GV2260, GV3850, EHA101, EHA105, and AGL1. Numerous examples of binary vector systems are reviewed by Hellens et al. (2000, *Trends Plant Sci.* 5:446-451).

Additionally, the plant transformation advantages conferred upon strain LBA4404(pSB1) (used in the superbinary system) by the pTiBo542-derived virB operon (which includes the genes virB1, virB2, virB3, virB4, virB5, virB6, virB7, virB8, virB9, virB10, and virB11), the virG gene, the virC operon (which comprises genes virC1 and virC2) and the part of the virD operon comprising gene virD1, as harbored on the pSB1 plasmid, are retained in strain DAt16174. Because the superbinary vir genes listed above are integrated into the LBA4404 chromosome, strain DAt16174 is referred to as a SUPERCHROME strain. In contrast to the superbinary system, use of strain DAt16174 does not require the formation of unstable superbinary plasmids via homologous recombination between pSB1 and shuttle vectors such as pSB11. A further benefit of the SUPERCHROME strain is that standard binary vectors may be introduced into the strain for plant transformation.

EXAMPLE 23

Biochemical and Molecular Characterization of Maize Tissues Transformed with Various *Agrobacterium* Strains Harboring pDAB101556

Figure 5:
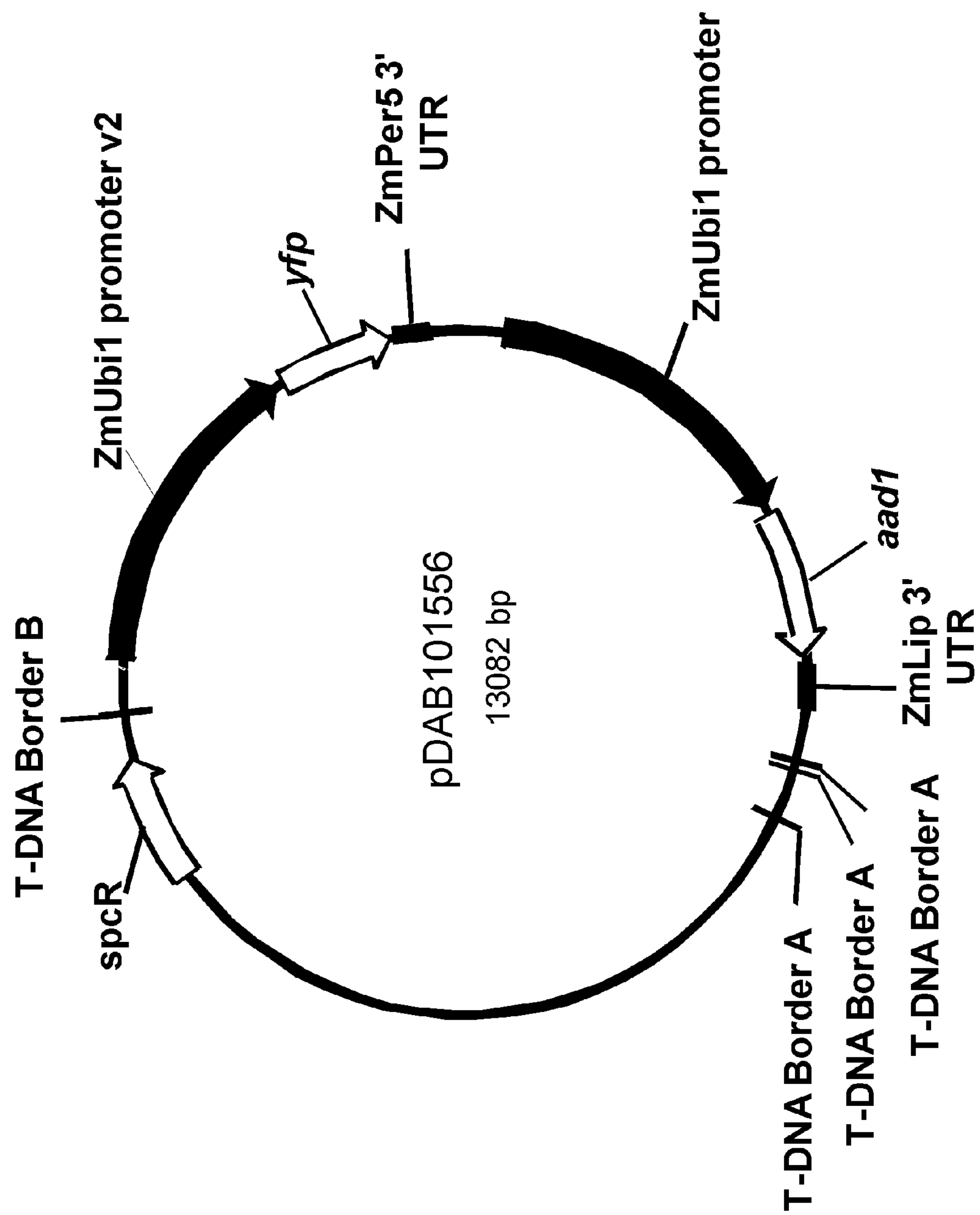
FIG. 5 shows a map of binary vector plasmid pDAB101556.

A binary plant transformation vector, pDAB101556 (FIG. 5), was constructed by a combination of standard cloning methods and GATEWAY™ technology. Binary vector pDAB101556 is based on the IncP-type replication origin of plasmid RK2, and the vector backbone harbors a bacterial gene conferring resistance to Spectinomycin at 100 μg/mL. The T-DNA border repeats are derived from the TL region of pTi15955. Within the Right Border (RB) and multiple Left Borders (LB) of the T-DNA region of plasmid pDAB101556 are positioned two plant-expressible protein coding sequences (CDS). The first gene (selectable marker) comprises the coding region for the AAD1 selectable marker protein (SEQ ID NO:13) (U.S. Pat. No. 7,838,733), which is under the transcriptional control of a 1,991 bp maize ubiquitin) promoter with associated intron) (U.S. Pat. No. 5,510,474). This gene is terminated by a maize Lipase 3'UTR (U.S. Pat. No. 7,179,902). The second gene (screenable marker) comprises a CDS for a yellow fluorescent protein (YFP, essentially as disclosed in U.S. Pat. No. 7,951,923) transcription of which is controlled by a maize ubiquitin 1 promoter with associated intron 1. This gene is terminated by a maize Per5 3'UTR (U.S. Pat. No. 6,384,207).

Plasmid pDAB101556 was successfully introduced by electroporation into cells of *A. tumefaciens* strain LBA4404 to produce strain LBA4404(pDAB101556). This strain/plasmid combination thus comprises a standard binary plant transformation system. Transformants selected by means of resistance to Streptomycin and Spectinomycin were validated by restriction enzyme digestion of plasmid DNA prior to preparation of frozen glycerol stocks and −80° C. storage. Bulk cells of strain LBA4404(pDAB101556) were harvested from an agar plate inoculated from a frozen glycerol stock and used for maize transformations by methods disclosed in Example 24.

Plasmid pDAB101556 was successfully introduced by electroporation into cells of *A. tumefaciens* strain DAt13192 (see Example 7) to produce strain DAt13192 (pDAB101556). This strain/plasmid combination thus comprises a recombination-deficient ternary plant transformation system. Transformants selected by means of resistance to Erythromycin, Kanamycin, and Spectinomycin were validated by restriction enzyme digestion of plasmid DNA prior to preparation of frozen glycerol stocks and storage at −80° C. Bulk cells of strain DAt13192(pDAB101556) were harvested from an agar plate inoculated from a frozen glycerol stock and used for maize transformations by methods disclosed in Example 24.

Several attempts were made to introduce DNA of plasmid pDAB101556 into strain DAt20711 (see Example 9), a recombination-proficient ternary system. In all cases, plasmid pDAB101556 was found to be unstable in this strain and a Dat20711(pDAB101556) strain was not constructed.

Plasmid pDAB101556 was successfully introduced by electroporation into cells of *A. tumefaciens* strain DAt16174 (Example 22) to produce strain DAt16174(pDAB101556). This strain/plasmid combination thus comprises a SUPERCHROME/binary plant transformation system. Transformants selected by means of resistance to Streptomycin, Kanamycin, and Spectinomycin were validated by restriction enzyme digestion of plasmid DNA prior to preparation of frozen glycerol stocks and storage at −80° C. Bulk cells of strain DAt16174(pDAB101556) were harvested from an agar plate inoculated from a frozen glycerol stock and used for maize transformations by methods disclosed in Example 24.

EXAMPLE 24

Transformation of Maize by *Agrobacterium* Strains Harboring Binary Vector pDAB101556

Immature Embryo Production: Seeds from a B104 inbred were planted into 3.5-inch SVD pots with METRO MIX 360 (SUN GRO HORTICULTURE Inc.; Bellevue, Wash.). When the plants reached the V4-V5 growth stage, they were transplanted into 4-gallon pots containing a 1:1 mix of METRO MIX 360 and PROFILE GREENS GRADE calcined clay (PROFILE PRODUCTS LLC; Buffalo Grove, Ill.), with 20 grams of OSMOCOTE 19-6-12, and 20 grams of IRONITE™ as additives. The plants were grown in a greenhouse using a combination of 1000 W HPS (high pressure sodium) and 1000 W MH (metal halide) lamps set to a 16:8 light/dark photoperiod if outside light did not exceed 450 W/m$^2$. In order to obtain immature embryos for transformation, controlled sib or self pollinations were performed.

Immature embryos were isolated at 10 to 13 days post-pollination when embryos were approximately 1.6 to 2.0 mm in size.

Infection and co-cultivation: Maize ears were surface sterilized by immersing in 20% commercial bleach with LIQUINOX™ detergent (one or two drops per 500 mL) for 20 minutes and triple-rinsed with sterile water. A suspension of *Agrobacterium* cells containing binary vector pDAB101556 was prepared from bacteria grown on AB solid medium at 20° C. for two to three days, followed by growth on YEP solid medium at 28° C. for one to two days. Both the AB and YEP media contained appropriate antibiotics supplements as described in Example 23 for each *Agrobacterium* strain tested with binary vector pDAB101556. Loopfuls of cells scraped from a YEP plate were transferred into 10 to 15 mL of liquid infection medium comprising: MS salts (Frame et al., supra), ISU Modified MS Vitamins (Frame et al., supra), 3.3 mg/L Dicamba-ethanol, 68.4 gm/L sucrose, 36 gm/L glucose, 700 mg/L L-proline, pH 5.2, and containing 100-200 μM acetosyringone. The solution was gently pipetted up and down using a sterile 5 mL pipette or vortex mixer until a uniform suspension was achieved, and the concentration was adjusted to an optical density of about 1.0 at 600 nm ($OD_{600}$) using a Hewlett-Packard P8452a spectrophotometer.

Co-cultivation: Immature embryos were isolated directly into a micro centrifuge tube containing 2 mL of the infection medium. The medium was removed and replaced with 1 to 2 mL of fresh infection medium, then replaced with 1.5 mL of the *Agrobacterium* solution. The *Agrobacterium* and embryo solution was incubated for 5 minutes at room temperature and then transferred to co-cultivation medium which contained MS salts, ISU Modified MS Vitamins, 3.3 mg/L Dicamba-ethanol, 30 gm/L sucrose, 700 mg/L L-proline, 100 mg/L myo-inositol, 100 mg/L Casein Enzymatic Hydrolysate, 15 mg/L $AgNO_3$, 100-200 acetosyringone, and 2.3 gm/L GELRITE™ (SIGMA-ALDRICH; St. Louis, Mo.), at pH 5.8. Co-cultivation incubation was for three days in the dark at 20° C.

Resting and Selection: After co-cultivation, the embryos were transferred to a non-selection MS-based resting medium containing MS salts, ISU Modified MS Vitamins, 3.3 mg/L Dicamba-ethanol, 30 gm/L sucrose, 700 mg/L L-proline, 100 mg/L myo-inositol, 100 mg/'L Casein Enzymatic Hydrolysate, 15 mg/L $AgNO_3$, 0.5 gm/L MES, 250 mg/L Cefotaxime, and 2.3 gm/L GELRITE™, at pH 5.8. Incubation was continued for seven days in the dark at 28° C. Following the seven-day resting period, the embryos were transferred to Selective Medium. For selection of maize tissues transformed with a superbinary or binary plasmid containing a plant expressible aad-1 selectable marker gene, the MS-based resting medium (above) was used supplemented with Haloxyfop. The embryos were first transferred to Selection Medium I containing 100 nM Haloxyfop and incubated for two weeks, and then transferred to Selection Medium II with 500 nM Haloxyfop and incubated for an additional two weeks. Transformed isolates were obtained over the course of approximately five weeks at 28° C. in the dark. If necessary, recovered isolates were bulked up by transferring to fresh Selection Medium II for another two weeks before being transferred to regeneration media.

Those skilled in the art of maize transformation will understand that other methods of selection of transformed plants are available when other plant expressible selectable marker genes (e.g., herbicide tolerance genes) are used.

Regeneration I: Following the selection process, cultures were transferred to an MS-based Regeneration Medium I containing MS salts, ISU Modified MS Vitamins, 60 gm/L sucrose, 350 mg/L L-proline, 100 mg/L myo-inositol, 50 mg/L Casein Enzymatic Hydrolysate, 1 mg/L $AgNO_3$, 250 mg/L Cefotaxime, 2.5 gm/L GELRITE™ and 500 nM Haloxyfop, at pH 5.8. Incubation was continued for two weeks at 28° C. in the dark.

Regeneration II: The cultures were transferred to an MS-based Regeneration Medium II containing MS salts, ISU Modified MS Vitamins, 30 gm/L sucrose, 100 mg/L myo-inositol, 250 mg/L Cefotaxime, 2.5 gm/L GELRITE™, and 500 nM Haloxyfop, at pH 5.8. After three weeks at 28° C. under 16/8 hours photoperiod, with white fluorescent light conditions (approximately 80 $\mu Em^{-2} s^{-1}$), plantlets were excised and transferred to an MS-based or (½ MS-based) shoot/root elongation medium composed of MS salts (or ½ MS salts), ISU Modified MS Vitamins, 0.5 gm/L MES, 30 gm/L sucrose, 100 mg/L myo-inositol, 2.5 gm/L GELRITE™, at pH 5.8. When plantlets reached 4 to 6 cm in length, they were transferred to the growth chamber and eventually to the greenhouse.

Seed production: Regenerated plants were transplanted into 3.5-inch SVD pots with METRO MIX 360 and placed in a growth chamber to harden off. When plants reached the V3 growth stage they were moved to the greenhouse, and at the V4/V5 growth stage, they were transplanted into 5-gallon pots containing a 1:1 mix of METRO MIX 360 and PROFILE GREENS GRADE calcined clay, with 20 grams of OSMOCOTE 19-6-12, and 20 grams of IRONITE™ as additives. The plants were grown in the greenhouse under a 16:8 light/dark photoperiod. T1 seed was produced by performing controlled pollinations (backcross to B104). Seed was harvested six weeks after pollination.

Multiple maize transformation experiments were performed with engineered *A. tumefaciens* strains LBA4404 (pDAB101556), DAt13192(pDAB101556), and DAt16174 (pDAB101556), and transgenic calli selected on inhibitory concentrations of Haloxyfop were carried forward for plantlet regeneration and further studies. In total, 16 events were retained in the LBA4404(pDAB101556) transformations, 49 events were retained in the DAt13192(pDAB101556) transformations, and 60 events were retained in the DAt16174(pDAB101556) transformations (Table 7).

Copy numbers of the aad-1 transgene in transgenic TO plants were estimated by hydrolysis probe assays ((Bubner and Baldwin, supra) using gene-specific oligonucleotides. Southern blot analyses of NcoI-cleaved DNA prepared from the selected events by a cetyl trimethylammonium bromide extraction method were performed using a PCR amplified fragment of the aad-1 gene as 32P-labeled probe. Further, the presence of integrated backbone vector sequences originating from pDAB101556 was detected by hydrolysis probe analyses.

Thus, strain DAt16174, a SUPERCHROME strain comprising a full set of pTiACH5-derived vir genes harbored on pAL4404, and further comprising a partial set of pTiBo542-derived vir genes integrated into the LBA4404 chromosome at the nilA locus, is able to efficiently produce transformed maize plants. Further, while having a somewhat lower overall transformation efficiency than that obtained with the ternary strain, the quality of SUPERCHROME-produced events is superior, with 90% of the events produced having single copy inserts with no detectable backbone contamination.

While this invention has been described in certain example embodiments, which are intended as illustrative of a few aspects of the invention, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

TABLE 1

Representative incompatibility groups and some example plasmids that are classified as belonging to these incompatibility groups.

| Incompatibility Group | Plasmids |
|---|---|
| FI | F, R386 |
| FII | R1 |
| FIII | Col B-K99, Col B-K166 |
| FIV | R124 |
| I | R62, R64, R483 (at least five subgroups) |
| J | R391 |
| N | R46 |
| O | R724 |
| P | RP4, RK2 |
| Q | RSF1010 |
| T | R401 |
| W | R388, S-a |

TABLE 2

Summary of in vitro bioassay results.

| Construct | Mean CEW Score (96-well assay) | Mean FAW Score (96-well assay) | Mean ECB % Damage (32-well assay) |
|---|---|---|---|
| Negative Control | 1.64 | 1.78 | 75.9 |
| 101513 | 0.59 | 0.88 | 17.4 |
| 101514 | 0.80 | 0.78 | 12.0 |

TABLE 3

Production (in ppm; parts per million) of the AAD1, Cry1Ca, Cry1Fa, and Cry1Ab proteins in maize plants transformed with binary vector pDAB101513.

| Event Name | AAD1 | Cry1Ca | Cry1Fa | Cry1Ab |
|---|---|---|---|---|
| 101513[37]-008.002 | 830 | 370 | 160 | 84 |
| 101513[37]-020.001 | 550 | 410 | 210 | 100 |
| 101513[39]-011.002 | 380 | 270 | 150 | 27 |
| 101513[44]-031.003 | 740 | 300 | 100 | 40 |
| 101513[45]-022.002 | 380 | 270 | 86 | 32 |
| 101513[45]-023.001 | 300 | 340 | 160 | 31 |
| 101513[49]-040.002 | 220 | 270 | 170 | 21 |
| 101513[49]-040.003 | 210 | 410 | 220 | 26 |
| 101513[49]-041.001 | 340 | 270 | 200 | 21 |

TABLE 4

Results of maize transformation experiments with strains of *A. tumefaciens* harboring plasmid pDAB101513.

| A Strain | B Embryos Treated | C Regenerable events (% X-form. efficiency) | D $T_0$ Events Analyzed | E Events with all 4 genes (%) | F Low-Copy Events with all 4 genes (%) | G Events of Col. F producing all 4 proteins (%) | H Events of Col. G active against all three pests (%) |
|---|---|---|---|---|---|---|---|
| EHA105 | 2469 | 6 (0.24) | 4 | 1 (25) | 1 (25) | 0 (0) | 0 (0) |
| DA2552 | 630 | 0 (0) | 0 | 0 (0) | 0 (0) | 0 (0) | 0 (0) |
| DAt13192 | 1945 | 34 (1.75) | 25 | 21 (84) | 14 (56) | 9 (64) | 9 (100) |

TABLE 5

Results of maize transformation experiments with strains of *A. tumefaciens* harboring plasmid pDAB101514.

| A Strain | B Embryos Treated | C Regenerable events (% X-form. efficiency) | D $T_0$ Events Analyzed | E Events with all 4 genes (%) | F Low-Copy Events with all 4 genes (%) | G Events of Col. F producing all 4 proteins (%) | H Events of Col. G active against all three pests (%) |
|---|---|---|---|---|---|---|---|
| EHA105 | 3499 | 11 (0.31) | 11 | 2 (18) | 1 (50) | 0 (0) | 0 (0) |
| DA2552 | 771 | 0 (0) | 0 | 0 (0) | 0 (0) | 0 (0) | 0 (0) |
| DAt13192 | 926 | 17 (1.83) | 15 | 12 (80) | 9 (75) | 8 (89) | 6 (75) |

TABLE 6

PCR primers used for molecular confirmation of integration of the 15,549 by fragment containing the 14.8 KpnI VirBCDG fragment of pSB1 and Kanamycin resistance gene into the nilA genomic region of the *Agrobacterium tumefaciens* strain DAt16174 chromosome.

| Primer Pair | SEQ ID NO: | Primer Name | Primer Sequence (5' to 3') | Amplicon Size |
|---|---|---|---|---|
| 1 | SEQ ID NO: 26<br>SEQ ID NO: 27 | H3-2 Down<br>Set2 5' | ATCTTACCTTCCTTTTCGTTTTCCAAC<br>CTGCTTGGATGCCCGAGGCATAGAC | 4,248 bp |

TABLE 6-continued

PCR primers used for molecular confirmation of integration of the 15,549 by fragment containing the 14.8 KpnI VirBCDG fragment of pSB1 and Kanamycin resistance gene into the nilA genomic region of the *Agrobacterium tumefaciens* strain DAt16174 chromosome.

| Primer Pair | SEQ ID NO: | Primer Name | Primer Sequence (5' to 3') | Amplicon Size |
|---|---|---|---|---|
| 2 | SEQ ID NO: 28 | Vir Screen 1 5' | CATCCAAGCAGCAAGCGCGTTACG | 7,696 bp |
| | SEQ ID NO: 29 | Vir Screen 4 3' | GTCTATGCCTCGGGCATCCAAGCAG | |
| 3 | SEQ ID NO: 30 | Vir Screen 5 5' | GAGACCGTAGGTGATAAGTTGCCC | 6,917 bp |
| | SEQ ID NO: 31 | Vir Screen 8 3' | TCTCATTTAGGGGCTGGCTCCAAC | |
| 4 | SEQ ID NO: 32 | VirG | TGCGAGCAACATGGTCAAACTCAG | 3,650 bp |
| | SEQ ID NO: 33 | VirB 1 3' | GACATGCAGAACAACGAGAAACGA | |
| 5 | SEQ ID NO: 34 | PSB1-1 5' | GCACACCGAAATGCTTGGTGTAGA | 4,126 bp |
| | SEQ ID NO: 35 | nilA For1 | GGCCGTGCACGGCATCAATCTCGAA | |

TABLE 7

Analyses of transgenic events produced by three *Agrobacterium* strains harboring plasmid pDAB101556.

| *Agrobacterium* System | Total Events With Inserts | Transformation Frequency (%) | % With Single-Copy Inserts | % With Single-Copy Inserts, and Backbone-Free | No. With Single-Copy Inserts, and Backbone-Free |
|---|---|---|---|---|---|
| Ternary DAt13192(pDAB101556) | 60 | 8.5 | 33 | 75 | 15 |
| SUPERCHROME DAt16174(pDAB101556) | 49 | 6 | 43 | 90 | 19 |
| Binary LBA4404(pDAB101556) | 16 | 3 | 88 | 86 | 14 |

What is claimed is:

1. A method for transforming a plant, comprising contacting a cell of the plant with an *Agrobacterium* strain that is deficient in Rec A function, wherein the *Agrobacterium* strain comprises:

at least one pTi helper plasmid comprising a 14.8 KpnI VirBCDG fragment of pSB1; and a different pTi plasmid comprising at least one disarmed T-DNA region that includes (i) at least a right T-DNA border and (ii) exogenous DNA adjacent to the border, wherein the pTi helper plasmid and the pTi plasmid comprising at least one disarmed T-DNA region have differing origins of replication relative to each other, thus eliminating the need to form a co-integrant hybrid vector (HV) containing both the 14.8 KpnI fragment and the exogenous DNA.

2. The method for transforming a plant according to claim 1, wherein the different pTi piasmid has a replication origin of an IncP incompatibility group.

3. The method for transforming a plant according to claim 2, wherein the T-DNA region contains three or more gene sequences.

4. The method for transforming a plant according to claim 2, wherein the T-DNA region contains equal to or greater than 25,000 nucleotide base pairs.

5. The method for transforming a plant according to claim 2, wherein the T-DNA region is inserted into a single location in the plant cell when the plant is transformed.

6. The method for transforming a plant according to claim 2, wherein the T-DNA region encodes one or more of an insecticidal protein, a herbicidal protein, or a mixture of insecticidal proteins and herbicide tolerance proteins.

7. The method for transforming a plant according to claim 2, wherein the T-DNA region encodes a Cry1Ca insecticidal protein, a Cry1F insecticidal protein, and a Cry1Ab1 insecticidal protein.

8. The method for transforming a plant according to claim 2, wherein the T-DNA region encodes a Cry1Ca insecticidal protein, a Cry1F insecticidal protein, a Cry1Ab1 insecticidal protein, and an AAD-1 herbicide tolerance protein.

9. The method according to claim 1, wherein the plant is a monocot.

10. The method according to claim 1, wherein the 14.8 KpnI VirBCDG fragment is cloned into the Kpn I site of a pDAB9291 plasmid.

11. The method according to claim 1, wherein the pTi helper plasmid is plasmid pMP90.

12. The method according to claim 1, wherein the pTi helper plasmid is plasmid pTiC58Δ.

13. The method according to claim 10, further comprising transforming the *Agrobacterium* strain using plasmid pDAB9292 DNA.

14. The method according to claim 1, further comprising a step of selecting a transformed cell or a transformed tissue, after subjecting said cultured tissue to transformation.

* * * * *